United States Patent
Guo et al.

(10) Patent No.: US 10,801,060 B2
(45) Date of Patent: Oct. 13, 2020

(54) ASSAYS TO DETERMINE DNA METHYLATION AND DNA METHYLATION MARKERS OF CANCER

(71) Applicant: ZYMO RESEARCH CORPORATION, Irvine, CA (US)

(72) Inventors: Wei Guo, Irvine, CA (US); Paolo Piatti, Irvine, CA (US); Xiaojing Yang, Irvine, CA (US); Xi-Yu Jia, Irvine, CA (US)

(73) Assignee: ZYMO RESEARCH CORPORATION, Irvine, CA (US)

( * ) Notice: Subject to any disclaimer, the term of this patent is extended or adjusted under 35 U.S.C. 154(b) by 203 days.

(21) Appl. No.: 15/552,825

(22) PCT Filed: Feb. 24, 2016

(86) PCT No.: PCT/US2016/019310
§ 371 (c)(1),
(2) Date: Aug. 23, 2017

(87) PCT Pub. No.: WO2016/138105
PCT Pub. Date: Sep. 1, 2016

(65) Prior Publication Data
US 2018/0148776 A1  May 31, 2018

Related U.S. Application Data

(60) Provisional application No. 62/120,373, filed on Feb. 24, 2015.

(51) Int. Cl.
*C12Q 1/68* (2018.01)
*C12Q 1/6858* (2018.01)

(52) U.S. Cl.
CPC ..... *C12Q 1/6858* (2013.01); *C12Q 2521/331* (2013.01); *C12Q 2523/125* (2013.01); *C12Q 2537/143* (2013.01); *C12Q 2545/101* (2013.01); *C12Q 2561/113* (2013.01); *C12Q 2563/107* (2013.01)

(58) Field of Classification Search
USPC ............ 435/6.1, 6.11, 6.12, 91.1, 91.2, 193; 436/94, 501; 536/23.1, 24.3, 24.33, 25.3
See application file for complete search history.

(56) References Cited

U.S. PATENT DOCUMENTS

| | | | |
|---|---|---|---|
| 5,489,507 A | 2/1996 | Chehab | |
| 2002/0045163 A1 | 4/2002 | Salituro et al. | |
| 2003/0219774 A1 | 11/2003 | Sharma et al. | |
| 2005/0095627 A1 | 5/2005 | Kolman et al. | |
| 2005/0158739 A1 | 7/2005 | Jeddeloh et al. | |
| 2005/0202490 A1 | 9/2005 | Makarov et al. | |
| 2005/0272065 A1 | 12/2005 | Lakey et al. | |
| 2007/0231800 A1 | 10/2007 | Roberts et al. | |
| 2008/0081338 A1 | 4/2008 | Lo | |
| 2009/0111707 A1 | 4/2009 | Foekens | |
| 2010/0015622 A1 | 1/2010 | Hanna | |
| 2010/0083407 A1 | 4/2010 | Feldmann et al. | |
| 2010/0248228 A1 | 9/2010 | Wang et al. | |
| 2010/0317000 A1 | 12/2010 | Zhu | |
| 2012/0003634 A1 | 1/2012 | Frumkin et al. | |
| 2013/0065233 A1 | 3/2013 | Jia et al. | |
| 2018/0135113 A1 | 5/2018 | Jia et al. | |

FOREIGN PATENT DOCUMENTS

| | | | |
|---|---|---|---|
| CN | 1451759 A | | 10/2003 |
| CN | 101353695 A | | 1/2009 |
| WO | WO 2005/090607 | | 9/2005 |
| WO | WO 2010/123354 | | 10/2010 |
| WO | WO 2010/149782 | | 12/2010 |
| WO | 2011070441 | † | 6/2011 |
| WO | WO 2011/070441 | | 6/2011 |
| WO | WO 2011/101728 | | 8/2011 |
| WO | WO 2011/109529 | | 9/2011 |
| WO | WO 2012/031008 | | 3/2012 |
| WO | 2014078913 | † | 5/2014 |
| WO | WO 2014/078913 | | 5/2014 |
| WO | WO 2015/169947 | | 11/2015 |

OTHER PUBLICATIONS

Hashimoto, Ko, et al. "Improved quantification of DNA methylation using methylation-sensitive restriction enzymes and real-time PCR." *Epigenetics* 2.2 (2007): 86-91.
Holemon et al., "MethylScreen: DNA methylation density monitoring using quantitative PCR", Biotechniques, 43(5):683-693, 2007.
Hua, Dong, et al. "Quantitative methylation analysis of multiple genes using methylation-sensitive restriction enzyme-based quantitative PCR for the detection of hepatocellular carcinoma" *Experimental and Molecular Pathology* 91.11 (2011): 455-460.
International Invitation to Pay Additional Fees issued in International Application No. PCT/US2016/019310, dated Aug. 30, 2016.
International Preliminary Report on Patentability issued in International Application No. PCT/US2016/019310, dated Aug. 29, 2017.
International Search Report and Written Opinion issued in International Application No. PCT/US2016/019310, dated Aug. 30, 2016.
Kellogg et al., "TaqStart Antibody: 'hot start' PCR facilitated by a neutralizing monoclonal antibody directed against Taq DNA polymerase", Biotechniques, 16(6): 1134-1137, 1994 (Abstract only).
Obayashi et al., "Enzymatic synthesis of labeled DNA by PCR using new fluorescent thymidine nucleotide analogue and superthermophilic KOD dash DNA polymerase", Bioorg Med Chem Lett., 12(8): 1167-1170, 2002. (Abstract only).
Office communication issued European Application No. 16714078. 9, dated May 31, 2018.
Olkhov-Mitsel Ekaterina, et al. "Novel multiplex MethyLight protocol for detection of DNA methylation patient tissues and bodily fluids," *Scientific Reports* 4 (2014): 4432.

(Continued)

*Primary Examiner* — Frank W Lu
(74) *Attorney, Agent, or Firm* — Parker Highlander PLLC

(57) ABSTRACT

Methods are provided for determining a genomic methylation profile in a DNA sample. In certain aspects, the methods can be used to determine if a subject has, or is at risk for developing, a bladder cancer or other cancers of the urinary tract. Methods for treatment of such subjects are likewise provided.

19 Claims, 50 Drawing Sheets

Specification includes a Sequence Listing.

(56) References Cited

OTHER PUBLICATIONS

Singler-Sam et al., A quantative Hpall-PCR assay to measure methylation of DNA from a small number of cells. Nucleic Acids Research, 18, 687, 1990.

Su, Sheng-Fang, et al, "A panel of three markers hyper-and hypomethylated in urine sediments accurately predicts bladder cancer recurrence," *Clinical Cancer Research* 20.7 (2014): 19784989.

Von Kanel et al., "Quantitative 1-step DNA methylation analysis with native genomic DNA as template", Clinical Chemistry, 56(7): 1098-1106, 2010.

Walker, et al., Isothermal in vitro amplification of DNA by a restriction enzyme/DNA polymerase system. Proc. Natl. Acad. Sci. USA, 89, 392-396, 1992.

Beukers, Willemien, et al. "The use of molecular analyses in voided urine for the assessment of patients with hematuria." *PloS One* 8.10 (2013).

Kandimalla, Raju, et al. "A 3-plea methylation assay combined with the FGFR3 mutation assay sensitively detects recurrent bladder cancer in voided urine." *Clinical Cancer Research* 19.17 (2013): 4760-4769.

Partial Search Report issued European Application No. 19190243.6, dated Mar. 11, 2020.

Notice of Opposition issued in corresponding European Application No. 16714078, dated May 5, 2020.

Sequence listing from previously submitted reference WO 2011/070441 (B2), submitted on Jan. 17, 2019, with Hhal cut sites mapped onto particular test loci in underline.

Sequence listing from previously submitted reference WO 2011/070441 (B2), submitted on Jan. 17, 2019, with Hpall and Acil cut sites mapped onto particular test loci in underline and lowercase, respectively.

Extended European Search Report issued in corresponding European Application No. 19190243, dated Jul. 3, 2020.

Kiemeney, Lambertus A., et al. " A sequence variant at 4p16.3 confers susceptibility to urinary bladder cancer." *Nature Genetics* 42.5 (2010): 415-419.

Office Communication issued in corresponding Chinese Application No. 201680012042.4, dated Jun. 19, 2020.

† cited by third party

FIG. 1A-B

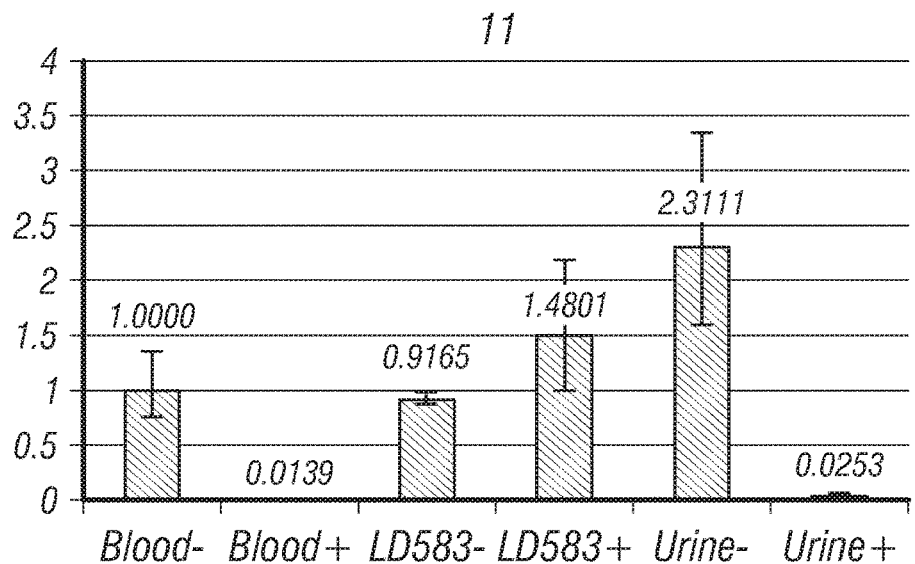
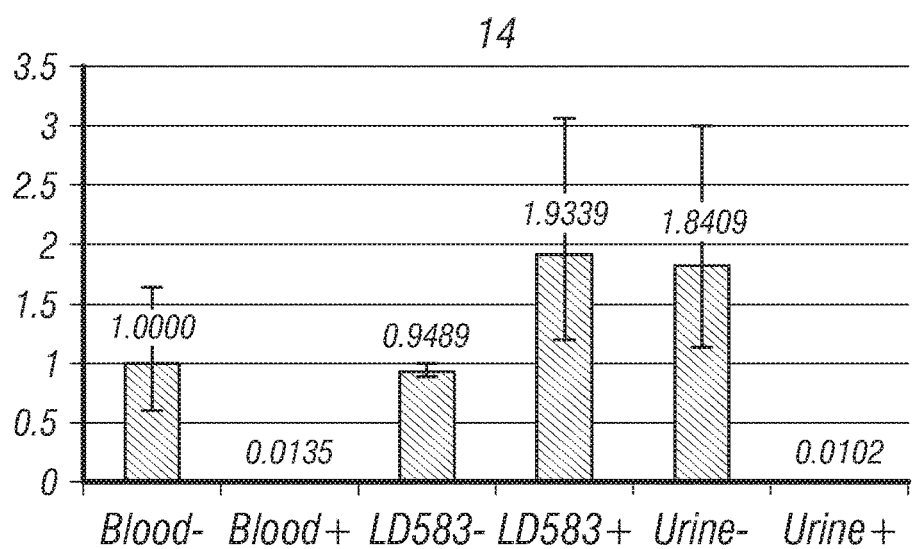
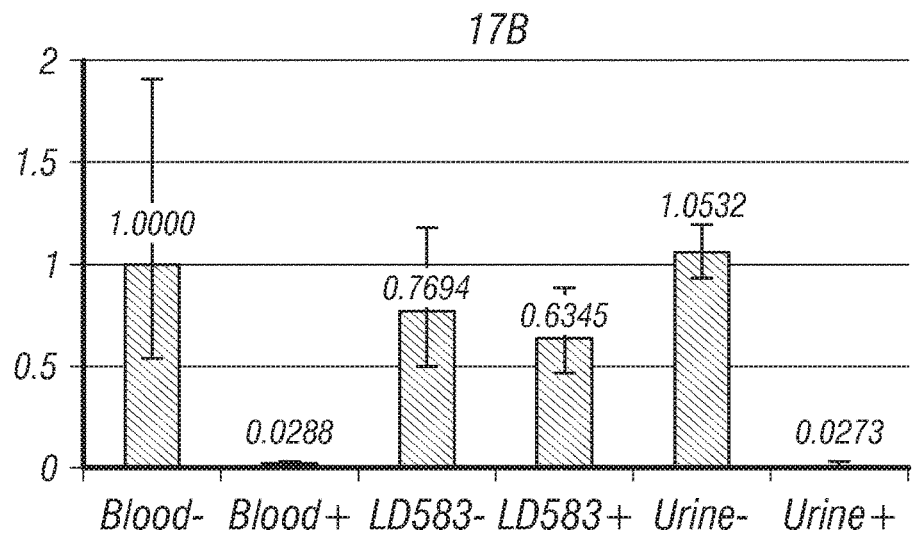
FIG. 5 (Cont'd)

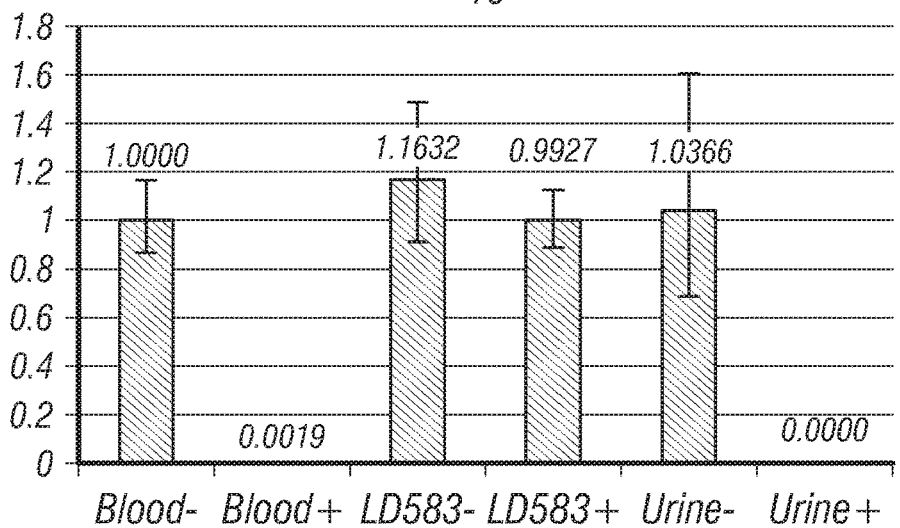
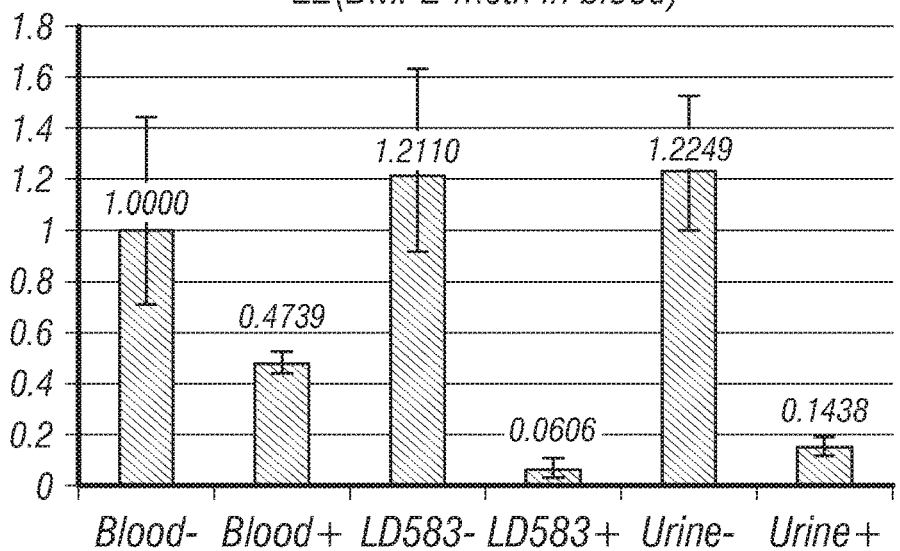
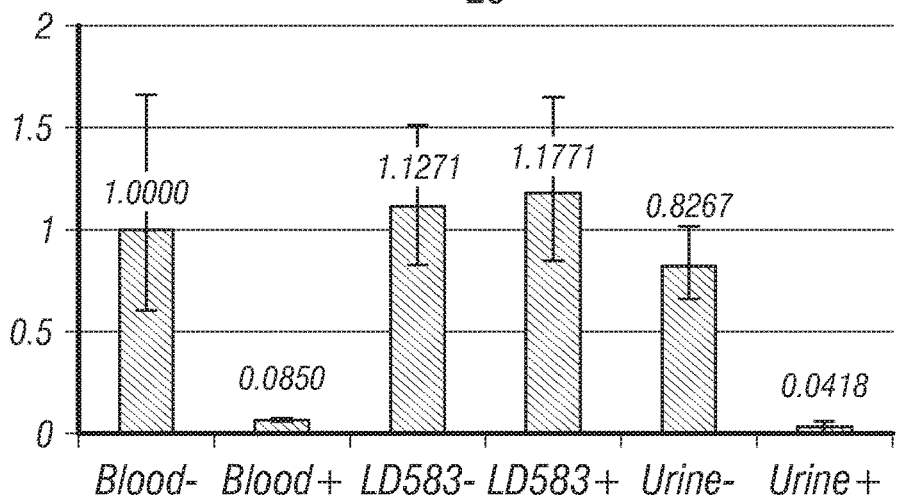
FIG. 6

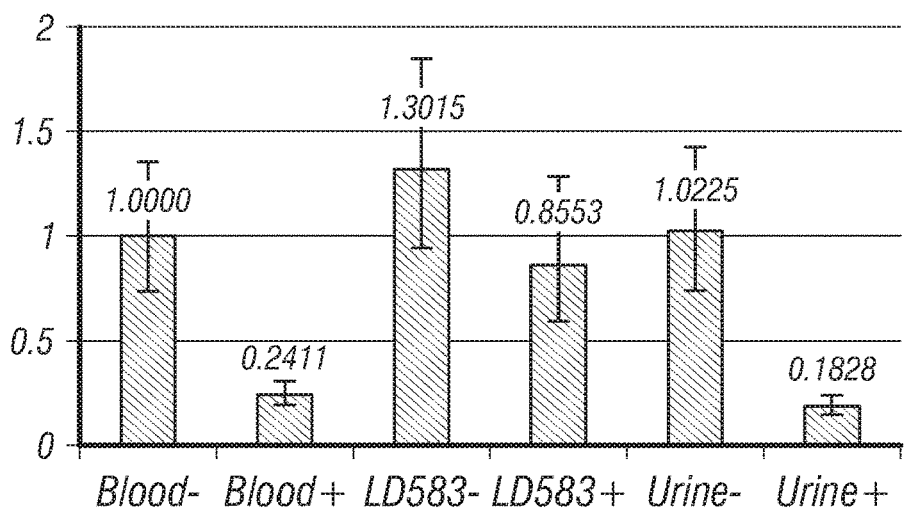
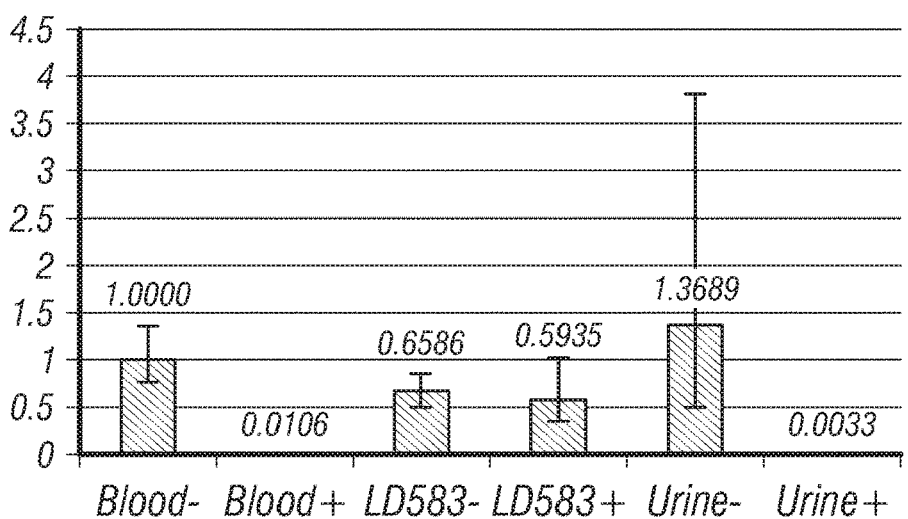
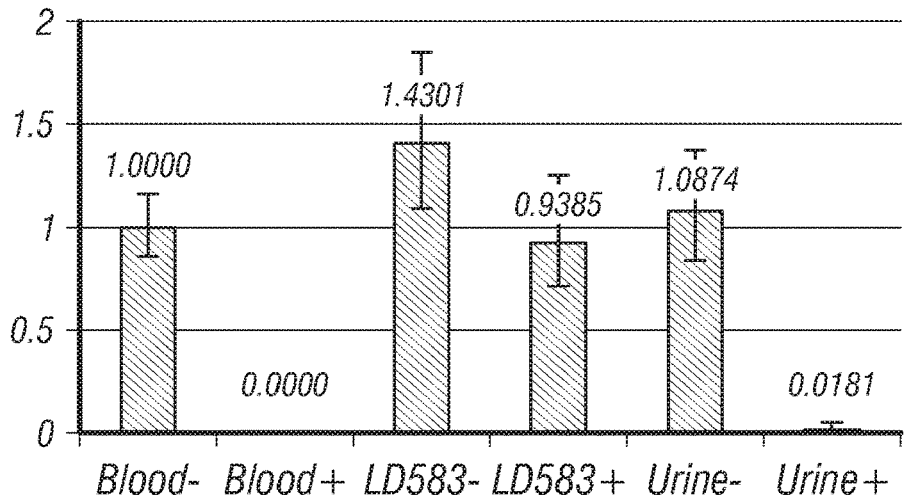
FIG. 7

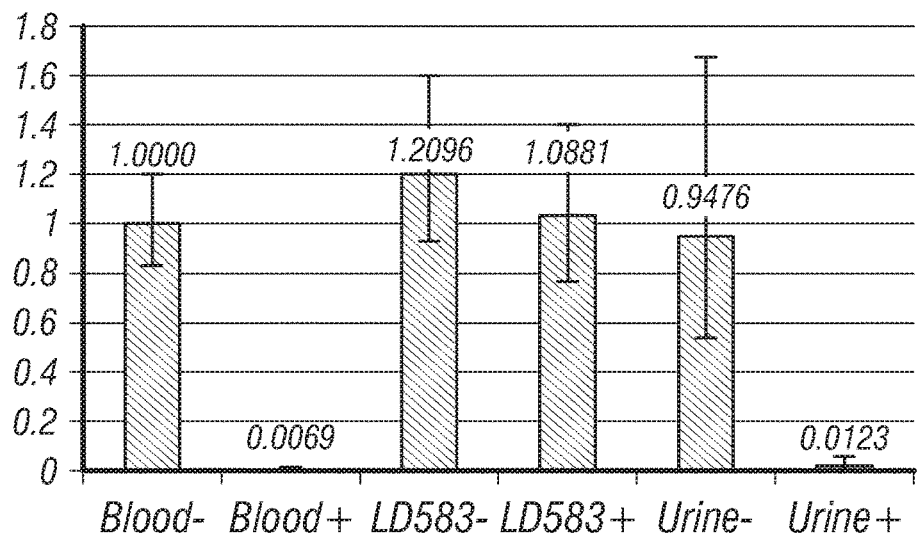
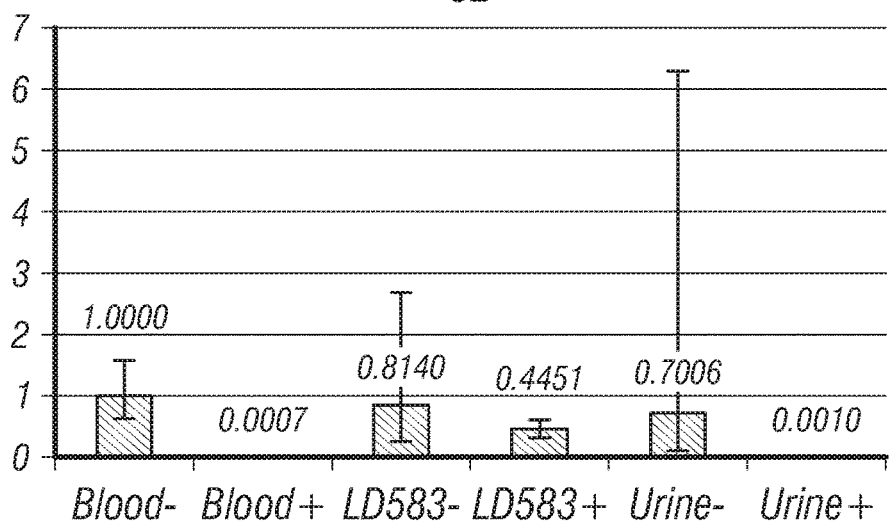
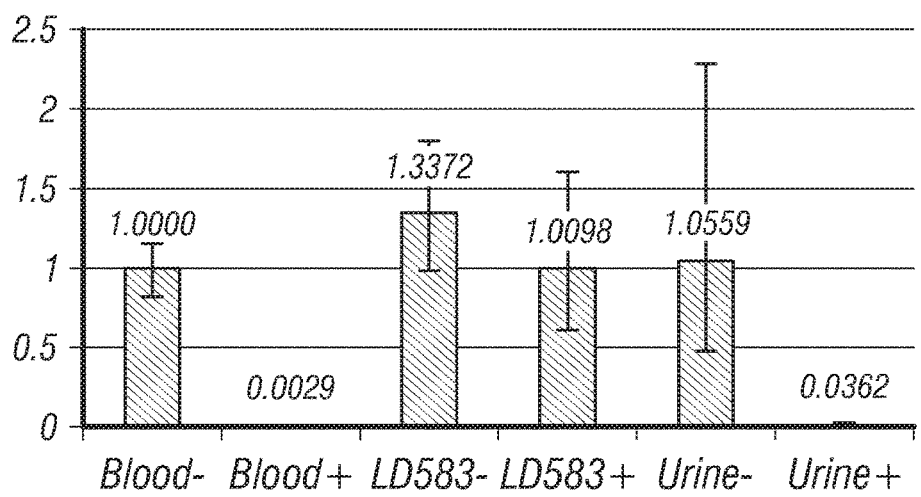
FIG. 7 (Cont'd)

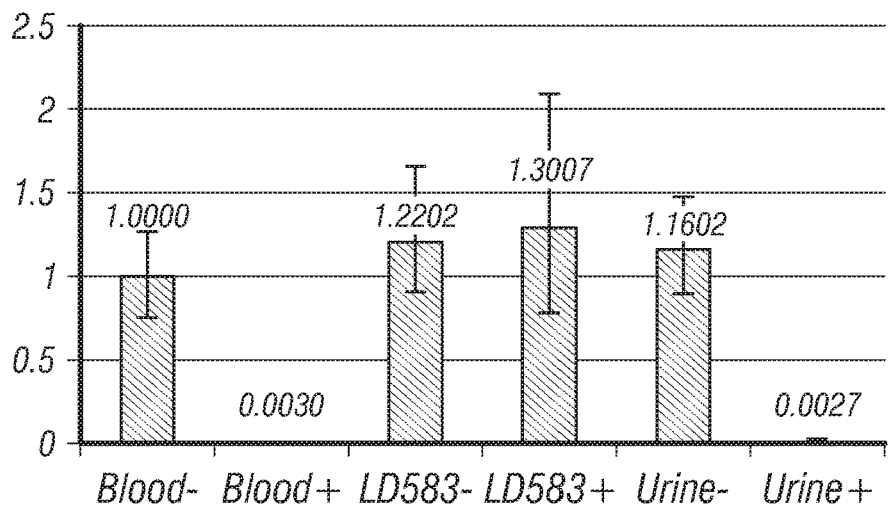
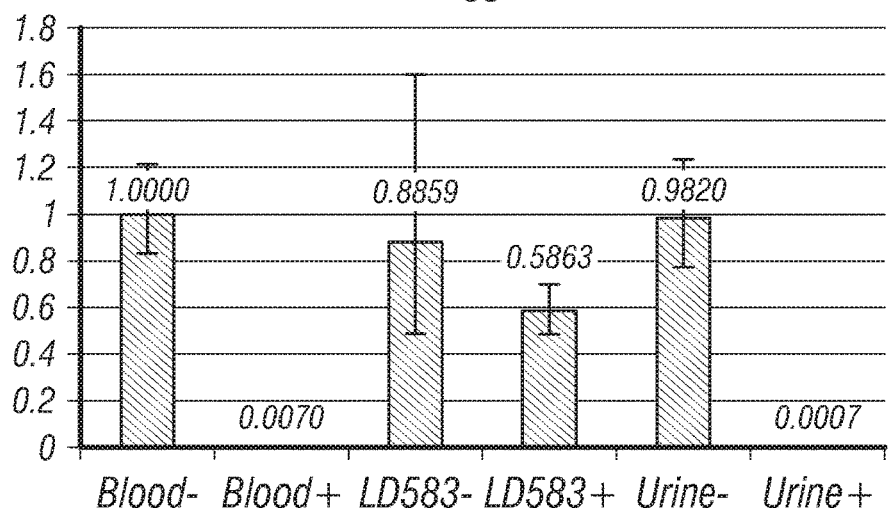
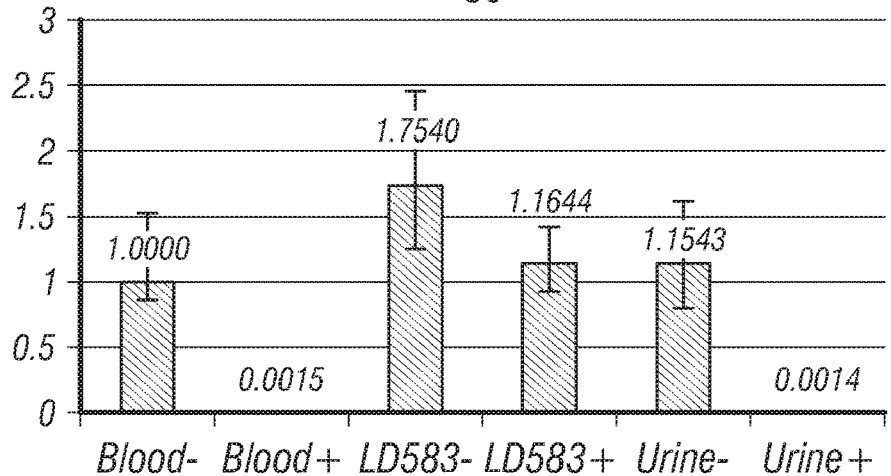
FIG. 7 (Cont'd)

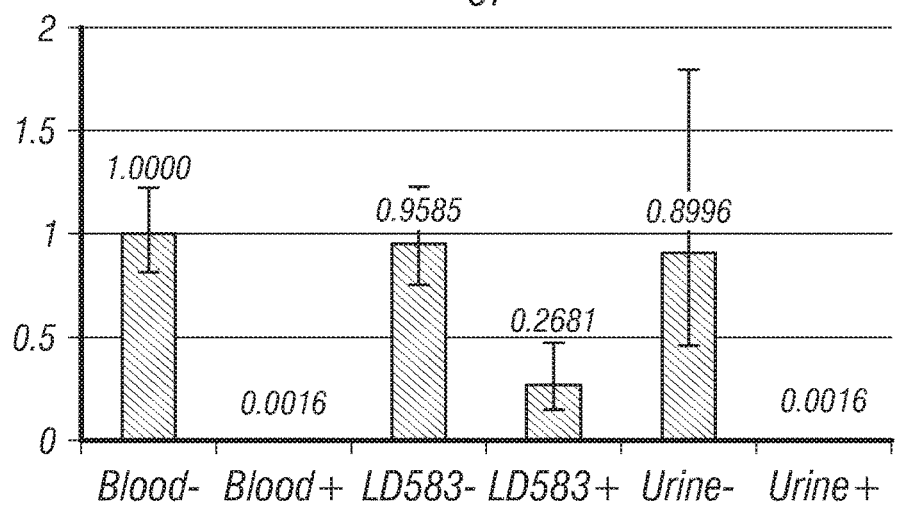
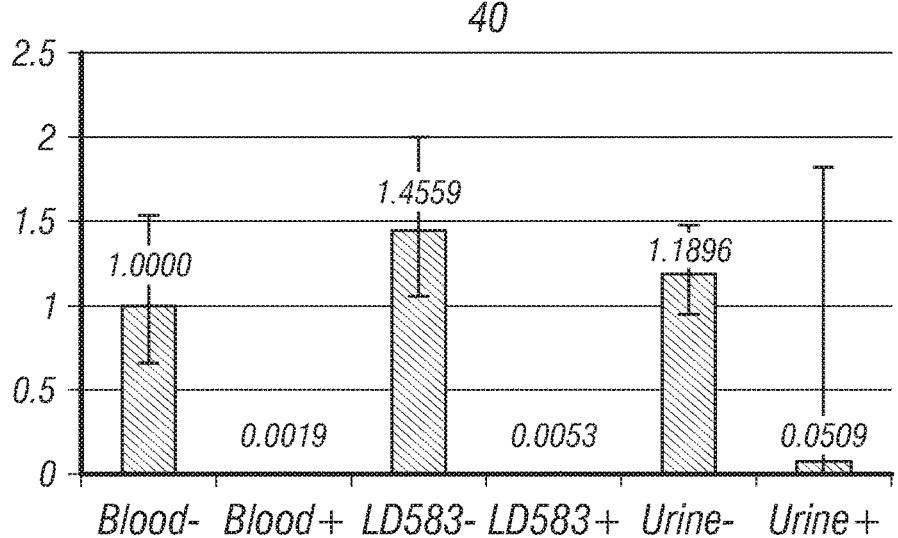
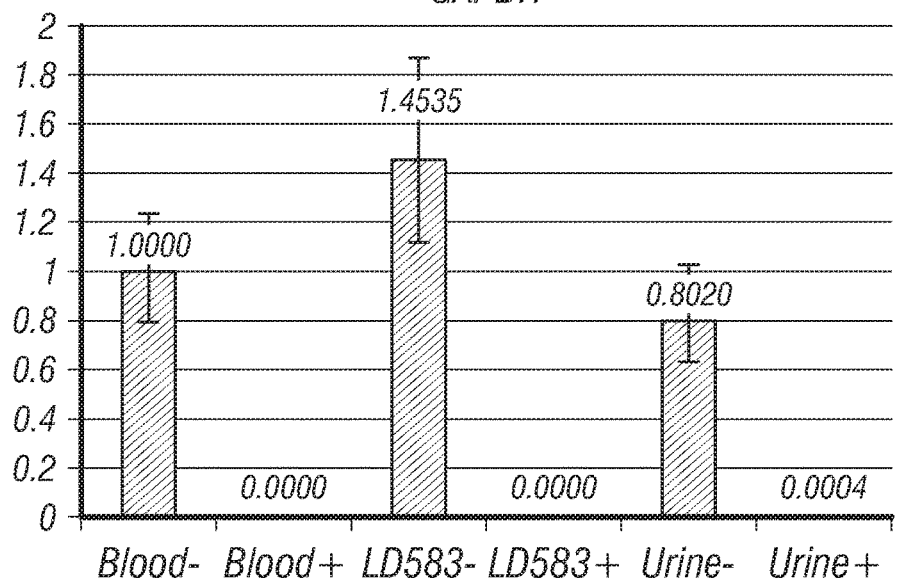
FIG. 8

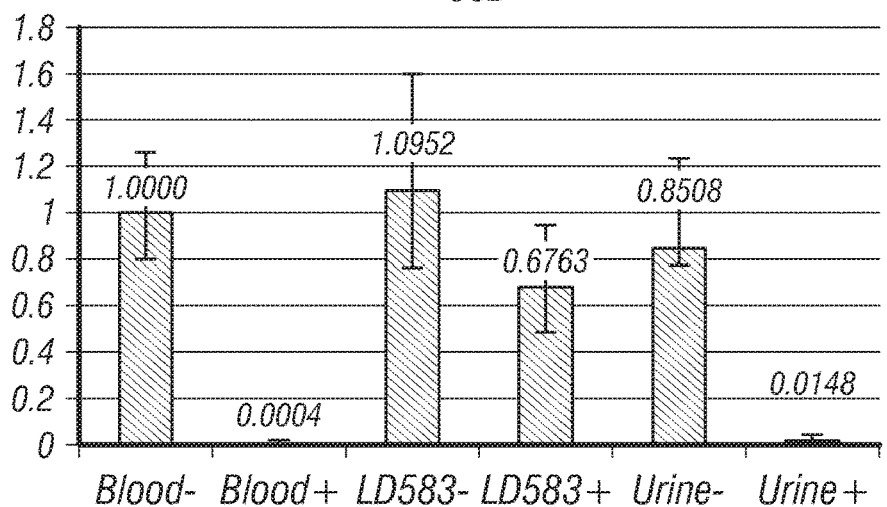
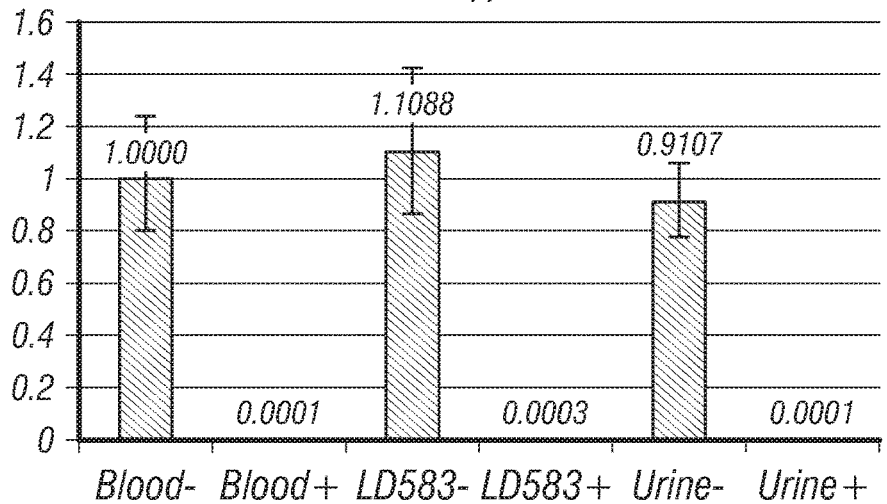
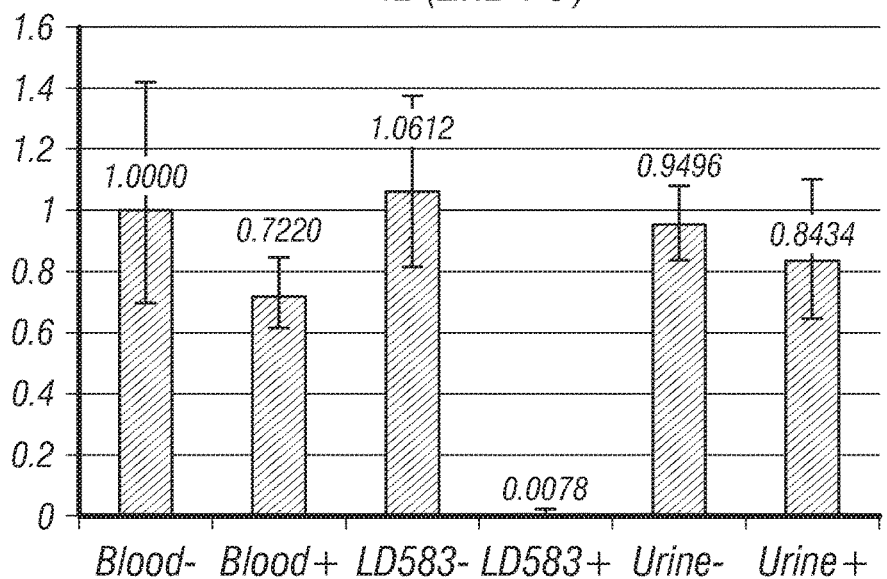
FIG. 8 (Cont'd)

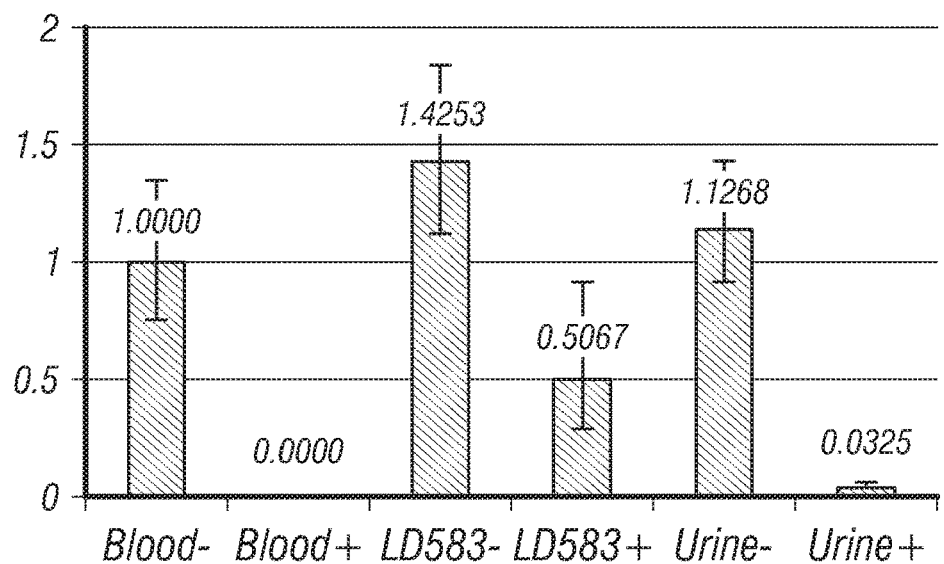
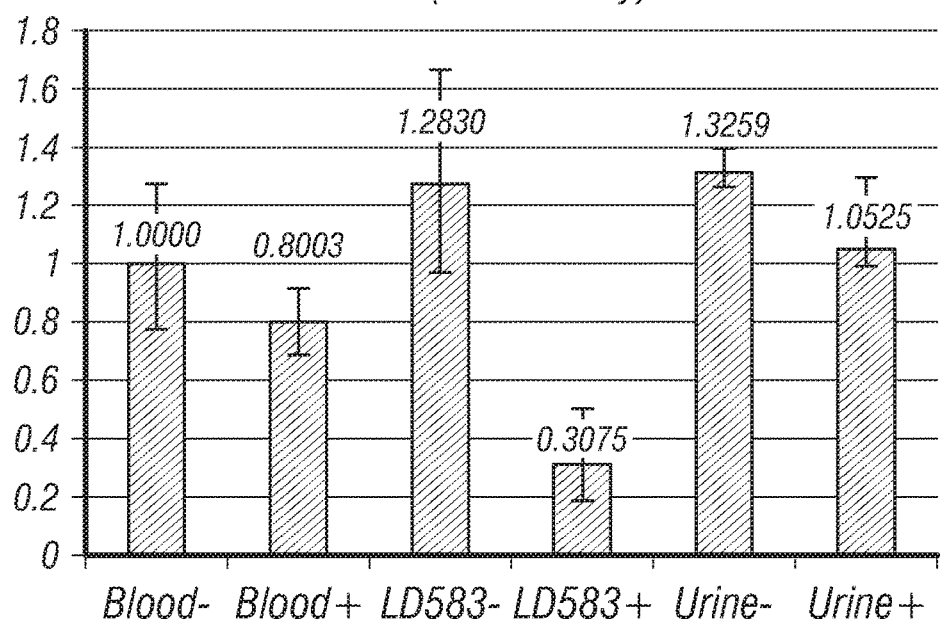
FIG. 8
(Cont'd)

| Blood | | LDS83 | | Urine | |
|---|---|---|---|---|---|
| Undigested | Digested | Undigested | Digested | Undigested | Digested |
| 24.33 | 24.39 | 24.72 | 24.61 | 25.09 | 24.73 |

| | GAPDH | Unk09 | Unk05 | DCHS2/OLX1 | Unk07 | EVX2 | SEPT8/SOX1 | Unk10 | Unk21 | SOX17 | GALR1/TBX15 | EEF1A2 | CMPTA2 | TFAP2B |
|---|---|---|---|---|---|---|---|---|---|---|---|---|---|---|
| mU | | | | | | | | | | | | | | |
| 11909 | 0.00 | 0.04 | 0.00 | 0.08 | 0.46 | 0.09 | 0.00 | (0.59) | 0.14 | 0.00 | 0.00 | 0.00 | 0.00 | 0.00 | (0.58) |
| 11910 | 0.04 | 0.00 | 0.03 | 0.05 | 0.04 | 0.00 | 0.01 | 0.56 | 0.07 | 0.00 | 0.08 | 0.00 | 0.32 | 0.00 | 0.88 |
| mU | | | | | | | | | | | | | | |
| 11911 | 0.00 | 0.00 | 0.06 | 0.00 | 0.24 | 0.07 | 0.00 | 0.00 | 0.05 | 0.00 | 0.00 | 0.00 | 0.00 | 0.00 | 0.22 |
| 11912 | 0.00 | 0.13 | 0.16 | 0.34 | 0.10 | 0.20 | 0.33 | 0.43 | 0.22 | 0.47 | 0.28 | 0.21 | 0.00 | 0.36 |
| mU | | | | | | | | | | | | | | |
| 11915 | 0.03 | 0.00 | 0.02 | 0.00 | (0.44) | 0.00 | 0.07 | 2.31 | 0.04 | 1.67 | 0.00 | 0.00 | 0.00 | (0.79) |
| 9928* | 0.00 | 1.34 | 1.55 | 2.19 | 1.15 | 0.52 | 1.36 | 0.30 | 1.74 | 2.54 | 1.40 | 7.22 | 2.47 | 3.45 |
| mU | | | | | | | | | | | | | | |
| 11943 | 0.00 | 0.00 | 0.00 | 0.00 | (0.30) | 0.00 | 0.00 | 0.00 | 0.09 | 0.02 | 0.02 | 0.06 | 0.00 | 0.22 |
| 11944 | 0.00 | 0.00 | 0.00 | 2.63 | 0.56 | 0.00 | 0.00 | 0.00 | 0.65 | 0.53 | 0.00 | 0.00 | 0.00 | 0.71 |
| mU | | | | | | | | | | | | | | |
| 11946 | 0.00 | 0.04 | 0.00 | 0.06 | 0.16 | 0.00 | 0.00 | 0.15 | 0.08 | 0.00 | 0.14 | 0.00 | 0.00 | (0.37) |
| 11951 | 0.00 | 0.00 | 0.00 | 0.04 | 0.00 | 0.00 | 0.00 | 0.31 | 0.00 | 0.17 | 0.00 | 0.07 | 0.20 | 0.00 | 0.00 |
| mU | | | | | | | | | | | | | | |
| 11886 | 0.00 | 0.12 | 0.00 | 0.05 | (0.26) | 0.08 | 0.09 | (0.29) | 0.09 | 0.19 | 0.32 | 0.33 | 0.17 | 0.00 | (0.38) |
| 11897 | 0.00 | 0.00 | 0.13 | 0.03 | 0.00 | 0.63 | 0.38 | 0.65 | 1.33 | 1.02 | 0.00 | 1.21 | 0.30 | 0.04 | 0.23 |
| mU | | | | | | | | | | | | | | |
| 8982 | 0.29 | 0.00 | 0.00 | 0.10 | (0.47) | 0.05 | 0.28 | 0.07 | 0.36 | 0.18 | 0.00 | 0.05 | 0.22 | 0.16 | 0.42 |

| | GAPDH | Unk 09 | Unk 05 | DCHS2 | Unk 07 | EVX2 | SOX1 | Unk 19 | Unk21 | SOX17 | GALP1 | TBX15 | EEF1A2 | CMRTA2 | RESULTING STATUS |
|---|---|---|---|---|---|---|---|---|---|---|---|---|---|---|---|
| mnU | 0.00 | 0.04 | 0.00 | 0.08 | 0.09 | 0.00 | 0.14 | 0.00 | 0.00 | 0.14 | 0.00 | 0.06 | 0.00 | 0.00 | |
| 11909 | 0.00 | 0.00 | 0.03 | 0.05 | 0.00 | 0.01 | 0.07 | 0.00 | 0.00 | 0.12 | 0.08 | 0.00 | 0.32 | 0.00 | Removed/Normal |
| 11910 | 0.04 | 55.66 | 60.21 | 58.42 | 54.01 | 53.81 | 55.84 | 31.64 | 45.30 | 54.22 | 39.09 | 45.11 | 82.26 | 64.42 | Cancer late stage |
| mnU | 0.00 | 0.00 | 0.00 | 0.00 | 0.07 | 0.00 | 0.05 | 0.00 | 0.00 | 0.09 | 0.00 | 0.00 | 0.21 | 0.00 | |
| 11911 | 0.00 | 32.16 | 41.28 | 41.79 | 18.10 | 30.77 | 24.98 | 25.87 | 15.13 | 15.59 | 20.34 | 14.28 | 11.89 | 51.49 | Cancer late stage |
| 11912 | 0.00 | 0.13 | 1.57 | 0.16 | 0.10 | 0.20 | 0.43 | 0.22 | 0.00 | 0.47 | 0.28 | 0.65 | 0.00 | 0.00 | Removed/Normal |
| mnU | 0.03 | 0.00 | 0.02 | 0.00 | 0.00 | 0.07 | 0.04 | 0.00 | 0.03 | 0.11 | 0.00 | 0.00 | 0.00 | 0.00 | |
| 11913 | 0.00 | 1.34 | 1.55 | 2.19 | 0.52 | 1.30 | 1.74 | 1.67 | 1.41 | 2.54 | 1.48 | 0.08 | 7.22 | 2.47 | Removed?/Cancer Dev |
| 8028 | 0.00 | 1.67 | 23.00 | 5.46 | 29.83 | 0.76 | 10.81 | 12.84 | 4.28 | 15.93 | 0.33 | 3.07 | 3.56 | 0.12 | Removed?/Cancer Dev |
| mnU | 0.00 | 0.01 | 0.00 | 0.00 | 0.00 | 0.00 | 0.09 | 0.00 | 0.00 | 0.02 | 0.02 | 0.00 | 0.06 | 0.00 | |
| 11943 | 0.00 | 0.00 | 0.00 | 0.00 | 0.00 | 0.00 | 0.65 | 0.00 | 0.00 | 0.53 | 0.00 | 0.00 | 0.00 | 0.00 | Removed/Normal |
| 11944 | 0.00 | 0.00 | 0.00 | 0.00 | 0.00 | 0.00 | 0.00 | 0.00 | 0.00 | 0.00 | 0.00 | 0.00 | 0.00 | 0.00 | Removed/Normal |
| mnU | 0.00 | 0.04 | 0.00 | 0.06 | 0.00 | 0.00 | 0.08 | 0.00 | 0.00 | 0.14 | 0.00 | 0.00 | 0.00 | 0.00 | |
| 11946 | 0.00 | 0.00 | 0.00 | 2.89 | 0.00 | 0.00 | 0.00 | 0.00 | 0.00 | 0.00 | 0.00 | 0.00 | 0.00 | 0.00 | Removed/Normal |
| 11951 | 0.00 | 0.07 | 0.13 | 0.04 | 0.00 | 0.00 | 0.17 | 0.18 | 0.00 | 0.07 | 0.00 | 0.00 | 0.20 | 0.00 | Removed/Normal |
| mnU | 0.00 | 0.00 | 0.00 | 0.05 | 0.08 | 0.09 | 0.09 | 0.19 | 0.00 | 0.02 | 0.00 | 0.00 | 0.17 | 0.00 | |
| 11886 | 0.00 | 0.12 | 0.13 | 1.53 | 0.63 | 0.38 | 1.33 | 1.03 | 0.32 | 0.33 | 1.21 | 0.05 | 0.30 | 0.04 | Removed?/Cancer Dev |
| 11897 | 0.00 | 0.00 | 0.00 | 0.03 | 0.05 | 0.28 | 0.36 | 0.18 | 0.00 | 0.10 | 0.05 | 0.00 | 0.22 | 0.00 | Removed/Normal |
| mnU | 0.29 | 0.00 | 0.00 | 0.10 | 0.00 | 0.00 | 0.15 | 0.00 | 0.00 | 0.05 | 0.00 | 0.00 | 0.09 | 0.16 | |
| 8982 | 0.00 | 0.11 | 0.00 | 1.78 | 0.13 | 0.00 | 0.38 | 0.00 | 0.00 | 0.32 | 0.37 | 0.00 | 0.08 | 0.00 | Removed/Normal? |

FIG. 11

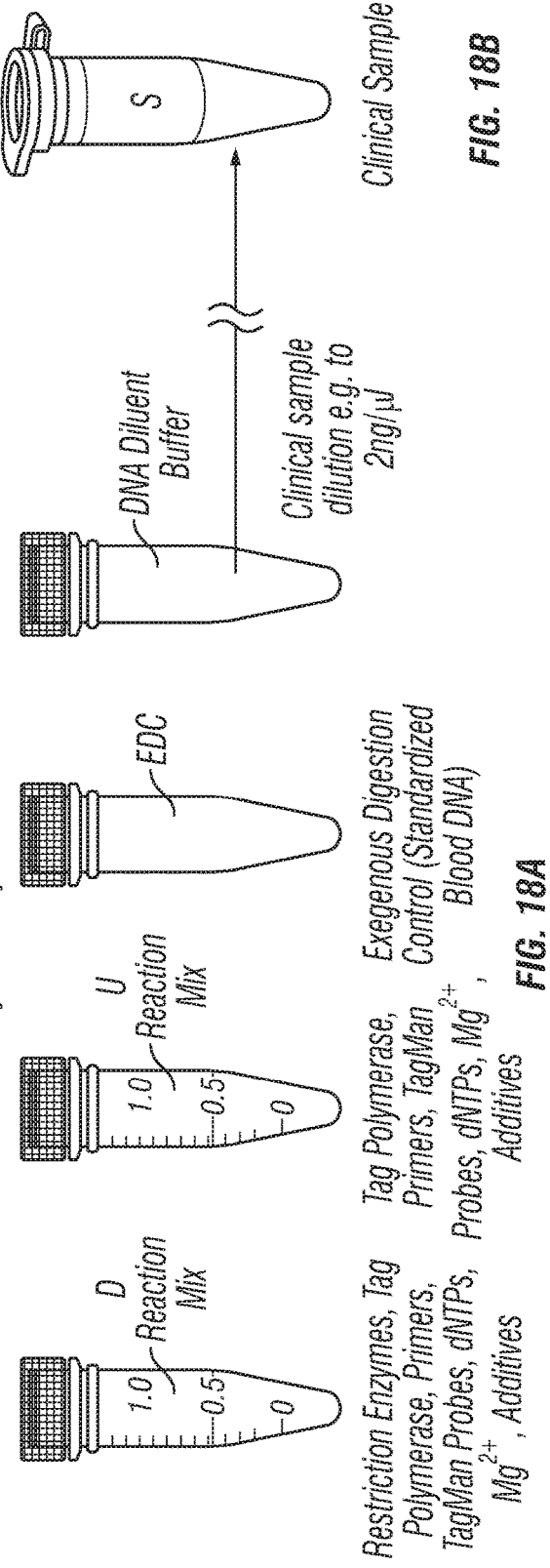
FIG. 18A
FIG. 18B
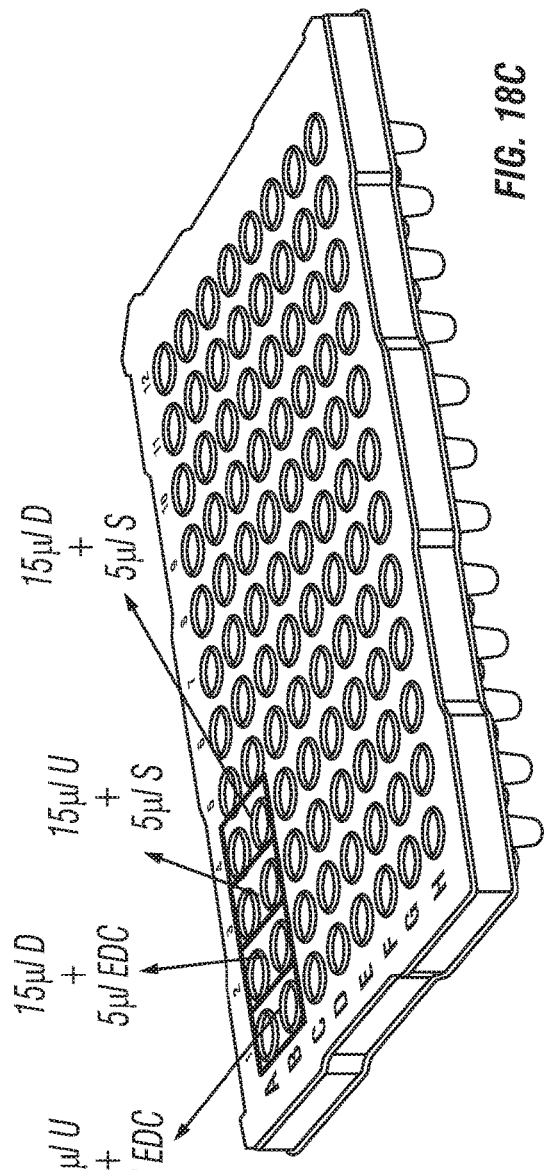
FIG. 18C

Samples

| Markers | E.D.C. − | E.D.C. + | Spl 01 − | Spl 01 + | Spl 02 − | Spl 02 + |
|---|---|---|---|---|---|---|
| POLR2A | 26.16 | 26.12 | 25.47 | 25.20 | 26.79 | 26.91 |
| GAPDH | 27.87 | 42.26 | 27.25 | 40.31 | 27.71 | 40.06 |
| #27 | 24.21 | 33.03 | 24.93 | 33.90 | 24.90 | 25.71 |
| #15 | 25.94 | 35.53 | 26.23 | 35.33 | 26.54 | 27.18 |
| #10 | 27.21 | 38.47 | 28.63 | n.a. | 27.80 | 28.70 |

$\Delta CT = CTm_{(marker\ X)} - CTm_{(POLR2A)}$

FIG. 19A

Samples

| Markers | E.D.C. − | E.D.C. + | Spl 01 − | Spl 01 + | Spl 02 − | Spl 02 + |
|---|---|---|---|---|---|---|
| GAPDH | 1.71 | 16.14 | 1.78 | 15.11 | 0.92 | 13.15 |
| #27 | −1.95 | 6.92 | −0.54 | 8.69 | −1.88 | −1.20 |
| #15 | −0.22 | 9.41 | 0.76 | 10.13 | −0.25 | 0.27 |
| #10 | 1.05 | 12.35 | 3.16 | n.a. | 1.01 | 1.78 |

ΔCT values $\Delta\Delta CT = \Delta CT_{(digested)} - \Delta CT_{(undigested)}$

FIG. 19B

Samples

| Markers | E.D.C. − | E.D.C. + | Spl 01 − | Spl 01 + | Spl 02 − | Spl 02 + |
|---|---|---|---|---|---|---|
| GAPDH | 0.00 | 14.44 | 0.00 | 13.33 | 0.00 | 12.23 |
| #27 | 0.00 | 8.87 | 0.00 | 9.23 | 0.00 | 0.068 |
| #15 | 0.00 | 9.63 | 0.00 | 9.36 | 0.00 | 0.51 |
| #10 | 0.00 | 11.31 | 0.00 | n.a. | 0.00 | 0.77 |

ΔΔCT values $RQ = 2^{-\Delta\Delta CT}$

FIG. 19C

Samples

| Markers | E.D.C. - | E.D.C. + | Spl 01 - | Spl 01 + | Spl 02 - | Spl 02 + | |
|---|---|---|---|---|---|---|---|
| GAPDH | 1.00 | 0.00 | 1.00 | 0.00 | 1.00 | 0.00 | RQ values |
| #27 | 1.00 | 0.00 | 1.00 | 0.00 | 1.00 | 0.62 | |
| #15 | 1.00 | 0.00 | 1.00 | 0.00 | 1.00 | 0.70 | |
| #10 | 1.00 | 0.00 | 1.00 | n.a. | 1.00 | 0.59 | |

↓ Methylation % = RQ x 100

FIG. 19D

Samples

| Markers | E.D.C. - | E.D.C. + | Spl 01 - | Spl 01 + | Spl 02 - | Spl 02 + | |
|---|---|---|---|---|---|---|---|
| GAPDH | 100 | (0.00) | 100 | (0.01) | 100 | (0.02) | OK |
| #27 | 100 | 0.21 | 100 | 0.17 | 100 | 62.27 | |
| #15 | 100 | 0.13 | 100 | 0.15 | 100 | 70.18 | |
| #10 | 100 | 0.04 | 100 | n.a. | 100 | 58.69 | |

Methylation %

OK

↓ Graphical report

FIG. 19E

Samples

| Markers | E.D.C. | Spl 01 | Spl 02 |
|---|---|---|---|
| GAPDH | | | |
| #27 | | | ▓ |
| #15 | | | ▓ |
| #10 | | | ▓ |

| Results | | Neg | Pos |
|---|---|---|---|

Values < 0.25% ⟶ White

Values > 0.25% but < 1% ⟶ Grey

Values > 1% ⟶ Black

FIG. 19F

Plate Setup

| | 1 | 2 | 3 | 4 | 5 | 6 | 7 | 8 | 9 | 10 | 11 | 12 |
|---|---|---|---|---|---|---|---|---|---|---|---|---|
| A | S1 | | | | | | | | | | | S1 |
| B | S2 | | | | | | | | | | | S2 |
| C | S3 | | | | | | | | | | | S3 |
| D | S4 | | | | | | | | | | | S4 |
| E | S5 | | | | | | | | | | | S5 |
| F | S6 | | | | | | | | | | | S6 |
| G | S7 | | | | | | | | | | | S7 |
| H | NTR | | | | | | | | MC | MC | MC | NTR |

FIG. 23

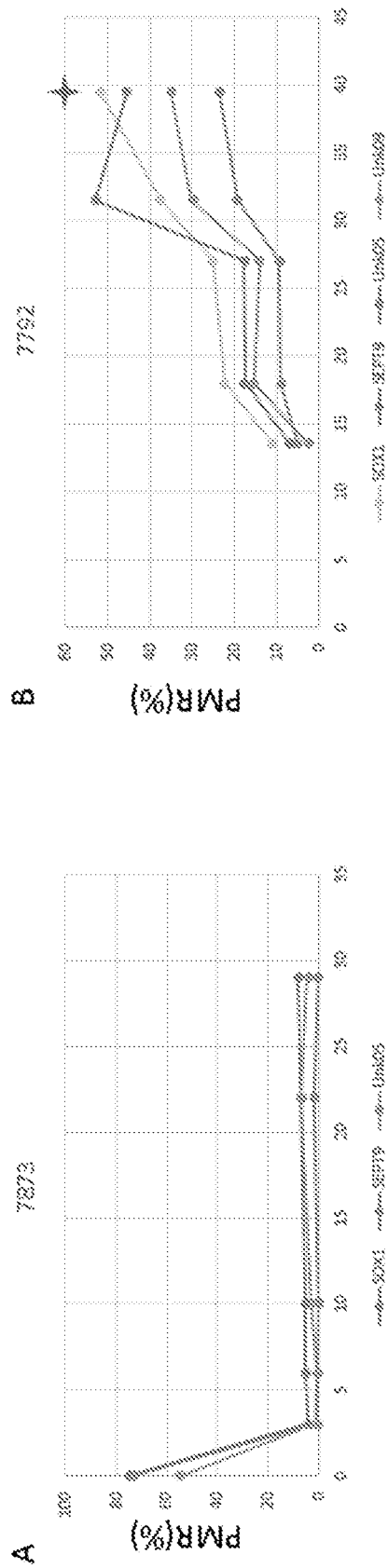
FIG. 27A-B

The following table reflects the sensitivities and specificities of urine tumor markers in bladder cancer as reported in publications.

Sensitivities and specificities of selected urine-based tumor markers in bladder cancer

| Commercially available marker | Sensitivity (%) mean/ range | Specificity (%) mean/ range |
|---|---|---|
| Cytology | 48/ 16-89 | 96/ 81-100 |
| Hematuria dipstick | 68/ 40-93 | 68/ 51-97 |
| BTA stat® | 68/ 53-89 | 74/ 54-93 |
| BTA TRAK® | 61/ 17-78 | 71/ 58-89 |
| NMP22® | 75/ 32-92 | 75/ 51-94 |
| NMP22®BladderChek® | 55.7 | 85.7 |
| ImmunoCyt™ | 74/ 39-100 | 80/ 73-84 |
| UroVysion™ | 77/ 73-81 | 98/ 96-100 |

FIG. 28

RMSE: root mean square error

RMSE: root mean square error

ASSAYS TO DETERMINE DNA METHYLATION AND DNA METHYLATION MARKERS OF CANCER

This application is a national phase application under 35 U.S.C. § 371 of International Application No. PCT/US2016/019310, filed Feb. 24, 2016, which claims the benefit of U.S. Provisional Patent Application No. 62/120,373, filed Feb. 24, 2015, both of which are incorporated herein by reference, in its entirety.

BACKGROUND OF THE INVENTION

1. Field of the Invention

The present invention relates generally to the fields of molecular biology, epigenetics, and predictive medicine. More particularly, it concerns method for determining a genomic DNA methylation profile in a sample.

2. Description of Related Art

Cancers of the urinary tract include bladder, urethral, kidney and prostate cancers whose cells are detectible via urine or biopsy. Bladder cancer was one of the 10 most prevalent malignancies in males in 2011, ranking fourth and eighth in terms of deaths and new cases, respectively (Siegel et al., 2011; Morgan and Clark, 2010). Nonmuscle invasive bladder cancer (NMIBC) accounts for 80% of all the cases, and can be further classified into mucosa only (Ta), carcinoma in situ (Tis), and lamina propria invading, (TI) lesions (Babjuk et al., 2011, Sobin et al., 2009). The primary treatment for NMIBC is transurethral resection of bladder tumor (TURBT) with or without intravesical chemo or immunotherapy; however, more than 50% of patients recur after the TURBT procedure, with the highest rate of recurrence occurring in patients with high-risk disease (Shelley et al., 2010; Millan-Rodriguez et al., 2000). As a result, patients require frequent and lifelong monitoring following TURBT, making bladder cancer one of the most costly types of cancer to manage.

The current standard for monitoring of bladder cancer recurrence involves the use of cystoscopy and cytology (Morgan and Clark, 2010; Babjuk et al., 2011). Disease surveillance is cumbersome because of the invasive nature of cystoscopic examination and the low sensitivity of urinary cytology in the detection of low-grade tumors (Lintula and Hotakainen, 2010). The addition of nuclear matrix protein 22 (NMP-22), bladder tumor antigen, or UroVysion FISH has shown to help increase the sensitivity of cytology (Parker and Spiess, 2011). However, due to their inconsistent performance in terms of specificity or sensitivity, the markers proposed to date have not been widely adopted in routine clinical practice (Reinert 2012). Therefore, there is a need to find reliable markers to monitor bladder cancer patients as well as to distinguish different cancers associated with the urinary tract. Moreover, there is a need to new methodologies for assessing genomic DNA methylation profiles in biological samples.

SUMMARY OF THE INVENTION

In a first embodiment, the invention provides a method for determining a genomic DNA methylation profile in a sample comprising: (a) obtaining a substantially purified test genomic DNA sample; (b) contacting a portion test genomic DNA of the sample with a first reaction mixture comprising: (i) at least two methylation sensitive restriction endonucleases; (ii) a hot-start DNA polymerase; (iii) a pH buffered salt solution; (iv) dNTPs; (v) DNA primer pairs for polymerase chain reaction (PCR) amplification of at least a first, second and third different genomic region in the DNA sample; and (vi) fluorescent probes complementary to sequences in said first, second and third different genomic regions for quantitative detection of amplified sequences from the first, second and third different genomic regions, wherein each of the probes comprises a distinct fluorescent label; wherein (I) the first genomic region is a cleavage control that is known to be unmethylated, (II) the second genomic region is a copy number control that does not include any cut sites for the methylation sensitive restriction endonucleases of the first reaction mixture, and (III) the third genomic region is a test region having an unknown amount of methylation and including at least three cut sites for the methylation sensitive restriction endonucleases of the first reaction mixture; (c) subjecting the first reaction mixture to digestion and thermal cycling, while detecting fluorescent signals from the fluorescent probes, thereby performing real time PCR on the samples in the first and second reaction mixtures; and (d) using the detected fluorescent signals to determine the genomic DNA methylation profile in a sample.

In further aspects, the method additionally comprises: (a) obtaining a substantially purified test genomic DNA sample; (b) contacting a portion test genomic DNA of the sample with a first reaction mixture comprising: (i) at least two methylation sensitive restriction endonucleases; (ii) a hot-start DNA polymerase; (iii) a pH buffered salt solution; (iv) dNTPs; (v) DNA primer pairs for polymerase chain reaction (PCR) amplification of at least a first, second and third different genomic region in the DNA sample; and (vi) fluorescent probes complementary to sequences in said first, second and third different genomic regions for quantitative detection of amplified sequences from the first, second and third different genomic regions, wherein each of the probes comprises a distinct fluorescent label; and a second reaction mixture, identical to the first reaction mixture, but lacking the at least two methylation sensitive restriction endonucleases, wherein: (I) the first genomic region is a cleavage control that is known to be unmethylated; (II) the second genomic region is a copy number control that does not include any cut sites for the methylation sensitive restriction endonucleases of the first reaction mixture; and (III) the third genomic region is a test region having an unknown amount of methylation and including at least three cut sites for the methylation sensitive restriction endonucleases of the first reaction mixture; (c) subjecting the first and second reaction mixtures to digestion and thermal cycling, while detecting fluorescent signals from the fluorescent probes, thereby performing real time PCR on the samples in the first and second reaction mixtures; and (d) using the detected fluorescent signals to determine the genomic DNA methylation profile in a sample.

In some aspects, the first reaction mixture further comprises a PCR enhancer. In specific aspects, the PCR enhancer may comprise DMSO. In certain aspects, obtaining a substantially purified test genomic DNA sample may comprise purifying the DNA sample. In several aspects, the substantially purified test genomic DNA sample is of sufficient purity to provide at least 85%, 90%, 95% or 99% digestion of the DNA by said at least two methylation sensitive restriction endonucleases in 2 hours at 30° C. In particular aspects, the substantially purified test genomic DNA sample comprises 50 pg to 1,000 ng of DNA. In some specific aspects, the substantially purified test genomic DNA sample comprises less than 50 ng of DNA.

In certain aspects, the substantially purified test genomic DNA sample may be obtained from a urine, stool, saliva, blood or tissue sample. In some particular aspects, the substantially purified test genomic DNA sample is obtained from a biopsy sample. In other particular aspects, the substantially purified test genomic DNA sample is obtained from a urine sample. In several aspects, the first reaction mixture comprises at least three methylation sensitive restriction endonucleases. In further aspects, the at least three methylation sensitive restriction endonucleases comprise AciI, HinP1I and HpaII.

In some aspects, step (b) may further comprise contacting a portion test genomic DNA of the sample with a first reaction mixture comprising: (i) at least two methylation sensitive restriction endonucleases; (ii) a hot-start DNA polymerase; (iii) a pH buffered salt solution; (iv) dNTPs; (v) DNA primer pairs for polymerase chain reaction (PCR) amplification of at least a first, second, third and fourth different genomic region in the DNA sample; and (vi) fluorescent probes complementary to sequences in said first, second, third and fourth different genomic regions for quantitative detection of amplified sequences from the first, second, third and fourth different genomic regions, wherein each of the probes comprises a distinct fluorescent label, wherein: (I) the first genomic region is a cleavage control that is known to be unmethylated, (II) the second genomic region is a copy number control that does not include any cut sites for the methylation sensitive restriction endonucleases of the first reaction mixture, and (III) the third and fourth genomic regions are test regions having an unknown amount of methylation and including at least three cut sites for the methylation sensitive restriction endonucleases of the first reaction mixture.

In further aspects, step (b) may additionally comprise contacting a portion test genomic DNA of the sample with a first reaction mixture comprising: (i) at least two methylation sensitive restriction endonucleases; (ii) a hot-start DNA polymerase; (iii) a pH buffered salt solution; (iv) dNTPs; (v) DNA primer pairs for polymerase chain reaction (PCR) amplification of at least a first, second, third, fourth and fifth different genomic region in the DNA sample; and (vi) fluorescent probes complementary to sequences in said first, second, third, fourth and fifth different genomic regions for quantitative detection of amplified sequences from the first, second, third, fourth and fifth different genomic regions, wherein each of the probes comprises a distinct fluorescent label, and wherein (I) the first genomic region is a cleavage control that is known to be unmethylated, (II) the second genomic region is a copy number control that does not include any cut sites for the methylation sensitive restriction endonucleases of the first reaction mixture, and (III) the third, fourth and fifth genomic regions are test regions having an unknown amount of methylation and including at least three cut sites for the methylation sensitive restriction endonucleases of the first reaction mixture. In certain aspects, the third, fourth and fifth genomic regions may be regions of Unk05, Unk09 and SOX17. In still further aspects, a method of the embodiments further comprises determining whether the cells comprise an aneuploidy relative to one or more gene region.

In several aspects, at least 4, 5, 6, 7 or 8 cut sites for the methylation sensitive restriction endonucleases of the first reaction mixture. In some aspects, the primer pairs are complementary to sequences no more than 300, 275, 250, 225, 200, 190, 180, 170, 160, 150, 140, 130, 120, 110,100, 90, 80, 70, 60 or 50 nucleotides apart. In certain aspects, the first genomic region is a genomic region of a housekeeping gene. The housekeeping gene may be GAPDH. In still further aspects, the second genomic region may be a genomic region of the POLR2A gene. In some aspects, the third genomic region is selected from the group provided in Table 1A or Table 2. In some specific aspects, the third genomic region is selected from the group consisting of DMRTA2, EVX2, Unk21, OTX1, SOX1, SEPT9, Unk05, Unk09, GALR1, Unk07, Unk19, TBX15, EEF1A2, TFAP2B, DCHS2 and SOX17. In a particular aspect, using the detected fluorescent signals to determine the genomic DNA methylation profile in a sample comprises calculating the relative methylation percentages for the sample. In still further aspects, a method of the embodiments comprises the use of one or more of the probes or primer pairs provided in Table 1C.

In a further embodiment, the invention provides a reaction mixture comprising: (i) at least two methylation sensitive restriction endonucleases; (ii) a hot-start DNA polymerase; (iii) a pH buffered salt solution; (iv) dNTPs; (v) a substantially purified genomic DNA sample; (vi) DNA primer pairs for polymerase chain reaction (PCR) amplification of at least a first, second and third different genomic region in the DNA sample; (vii) fluorescent probes complementary to sequences in said first, second and third different genomic regions for quantitative detection of amplified sequences from the first, second and third different genomic regions, wherein each of the probes comprises a distinct fluorescent label wherein: (I) the first genomic region is a cleavage control that is known to be unmethylated; (II) the second genomic region is a copy number control that does not include any cut sites for the methylation sensitive restriction endonucleases of the first reaction mixture; and (III) the third genomic region is a test region having an unknown amount of methylation and including at least three cut sites for the methylation sensitive restriction endonucleases of the first reaction mixture. In some aspects, the third genomic region is selected from the group provided in Table 1A or Table 2. In still further aspects, the probes complementary to sequences in said first, second and third different genomic regions are selected from the probes provided in Table 1C.

In still a further embodiment, there is provided a method for determining a genomic DNA methylation profile in a sample comprising: (a) obtaining a test genomic DNA sample, which has been bisulfite converted; (b) contacting the test sample with a first reaction mixture comprising: (i) a hot-start DNA polymerase; (ii) a pH buffered salt solution; (iii) dNTPs; (iv) DNA primer pairs for polymerase chain reaction (PCR) amplification of at least a first, and second different genomic region in the DNA sample, wherein the primer pairs are complementary to sequences no more than 200 nucleotides apart; and (v) fluorescent probes complementary to sequences in said first, and second different genomic regions for quantitative detection of amplified sequences from the first and second different genomic regions, wherein each of the probes comprises a distinct fluorescent label, wherein: (I) the first genomic region is a copy number control region that that does not comprise CpG dinucleotides; and (II) the second genomic region is a test region having an unknown amount of methylation and including at least five CpG dinucleotides in sequences that are complementary to DNA primer pairs and the probe for the second genomic region; (c) subjecting the first reaction mixtures to thermal cycling, while detecting fluorescent signals from the fluorescent probes, thereby performing real time PCR on the sample in the first reaction mixture; and (d)

using the detected fluorescent signals and fluorescent signal from a DNA methylation standard curve to determine the genomic DNA methylation profile in a sample.

In yet still a further embodiment, the invention provides a method for determining a genomic DNA methylation profile in a sample comprising: (a) obtaining a test genomic DNA sample, which has been bisulfite converted, and a methylation control genomic DNA sample that has been fully methylated; (b) contacting the test sample with a first reaction mixture comprising: (i) a hot-start DNA polymerase; (ii) a pH buffered salt solution; (iii) dNTPs; (iv) DNA primer pairs for polymerase chain reaction (PCR) amplification of at least a first and second different genomic region in the DNA sample, wherein the primer pairs are complementary to sequences no more than 200 nucleotides apart; and (v) fluorescent probes complementary to sequences in said first and second different genomic regions for quantitative detection of amplified sequences from the first and second different genomic regions, wherein each of the probes comprises a distinct fluorescent label, wherein: (I) the first genomic region is a copy number control region that that does not comprise CpG dinucleotides; and (II) the second genomic region is a test region having an unknown amount of methylation and including at least five CpG dinucleotides in sequences that are complementary to DNA primer pairs and the probe for the second genomic region; (c) contacting the methylation control bisulfite converted genomic DNA sample with a second reaction mixture having identical components as said first reaction mixture; (d) subjecting the first and second reaction mixtures to thermal cycling, while detecting fluorescent signals from the fluorescent probes, thereby performing real time PCR on the samples in the first and second reaction mixtures; and (e) using the detected fluorescent signals and fluorescent signal from a DNA methylation standard curve to determine the genomic DNA methylation profile in a sample.

In some aspects of the embodiments described herein, the methods further comprise using the detected fluorescent signals of the first genomic region to normalize DNA quantity across all tested samples. In certain aspects, the first reaction mixture may further comprise a PCR enhancer. In particular aspects, the PCR enhancer comprises DMSO. In several aspects, determining the genomic DNA methylation profile comprises determining the copy number of methylated DNA molecules. In still further aspects, the method may additionally comprise using the detected fluorescent signals to determine ratio of methylation in the test sample to the reference methylation control. In specific aspects, the genomic DNA sample comprises 50 pg to 10 ng of DNA. In certain aspects, the genomic DNA sample may comprise DNA isolated from 6 to 1,500 cells.

In yet still further aspects of the embodiments described herein, the methods may additionally comprise obtaining a genomic DNA sample and subjecting the genomic DNA sample to bisulfite conversion. In specific aspects, the genomic DNA is obtained from a urine, stool, saliva, blood or tissue sample. In other aspects, the genomic DNA is obtained from a biopsy sample. In a particular aspect, the genomic DNA is obtained from a urine sample.

In certain aspects, step (b) further comprises contacting the test sample with a first reaction mixture comprising: (i) a hot-start DNA polymerase; (ii) a pH buffered salt solution; (iii) dNTPs; (iv) DNA primer pairs for PCR amplification of at least a first, second and third different genomic region in the DNA sample, wherein the primer pairs are complementary to sequences no more than 200 nucleotides apart; and (v) fluorescent probes complementary to sequences in said first, second and third different genomic regions for quantitative detection of amplified sequences from the first, second and third different genomic regions, wherein each of the probes comprises a distinct fluorescent label, wherein: (I) the first genomic region is a copy number control region that that does not comprise CpG dinucleotides; and (II) the second and third genomic regions are test regions having an unknown amount of methylation and including at least five CpG dinucleotides in sequences that are complementary to DNA primer pairs and the probe for the second and third genomic regions. In a particular aspect, step (b) may still further comprise contacting the test sample with a first reaction mixture comprising: (i) a hot-start DNA polymerase; (ii) a pH buffered salt solution; (iii) dNTPs; (iv) DNA primer pairs for PCR amplification of at least a first, second, third, fourth and fifth different genomic region in the DNA sample, wherein the primer pairs are complementary to sequences no more than 200 nucleotides apart; and (v) fluorescent probes complementary to sequences in said first, second, third, fourth and fifth different genomic regions for quantitative detection of amplified sequences from the first, second, third, fourth and fifth different genomic regions, wherein each of the probes comprises a distinct fluorescent label, wherein: (I) the first genomic region is a copy number control region that that does not comprise CpG dinucleotides; and (II) the second, third, fourth and fifth genomic regions are test regions having an unknown amount of methylation and including at least five CpG dinucleotides in sequences that are complementary to DNA primer pairs and the probe for the second, third, fourth and fifth genomic regions In several aspects of the embodiments described herein, the second genomic region includes at least 6, 7, 8, 9 or 10 CpG dinucleotides in sequences that are complementary to DNA primer pairs and the probe for the second region. In some specific aspects, one of said CpG dinucleotides in sequences that are complementary to DNA primer pairs includes a C positioned in the last five nucleotides at the 3' end of the DNA primer pairs. In a further aspect, the C may be positioned at the 3' end of the DNA primer pairs.

In certain aspects, the primer pairs are complementary to sequences no more than 170, 160, 150, 140, 130, 120, 110 or 100 nucleotides apart. In some aspects, each of the probes is no more than 40 bp in length. In some particular aspects, each of the probes is no more than 30 bp in length. In several aspects, each of the probes comprises a CG ratio of 30-80%. In specific aspects, each of the primers has a Tm of 55-62° C. In a further aspect, each of the probes may have a Tm of 65-72° C.

In yet still further aspects, the copy number control region is region of the COL2A1 gene. In some aspects, the second genomic region is selected from the group provided in Table 1A. In some particular aspects, the second genomic region is selected from the group consisting of DMRTA2, EVX2, Unk21, OTX1, SOX1, SEPT9, Unk05, Unk09, GALR1, Unk07, Unk19, TBX15, EEF1A2, TFAP2B, DCHS2 and SOX17. In certain aspects, using the detected fluorescent signals to determine the genomic DNA methylation profile in a sample comprises calculating the relative methylation percentages for the sample.

In yet a further embodiment there is provided a synthetic polynucleotide sequence comprising a sequence at least 90%, 91%, 92%, 93%, 94%, 95%, 96%, 97%, 98% or 99% identical to one of the probe sequences selected from those provided in Table 1B or 1C, wherein the polynucleotide is conjugated to a reporter molecule. In some aspects, the synthetic polynucleotide comprises a sequence identical to one of the probes of Table 1B or 1C. In certain aspects, the reporter molecule is a fluorophore.

In still a further embodiment there is provided a primer pair, where the primers comprise a sequence at least 90%, 91%, 92%, 93%, 94%, 95%, 96%, 97%, 98% or 99% identical to one of the primer sequences selected from those provided in Table 1B or 1C. In some aspects, the primer pair comprises primers having a sequence identical to a primer pair of Table 1B or 1C.

In still further aspects, a kit is provide comprising reagents for preforming qPCR and a recombinant polynucleotide sequence comprising a sequence at least 90%, 91%, 92%, 93%, 94%, 95%, 96%, 97%, 98% or 99% identical to one of the probe sequences selected from those provided in Table 1B or 1C, wherein the polynucleotide is conjugated to a reporter molecule.

In a further embodiment, the invention provides a method of treating a patient comprising determining a genomic methylation profile for the patient in accordance with any one of embodiments and aspects described above and performing a treatment on the patient based on the genomic methylation profile. In certain aspects, the treatment comprises performing a biopsy of the patient. In some aspects, the treatment comprises administering an anti-cancer therapy to the patient. The anti-cancer therapy may be chemotherapy, radiotherapy, gene therapy, surgery, hormonal therapy, anti-angiogenic therapy or cytokine therapy.

In a further embodiment there is provided a method of detecting the presence of, or an increased risk of, bladder cancer or other cancers of the urinary tract in a patient comprising determining a methylation status in one or more genomic regions in a patient sample selected from the group provided in Table 1A wherein an increased level of methylation in one or more of the genomic regions of Table 1A relative to a reference level indicates that the patient has or is at risk of developing bladder cancer.

In some aspects, one or more genomic regions is selected from the group consisting of Unk 09, Unk 05, DCHS2, OTX1, Unk 07, EVX2, SEPT9, SOX1, Unk 19, Unk 21, and SOX 17 (as indicated in Table 1A). In certain aspects, the one or more genomic regions is selected from 2, 3, 4, 5, 6, 7, 8, 9, 10 or 11 of the genomic regions selected from the group consisting of Unk 09, Unk 05, DCHS2, OTX1, Unk 07, EVX2, SEPT9, SOX1, Unk 19, Unk 21, and SOX17 (as indicated in Table 1A).

In other aspects, the one or more genomic regions is selected from the group consisting of GALR1, TBX15, EEF1A2, DMRTA2, and TFAP2B (as indicated in Table 1A). In some aspects, the one or more genomic regions is selected from 2, 3, 4, or 5 of the genomic regions selected from the group consisting of GALR1, TBX15, EEF1A2, DMRTA2, and TFAP2B (as indicated in Table 1A).

In certain aspects, the one or more genomic regions is selected from the group consisting of SCT, Unk 14, Unk 29, CERKL, and SHH (as indicated in Table 1A). In further aspects, the one or more genomic regions is selected from 2, 3, 4, or 5 of the genomic regions selected from the group consisting of SCT, Unk 14, Unk 29, CERKL, and SHH (as indicated in Table 1A).

In some aspects, said determining comprises determining a methylation status in two, three or more of said genomic regions. In certain aspects, said determining comprises determining a methylation status in 2, 3, 4, 5, 6, 7, 8, 9, 10 or more of said genomic regions. In some aspects, said determining comprises determining a methylation status in 2, 3, 4, 5, 6, 7, 8, 9, 10 or more of said genomic regions, wherein the genomic regions are selected from the group consisting of Unk 09, Unk 05, DCHS2, OTX1, Unk 07, EVX2, SEPT9, SOX1, Unk 19, Unk 21, SOX17, GALR1, TBX15, EEF1A2, DMRTA2, and TFAP2B (as indicated in Table 1A). In further aspects, said determining comprises determining a methylation in each of the genomic regions: Unk 09, Unk 05, DCHS2, OTX1, Unk 07, EVX2, SEPT9, SOX1, Unk 19, Unk 21, SOX17, GALR1, TBX15, EEF1A2, DMRTA2, and TFAP2B (as indicated in Table 1A).

In certain aspects, the patient has been previously treated for or diagnosed with bladder cancer. In some aspects, the method is further defined as a method for detecting bladder cancer recurrence or a risk of bladder cancer recurrence.

In other aspects, said determining comprises analyzing DNA methylation in the sample using restriction endonuclease digestion and qPCR. In further aspects, the digestion reaction is completed in a first step, followed by the qPCR reaction in a second step.

In some aspects, the patient is a human. In certain aspects, the sample is a urine sample. In other aspects, the sample is a blood sample. In further aspects, the sample is obtained by drawing blood from the patient. In other aspects, the sample is obtained from a third party.

In certain aspects, determining a methylation status comprises determining the nucleotide positions in the genomic regions that comprise methylation. In some aspects, determining a methylation status comprises determining the proportion of methylation at nucleotide positions in the genomic region. In further aspects, determining a methylation status comprises determining the proportion of nucleotide positions that are methylated in the genomic region.

In some aspects, the reference level is a level of methylation from a patient that does not have bladder cancer. In certain aspects, the method is further defined as a method for determining the severity of bladder cancer.

In a further embodiment, the invention provides a method of detecting the presence of, or an increased risk of, bladder cancer in a patient comprising obtaining a patient sample, determining a methylation status in one or more genomic regions selected from those in Table 1, and identifying the presence of, or an increased risk of, bladder cancer in the patient based on an increased level of methylation in one or more of the genomic regions relative to a reference level.

In yet a further embodiment, the invention provides a method for treating a patient having bladder cancer or at risk for having bladder cancer comprising administering a therapy to the patient, wherein the patient was previously determined to have an increased level of methylation in one or more of the genomic regions selected from those provided in Table 1 relative to a reference level. In some aspects, the therapy comprises administering an anti-cancer therapy to the subject. In further aspects, the anti-cancer therapy is chemotherapy, radiotherapy, gene therapy, surgery, hormonal therapy, anti-angiogenic therapy or cytokine therapy. In certain aspects, the anti-cancer therapy is a BCG therapy.

In still a further embodiment, the invention provides kits for analysis of DNA methylation. In some aspects, a kit is provided comprising a sealed container comprising primers or probes designed to detect methylation in one, two, three, four, five, six, seven, eight, nine, ten, eleven, twelve, thirteen, fourteen, fifteen, sixteen or more genomic regions of Table 1A. For example, a kit may comprise a primer pair for amplification of an interval of sequence in one of the genomic regions of Table 1 and a reagent for analysis of DNA methylation (e.g., a methylation sensitive restriction endonuclease). In a further aspect, a kit may comprise reagents for analysis of total DNA methylation levels.

In a further aspect, kits are provided for determining one or more methylation positions in a DNA sample. For example, a kit can comprise, at least, an active glucosyltransferase and a DNA endonuclease (e.g., MspI, TaqI or a methylation dependent DNA endonuclease, such as BisI, GlaI or McrBC). Kits according to the invention can further comprise one or more MSEs; a DNA methyltransferase (e.g., M.SssI and/or M.CviPI methyltransferase); an enzyme that converts 5'mC into 5'hmC (e.g., recombinant Tet1, Tet2 and/o Tet3 proteins); one or more reference DNA samples; an affinity purification column; a DNA ligase; a DNA polymerase; DNA sequencing reagents; a PCR buffer; instructions; methylation specific antibodies; and/or DNA primers (also reagents to determine general urine parameters (pH, amount of hemoglobin, leukocytes, e.g. Osumex 10P test kit, Uriscan (YD Diagnostic Corp.).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4-8: Relative methylation values after restriction endonuclease digestion and Real-Time qPCR. Y axis represents the methylation level relative to the undigested blood DNA value (Blood −); this is the reference sample which value=1. −=undigested template; +=digested template. Blood=Genomic DNA extracted from blood (healthy male, 53 yo); LD583=Genomic DNA extracted from a bladder cancer cell line; Urine=Genomic DNA extracted from urine of non-bladder cancer human.

FIG. 9: Example of typical results after qPCR using POLR2A primers (loading control marker) and undigested/digested gDNAs as template (three different sample types). 15 ng of DNA was used for each reaction. CT values are indicated.

FIG. 10: Methylation percentages for 16 different markers (categories A and B in Table 3) in digested clinical sample. nnU=normal Urine. Values higher than 1% are marked in red, while values >0.25% and <1% are marked in blue. Red arrows and circles indicate markers for those where a higher background in nnU was observed.

FIG. 11: The samples of FIG. 10 were classified into three categories on the basis of the % of signal in different markers: samples that show cancer presence/development are marked in red (values higher than 1% in multiple markers); borderline samples, with multiple low-confidence positive values (>0.5% and <1%) are marked in orange; samples with values <0.5% for all the marker are considered cancer free and are marked in green.

FIGS. 18A-18C: Description of an exemplary CARE assay Kit and reaction. A) Fundamental CARE assay Kit components; other components like Multistix® 10 SG Reagent Strips, UCBTM and urine collection container might be included in the final kit. To note, a single D and U Reaction Mixes are represented in the figure (enough for one marker set); more Reaction Mixes should be included in the kit if more marker sets will be used. B) DNA sample isolated from urine sample is diluted to the appropriate concentration using DNA Diluent Buffer. C) Reactions are assembled: 15 μl of U and D Reaction Mixes are distributed into a 96-well plate and mixed with 5 μl of E.D.C. or DNA sample/s. After digestion and qPCR steps CARE markers methylation is calculated. In the figure, two technical replicates for each reaction are performed.

FIGS. 19A-19F: Algorithm used to calculate the methylation percentage of markers belonging to CARE assay set A in two different sample (Spl 01 and 02) and in the external digestion control (E.D.C.). Mean CT values (CTm) are collected (A) and ΔCT (B), ΔΔCT (C) and RQ (D) values are calculated by the CFX96TM-Real Time System Machine. Data are then expressed in percentage, considering the RQ value for each single marker in each undigested sample equal to 100% (E). In the example above the analysis can be considered valid since the methylation level of the endogenous digestion control GAPDH (grey circles) and of all the markers in the exogenous digestion control E.D.C. (black circle) are below the maximum acceptable background limit (1%) in the digested samples (+). (F) Accordingly to the data obtained Spl 01 is negative for bladder cancer, while Spl 02 is positive. Experiment was performed using three technical replicates. Results might also be expressed in corrected DNA copy number resistant to digestion instead of percentage.

FIG. 23: Exemplary depiction of 96-well assay plate set-up for MMSP assay including methylation standard samples S1-S7, methylation controls (MC) and no template control (NC).

FIGS. 27A-27B: Analysis of bladder cancer recurrence using group B markers and MMSP assay.

FIG. 28: Table reflecting sensitivities and specificities of urine tumor markers in bladder cancer.

DESCRIPTION OF ILLUSTRATIVE EMBODIMENTS

Figure 1:
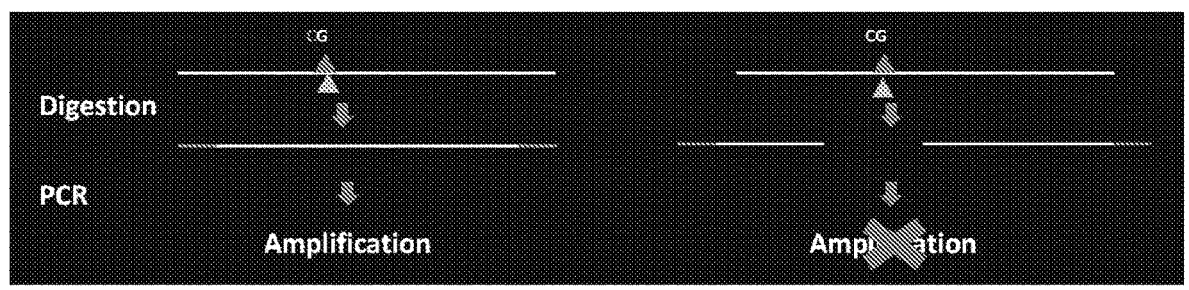
FIG. 1A-B: (A) Schematic of methylation analysis system. (B) List of restriction enzymes with their corresponding digestion site. The enzyme will cut the CG-containing sequence only is the C (shown enlarged) is not methylated.

I. The Embodiments of the Present Invention

The methylome of cancer cells greatly differ from that of normal cells. In general, cancer cells show an increase in CpG islands methylation, while other genomic elements, including transposons, lose their normal methylated status. Thus it is possible to detect the presence of cancer cells in a cell population through the analysis of the methylation status of CpG elements that are specifically methylated in cancer cells. Provided herein are multiplex methods for determining a genomic methylation profile in a subject. These new techniques allow for highly quantitative and rapid methods for determine the methylation profile from patient samples. These profiles can, in turn, be used to determine disease risk in patients. For example, methylation profiles can be used on their own or in conjunction with other diagnostic tests to determine if a patient has a cancer or to assess the aggressiveness of a cancer. Moreover, methylation profiles can be used to select the most effective therapy for a subject having a disease. For example, the profiles can be used to determine whether a cancer is likely to respond to a given chemotherapeutic agent or if surgical removal of cancer cells is likely to provide an effective treatment and prevent recurrence.

In some aspects, the inventors identify a panel of methylation markers (e.g., genomic regions) that can be assessed for methylation status to determine whether a subject has, or is at risk for development of, a bladder cancer. Briefly, cancer specific methylation markers were identified by analyzing tissue and or other cancers of the urinary tract (i.e. detected from cells present in the urine or urine sediment or alternately from normal sample biopsy) samples from patients with bladder cancer using the HM450 human methylation array and RRBS next-generation sequencing. A linear regression model was utilized to select the most significant methylation biomarkers which separated tumor and normal samples (FIG. 14A-E). Genomic regions (and specific potential methylation positions) that may be assessed by a method of the embodiments are listed below in Table 1A. Example primer and probe sets for real-time qPCR assays, such as the MMSP assay and CARE assay are shown in Tables 1B and 1C (respectively).

TABLE 1A

| Code | Genomic region | Preferred methylation site |
| --- | --- | --- |
| 01 | OTX1 | Chr2, m5C position 63281139 |
| 02 | ZIC4 | Chr3, m5C position 147111660 |
| 03 | PCDHGA4 | Chr5, m5C position 140811642 |

TABLE 1A-continued

| Code | Genomic region | Preferred methylation site |
|---|---|---|
| 04 | TFAP2B | Chr6, m5C position 50791202 |
| 05 | Unknown (Unk) 05 | Chr7, m5C position 149112318 |
| 06 | SCT | Chr11, m5C position 627152 |
| 07 | Unk 07 | Chr17, m5C position 5001047 |
| 08 | GALR1 | Chr18, m5C position 74962133 |
| 09 | Unk 09 | Chr21, m5C position 38065524 |
| 10 | DMRTA2 | Chr1, m5C position 50886782 |
| 11 | SIX3 | Chr2, m5C position 45171818 |
| 12 | C1ORF70 | Chr1, m5C position 1475742 |
| 13 | Unk 13 | Chr2, m5C position 130971164 |
| 14 | Unk 14 | Chr1, position 63785946 |
| 15 | GALR1 | Chr18, m5C position 74962369 |
| 16 | SEPT9 | Chr17, m5C position 75368902 |
| 17 | FZD7 | Chr2, m5C position 202900063 |
| 18 | DCHS2 | Chr4, m5C position 155411603 |
| 19 | Unk 19 | Chr13, m5C position 53775108 (Near PCDH8) |
| 20 | KCNA3 | Chr1, m5C position 111217194 |
| 21 | Unk 21 | Chr4, m5C position 1400189 |
| 22 | DPM2* | Chr9, m5C position 130700954 (Methylated in blood) |
| 23 | TBX15 | Chr1, m5C position 119522459 |
| 24 | Unk 24 | Chr10, m5C position 103044008 |
| 25 | CCDC81 | Chr11, m5C position 86085790 |
| 26 | KCNA6 | Chr12, m5C position 4918900 |
| 27 | SOX1 | Chr13, m5C position 112721950 |
| 28 | Unk 28 | Chr18, m5C position 45968115 |
| 29 | Unk 29 | Chr2, m5C position 118593895 |
| 30 | EVX2 | Chr2, m5C position 176947173 |
| 31 | CERKL | Chr2, m5C position 182543251 |
| 32 | EEF1A2 | Chr20, m5C position 62119669 |
| 33 | POU4F2 | Chr4, m5C position 147561722 |
| 34 | SHH | Chr7, m5C position 155597779 |
| 35 | Unk 35 | Chr7, m5C position 24323317 (Near NPY gene) |
| 36 | SOX17 | Chr8, m5C position 55370529 |
| 37 | Unk 37 | Chr9, m5C position 70921347 |
| 38 | HOXA9 | Chr2, m5C position 176987413 |
| 39 | NPY | Chr7, m5C position 24323817 |
| 40 | IRAK3 | Chr12, m5C position 66583004 |
| 41 | TJP2 | Chr9, m5C position 71736214 |

*indicates a non-cancer marker that is methylated in blood.

TABLE 1B

Example primer and probe sets for a MMSP assay.

| Region | Forward | Reverse | Probe |
|---|---|---|---|
| OTX1 (#01) | TCGCGGAAG TAGCGGC (SEQ ID NO: 1) | CACCTCCTCC CGCATAAAAA (SEQ ID NO: 2) | AACGCCTCGAA CACGTCCAACT ATAAACG (SEQ ID NO: 3) |
| TFAP2B (#04) | GGAGGGATTATT ATTCGGTTCGT (SEQ ID NO: 4) | CCATACCCG CGTCCAAAC (SEQ ID NO: 5) | ATACGCCGAAT ACAACAACACG TCCGA (SEQ ID NO: 6) |
| Unk05 | TCGTACGTAAGT CGCGTATAGTAT TGT (SEQ ID NO: 7) | AATCCGAAC TAACCGCCG (SEQ ID NO: 8) | CGCCGCCCA AAACGCGA (SEQ ID NO: 9) |
| Unk07 | AGGTAAGAGT TTCGGCGGC (SEQ ID NO: 10) | CCTCAACCCT CGAACCCAAC (SEQ ID NO: 11) | TCGCGACAAACA CGCTTCCGCCTA (SEQ ID NO: 12) |
| GALR1A (#08) | TCGGCGAAG ATTTGGAGC (SEQ ID NO: 13) | CGCGACCACG AAACCTAAA (SEQ ID NO: 14) | TTTTATTTGCGCG GTTGTAGTCGGC (SEQ ID NO: 15) |
| Unk09 | CGCGTAAAAG GTAGGATCGC (SEQ ID NO: 16) | AACTCGAAACT CTACCCCCGA (SEQ ID NO: 17) | AACGCCGACTC AACAAAAAATT ATTTCGAA (SEQ ID NO: 18) |
| DMRTA2 (#10) | AGCGATAGTAGC GTTTGTGGTTT (SEQ ID NO: 19) | GCGAACCCC CAAATACG (SEQ ID NO: 20) | TCGCAACCATA ACGTAATATCG ACCCTCA (SEQ ID NO: 21) |
| SEPT9 (#16) | GTTTTTGAGTTTA TAGGTCGGGATTT (SEQ ID NO: 22) | CTATCACC GCCGCCG (SEQ ID NO: 23) | AAATTAAACGAC AACGCACGCG ACTAACAA (SEQ ID NO: 24) |
| DCHS2 (#18) | AGCGGTGACG GTAGTGGTTT (SEQ ID NO: 25) | CTACACCCTAAT ACAACCGTCCG (SEQ ID NO: 26) | AACCCGTTCTT CCAATTACGC TACCGAA (SEQ ID NO: 27) |
| Unk19 | GCGGACGTTA GTTAGTCGGC (SEQ ID NO: 28) | CCCGAATCCC TATCCGAAA (SEQ ID NO: 29) | CGCCCACTCCG ACACCAACGT (SEQ ID NO: 30) |
| Unk21 | CGCGTTTAAT TGGTTGCGA (SEQ ID NO: 31) | TATCTATTCG TCCCGCCCG (SEQ ID NO: 32) | AAATCCGCCTCC TCGACCCGAAA (SEQ ID NO: 33) |
| TBX15 (#23) | GGTTGGTATAT CGAGGTTTCGT AGTT (SEQ ID NO: 34) | CGCGTCTA CCCGCCC (SEQ ID NO: 35) | AAACGACGAA CGAATCAAAC GCGACT (SEQ ID NO: 36) |
| SOX1 (#27) | GGTATTTGGGA TTAGTATATGT TTAGCGT (SEQ ID NO: 37) | CCTCAACGAC CTCCAACTCG (SEQ ID NO: 38) | ACTACAACTTC TAACAAAACGA CGCGCCG (SEQ ID NO: 39) |
| EVX2 (#30) | GATTCGCGTTAG AGTCGGAGTTA (SEQ ID NO: 40) | CGTCGAACTCA AACCTCGAAA (SEQ ID NO: 41) | CGTCGCGTT TTCGTCGT (SEQ ID NO: 42) |
| EEF1A 2(#32) | GCGTATACGG TTTTGGGGTC (SEQ ID NO: 43) | CAAACTTCC GCGCCCAAC (SEQ ID NO: 44) | CTCGCCACGCT CAATACCCGTT TTACC (SEQ ID NO: 45) |
| SOX17 (#36) | GGACGTGGGA TTCGGATTAC (SEQ ID NO: 46) | TTTTCTACACA AATATAACCA ATAAAACGAC (SEQ ID NO: 47) | CGAACCGATCC CGCGTCGTTAA (SEQ ID NO: 48) |

TABLE 1C

Example primer and probe sets for a CARE assay.

| Locus | Primer Forward | Primer Reverse | Probe |
|---|---|---|---|
| POLR2A | ACCTACCTCTC CAAGCTATTC (SEQ ID NO: 49) | GGTGTAATTGG GACTGGTTGG (SEQ ID NO: 50) | TACTCACCCACC AGCCCGAACTA (SEQ ID NO: 51) |
| GAPDH | CGTAGCTCAG GCCTCAAGAC (SEQ ID NO: 52) | GAGGAGCAGA GAGCGAAGC (SEQ ID NO: 53) | CTCAGCCAGTC CCAGCCCAAG (SEQ ID NO: 54) |
| SOX1 (#27) | CCACGACTGC ACCTGTTTGC (SEQ ID NO: 55) | GGCAGAAACA CACGCACTCG (SEQ ID NO: 56) | TCGGCCTCTTTG GCAAGTGGTTT (SEQ ID NO: 57) |
| GALR1 (#15) | ACCCACCCTC TCTCAGAAGG (SEQ ID NO: 58) | AGTTTAGGAGT CTGAGCTTCC (SEQ ID NO: 59) | CGCAAAGACGG TGCCACCAGG (SEQ ID NO: 60) |
| DMRT A2b (#10) | GCAGTGCCGT AGAGCAGCT (SEQ ID NO: 61) | CCCTCAAGGGC CACAAACGCTA (SEQ ID NO: 62) | CACAGGCAGTCC TTCCAGCGACAG (SEQ ID NO: 63) |
| Unk05 (#05) | CACTCACGTCT TCGTAGTCAG (SEQ ID NO: 64) | TTGGAGTGTGA CGGTAAAAGC (SEQ ID NO: 65) | CGTACAGCACT GCAGGGTCCG (SEQ ID NO: 66) |
| Unk07 (#07) | GGGAGGACCC CTCGTTAGC (SEQ ID NO: 67) | CTCAGCGTCC GACCCCACT (SEQ ID NO: 68) | TGGGCTCGAG GGCTGAGGGC (SEQ ID NO: 69) |
| EVX2 (#30) | AGGCTTCCGA GGCCTGAGC (SEQ ID NO: 70) | AGCGACTCTC CTTCCTGACG (SEQ ID NO: 71) | CGTACCCTGGCA AACAAACGACC (SEQ ID NO: 72) |
| SOX17 (#36) | TGGGCGTGGG CCTAACGAC (SEQ ID NO: 73) | CCCGTGTTCT GGCCTGTCG (SEQ ID NO: 74) | TGGGTACGCTG TAGACCAGACC (SEQ ID NO: 75) |
| DCHS2 (#18) | CGCACGCGA CAGACCTCG (SEQ ID NO: 76) | TGGATGAGAA CGACAACCCG (SEQ ID NO: 77) | CGGTACTCGTCC TGCTCAAAGAC (SEQ ID NO: 78) |
| Unk09 (#09) | ACCGAGGCC CCTACCTGG (SEQ ID NO: 79) | GTTAGAAACG CAGGCCAGGC (SEQ ID NO: 80) | CACTGAACGAC CCCTTCTCCAG (SEQ ID NO: 81) |
| EEF1A2 (#32) | GCCGACTTGG TGACCTTGC (SEQ ID NO: 82) | GGCCAGAGCC CTGGGGTTG (SEQ ID NO: 83) | CCACGTTCTTGA TGACGCCTACG (SEQ ID NO: 84) |
| Unk19 (#19) | GACGTGGTGTT CGCTTTTGGC (SEQ ID NO: 85) | CGCACGTGCA GCTCGTAGG (SEQ ID NO: 86) | CCCGTGGATTAC CAGAGTCAGGA (SEQ ID NO: 87) |
| Unk21 (#21) | ACACGCCGAA CACACGTGC (SEQ ID NO: 88) | CCGTCCGTGT GTCCTGTGC (SEQ ID NO: 89) | CCTAATTGGCT GCGAACGGTCC (SEQ ID NO: 90) |

In particular, the inventors have used a unique methylation marker panel, along with controls and methylation sensitive restriction enzymes to generate a novel reaction design that allows multiplex digestion and qPCR reaction in the same buffer to detect the methylation at specific CpG dinucleotides. In certain aspects, this method may be preferred as it has a great advantage in allowing for the analysis of CpG methylation without threating the DNA with sodium bisulfite at high temperature (a reaction that strongly impact the DNA sequence and reduce the quality of DNA for downstream experiments).

II. Reagents and Kits

The kits may comprise suitably aliquoted reagents of the present invention, such as a glucosyltransferase (e.g., a β-glucosyltransferase) and one or more Methylation-Sensitive DNA endonucleases (e.g., MspI, ClaI, Csp6I, HaeIII, TaqI, MboI, or McrBC) or a methylation dependent endonuclease such as BisI, GlaI or McrBC. Additional components that may be included in a kit according to the invention include, but are not limited to, MSEs (e.g., AatII, AccIII, AciI, AfaI, AgeI, AhaII, Alw26I, Alw44I, ApaLI, ApyI, AscI, Asp718I, AvaI, AvaII, Bme216I, BsaAI, BsaHI, BscFI, BsiMI, BsmAI, BsiEI, BsiWI, BsoFI, Bsp105I, Bsp119I, BspDI, BspEI, BspHI, BspKT6I, BspMII, BspRI, BspT104I, BsrFI, BssHII, BstBI, BstEIII, BstUI, BsuFI, BsuRI, CacI, CboI, CbrI, CceI, Cfr10I, ClaI, Csp68KII, Csp451, CtyI, CviAI, CviSIII, DpnII, EagI, Ec136II, Eco47I, Eco47III, EcoRII, EcoT22I, EheI, Esp3I, Fnu4HI, FseI, FspI, Fsp4HI, GsaI, HaeII, HaeIII, HgaI, HhaI, HinPII, HpaII, HpyAIII, HpyCH41V, ItaI, KasI, Kpn21, LlaAI, LlaKR2I, MboI, MflI, MluI, MmeII, MroI, MspI, MstII, MthTI, NaeI, NarI, NciAI, NdeII, NgoMIV, NgoPII, NgoS II, NlaIII, NlaIV, NotI, NruI, NspV PmeI, PmlI, Psp1406I, PvuI, RalF40I, RsaI, RspXI, RsrII, SacII, SalI, Sau3AI, SexAI, SfoI, SfuI, SmaI, SnaBI, SolI, SpoI, SspRFI, Sth368I, TaiI, TaqI, TflI, TthHB8I, VpaK11BI, or XhoI), oligonucleotide primers, reference DNA samples (e.g., methylated and non-methylated reference samples), distilled water, probes, a PCR buffer, dyes, sample vials, polymerase, ligase and instructions for performing methylation assays. In certain further aspects, reagents for DNA isolation, DNA purification and/or DNA clean-up, analysis of urine clinical parameters, may also be included in a kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing reagent containers in close confinement for commercial sale. Such containers may include cardboard containers or injection or blow-molded plastic containers into which the desired vials are retained.

When the components of the kit are provided in one or more liquid solutions, the liquid solution is an aqueous solution, with a sterile aqueous solution being preferred.

However, the components of the kit may be provided as dried powder(s). When reagents and/or components are provided as a dry powder, the powder can be reconstituted by the addition of a suitable solvent. It is envisioned that the solvent may also be provided in another container means.

In some aspects, labeled probes may be used to detect and/or quantify PCR amplification. Numerous reporter molecules that may be used to label nucleic acids probes are known. Direct reporter molecules include fluorophores, chromophores, and radiophores. Non-limiting examples of fluorophores include, a red fluorescent squaraine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e]indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor™ dyes, AMCA, BODIPY™ 630/650, BODIPY™ 650/665, BODIPYTh-FL, BODIPY™-R6G, BODIPY™-TMR, BODIPY™-TRX, Cascade Blue™, CyDye™, including but not limited to Cy2™, Cy3™, and Cy5™, a DNA intercalating dye, 6-FAM™, Fluorescein, HEX™, 6-JOE, Oregon Green™ 488, Oregon Green™ 500, Oregon Green™ 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red™. A signal amplification reagent, such as tyramide (PerkinElmer), may be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, may also be employed.

III. Definitions

As used herein, a "methylation sensitive restriction endonuclease" (MSRE) is a restriction endonuclease that includes CG as part of its recognition site and has altered activity when the C is methylated as compared to when the C is not methylated (e.g., SmaI). Non-limiting examples of methylation sensitive restriction endonucleases include HpaII, BssHII, BstUI, SacII, EagI and NotI. An "isoschizomer" of a methylation sensitive restriction endonuclease is a restriction endonuclease that recognizes the same recognition site as a methylation sensitive restriction endonuclease but cleaves both methylated CGs and unmethylated CGs, such as for example, MspI is an isoschizomer of HpaII. "Restriction endonuclease" and "restriction enzyme" are used interchangeably herein.

As used herein the term "genomic region" refers to a region of genomic DNA encoding and controlling expression of a particular RNA or polypeptide (such as sequences coding for exons, intervening introns and associated expression control sequences) and its flanking sequence or other genomic regions of interest (e.g. repetitive elements or repeated regions of genomic DNA such as dispersed or interspersed retroelements, SINES; LINES; among other such elements). Thus, in some aspects, a genomic region is defined by the regions encoding the genomic regions listed in Table 1. It is, however, recognized in the art that methylation in a particular region (e.g., at a given CpG position or in an amplification interval) is generally indicative of the methylation status at proximal genomic sites. This is particularly true for regulatory elements like CpG islands. Accordingly, determining a methylation status of a particular genomic region can comprise determining a methylation status at a site or sites within about 100, 50, or 25 kb of a named genomic region. Thus, in some aspects, assessing methylation in genomic regions, such as those of Table 1 comprises assessing the methylation at one or more potential sites of methylation with-in 100, 50, or 25 kb (or preferably with 10 kb) of a potential methylation position listed in Table 1.

As used herein the term "genomic amplification interval" refers to a region of genomic DNA that can be amplified by PCR. As used herein an amplification interval comprises at least one CpG position that is a potential site of methylation. In some cases, the amplification interval comprises 2, 3, 4 or more potential sites of CpG methylation (e.g., wherein the CpG is in a sequence recognized by an MSE). In general an amplification interval is less than about 1,200 bp, such as between about 50 bp and 100, 200, 300, 400 or 500 bp. In certain aspects, the amplification interval is 130 bp or less.

As used herein "determining a methylation status" for an indicated genomic region means determining whether one of more position in the DNA of the genomic region is methylated. Thus, in certain aspects, determining a methylation status for a genomic region comprises determining the methylation status of at least 1, 2, 3, 4, 5, 6, 7, 8, 9, 10, 15, 20, 25, 30, 35, 40, 45, 50 or more sites of potential DNA methylation. In other aspects determining a methylation status means determining the methylation status of one or more methylated sites in a differential methylated region (DMR, e.g. in a window of about 1-10 bp, 10-100 bp, 100-200 bp, 100-1,000, bp or larger window)

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Analysis of Methylation Using Restriction Endonuclease Digestion and Real-Time PCR The analysis system is based on the principle that some restriction enzymes can cut sequences containing CG dinucleotides only if the C is not methylated (FIG. 1A-B).

Marker Design—

A group of 39 genomic regions (see Table 1 below) were identified to be methylated in bladder cancer and selected for further analysis. Many of the selected markers are not yet annotated (i.e., the gene associated to the CpG island is not known yet; named Unknown (Unk) #). Several control regions are included in Table 2 below. The LINE-1 controls were designed by the inventors and are highly methylated in normal tissues and less in cancer. The GAPDH control was designed by the inventors to serve as a determination of digestion efficiency. Its CpG island is not methylated in all normal and cancer tissues. The POLR2A control marker was designed by the inventors as well and it does not contains any restriction site, so it is a copy number control (for the determination of the amount of template used in each reaction) Other LINE-1 controls could be used as a copy number control (the amplicon does not contains any restriction site). This control will amplify about 16,500 copies of LINE-1 elements in the human genome, circumventing the problem that a deletion affecting a single-copy copy number control will impair the analysis. The usage of LINE-1 as a copy number marker is not yet confirmed and the inventors have used the POLR2A control.

TABLE 2

Genomic regions with methylation at specific CG sites in bladder cancer samples (tissue, urine and cell lines). Regions 22, 42, and 43 are methylation control regions.

| Code | Genomic region | methylation site |
|---|---|---|
| 01 | OTX1 | Chr2, m5C position 63281139 |
| 02 | ZIC4 | Chr3, m5C position 147111660 |
| 03 | PCDHGA4 | Chr5, m5C position 140811642 |
| 04 | TFAP2B | Chr6, m5C position 50791202 |
| 05 | Unk 05 | Chr7, m5C position 149112318 |
| 06 | SCT | Chr11, m5C position 627152 |
| 07 | Unk 07 | Chr17, m5C position 5001047 |
| 08 | GALR1 | Chr18, m5C position 74962133 |
| 09 | Unk 09 | Chr21, m5C position 38065524 |
| 10 | DMRTA2 | Chr1, m5C position 50886782 |
| 11 | SIX3 | Chr2, m5C position 45171818 |
| 12 | C1ORF70 | Chr1, m5C position 1475742 |
| 13 | Unk 13 | Chr2, m5C position 130971164 |
| 14 | Unk 14 | Chr1, position 63785946 |
| 15 | GALR1 | Chr18, m5C position 74962369 |
| 16 | SEPT9 | Chr17, m5C position 75368902 |
| 17 | FZD7 | Chr2, m5C position 202900063 |
| 18 | DCHS2 | Chr4, m5C position 155411603 |
| 19 | Unk 19 | Chr13, m5C position 53775108 (Near PCDH8) |
| 20 | KCNA3 | Chr1, m5C position 111217194 |
| 21 | Unk 21 | Chr4, m5C position 1400189 |
| 22 | DPM2* | Chr9, m5C position 130700954 * hypermeth in blood |
| 23 | TBX15 | Chr1, m5C position 119522459 |
| 24 | Unk 24 | Chr10, m5C position 103044008 |
| 25 | CCDC81 | Chr11, m5C position 86085790 |
| 26 | KCNA6 | Chr12, m5C position 4918900 |
| 27 | SOX1 | Chr13, m5C position 112721950 |
| 28 | Unk 28 | Chr18, m5C position 45968115 |
| 29 | Unk 29 | Chr2, m5C position 118593895 |
| 30 | EVX2 | Chr2, m5C position 176947173 |
| 31 | CERKL | Chr2, m5C position 182543251 |
| 32 | EEF1A2 | Chr20, m5C position 62119669 |
| 33 | POU4F2 | Chr4, m5C position 147561722 |
| 34 | SHH | Chr7, m5C position 155597779 |
| 35 | Unk 35 | Chr7, m5C position 24323317 (Near NPY gene) |
| 36 | SOX17 | Chr8, m5C position 55370529 |
| 37 | Unk 37 | Chr9, m5C position 70921347 |
| 38 | HOXA9 | Chr2, m5C position 176987413 |
| 39 | NPY | Chr7, m5C position 24323817 |
| 40 | IRAK3 | Chr12, m5C position 66583004 |
| 41 | TJP2 | Chr9, m5C position 71736214 |
| 42 | LINE-1 5' | Chr2, m5C position 66617179 (44Kb upstr MEIS1 gene) |
| 43 | LINE-1 body | Chr2, m5C position 66618707 (44Kb upstr MEIS1 gene) |
| 44 | GAPDH | Chr12, m5C position 6643629 |
| 45 | POLR2A | Within exon 29 of RNA Polymerase II subunit A gene |

*Marker # 22 is methylated in blood but not in bladder cancer; in preferred aspects the GALR1 (#15) marker was used instead of GALR1 (#08).
GAPDH = digestion control; contains several restriction sites; always unmethylated.
POLRA = copy number control; does not contains any restriction site (not sensitive to digestion).

Msre Qpcr Design—

Four different methylation sensitive restriction endonucleases were selected (AciI, HpyCH4IV, HinP1I and HpaII) Each restriction endonuclease is a four-base cutter that is able to cut the restriction site only if the cytosine in the targeted CpG dinucleotide is unmethylated. All the amplicons (including the primer sequences) were designed in order to contain one or more recognition sites for at least three out of four different restriction endonucleases. This ensures a high digestion reliability (multiple restriction sites within the same amplicon are targeted but it is sufficient that just one site is cut to impair the DNA amplification in the next step) and reduce the possibility that small changes in the DNA sequence (e.g. SNPs) can result in false positive.

Moreover, the amplicon length range is 70 to 158 bp and all the primers were designed and verified to have efficiencies between 90 and 110% and an annealing temperature of 60° C. These are prerequisites for qPCR data reliability and for the standardization of the qPCR condition.

Digestion Conditions—

All the restriction endonucleases were purchased from New England Biolabs and mixed together resulting in a stock solution in which the final concentration for each enzyme was 2.5 U/µl. The digestion reaction solutions were prepared as follows: CutSmart 1×, Endonuclease-MIX 0.125 U/µl, Template 5 or 2.5 ng/µl; $MgCl_2$ 4 mM (Stock solution: 20 mM $MgCl_2$ in 10 mM Tris-HCl pH 7.5; increasing $Mg^{2+}$ concentration will increase the digestion efficiency even if the reaction contains 0.1 mM EDTA). The final template concentration was 5 ng/µl. Digestions were incubated overnight (16 h) at 30° C. in a thermocycler machine, after that enzymes were inactivated by heating the reactions at 800 for 5'. It was previously determined by the inventors that 30° C. is the optimal working temperature for all 4 enzymes (AciI loses a substantial percentage of its activity over time at 37° C. but not at 30°). A parallel negative reaction (with no enzymes) was also conducted.

qPCR Reaction Conditions—

Figure 12:
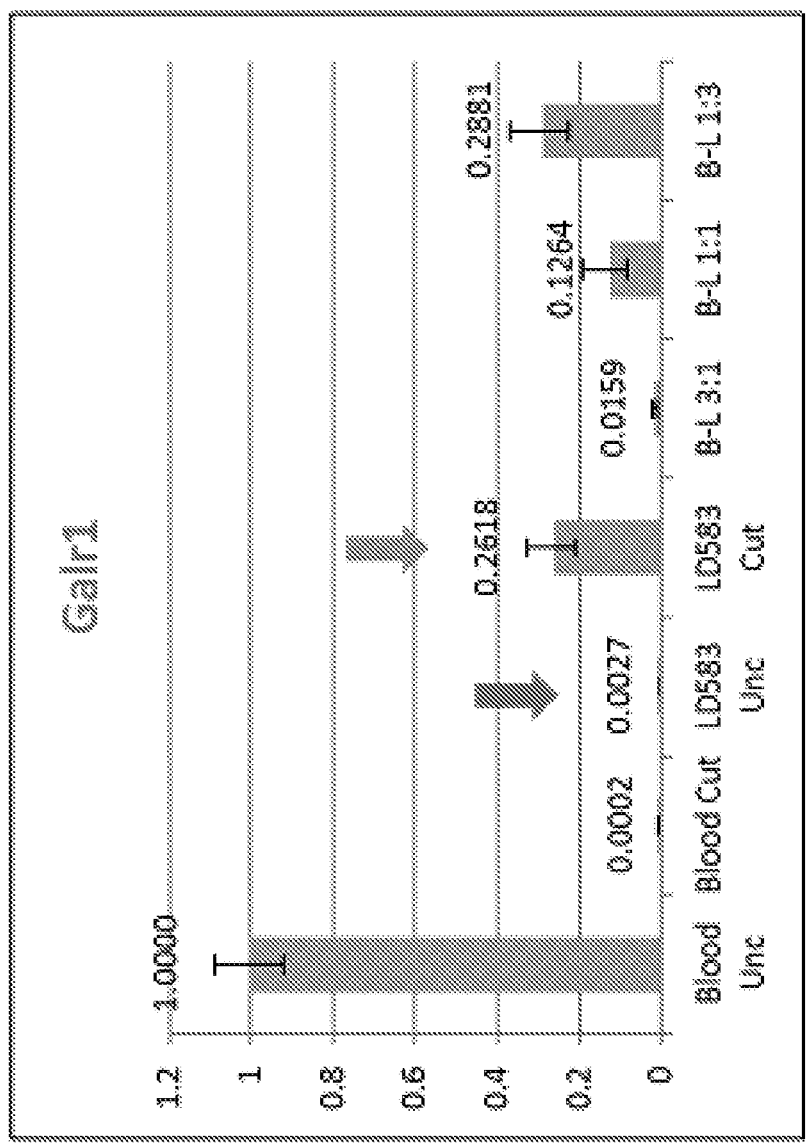
FIG. 12: Preliminary qPCR reaction results for marker GALR1. LD583 is a bladder cancer cell line and the marker GALR1 is methylated in this line, but not in blood (450K data). The undigested LD583 sample (indicated by the red arrow) is not amplifying at all and the digested LD583 sample (green arrow) show an amplification, but much weaker than that in the undigested blood DNA control (first bar). The amount of template used for Blood and LD583 is for both 10 ng and the POLR2A marker amplification is comparable between the two samples. This problem was circumvented by adding 5% DMSO (final concentration) to the PCR reaction.

The Real Time reactions were performed using the Bio-Rad CFX machine. Preliminary trials demonstrate that the complete denaturation of the template is a critical step for the qPCR reactions. This is particularly true for methylated CpG-rich templates that are slightly more difficult to denaturate compared to the non-methylated DNA (e.g. see FIG. 12). This problem (which magnitude is different for different markers See FIG. 12) was resolved by adding to the qPCR reaction a final concentration of 5% DMSO and increasing the denaturation temperature from 95° C. to 97° C. (It was observed that this is the highest temperature that will not decrease the ZymoTaq™ activity).

Figure 2:
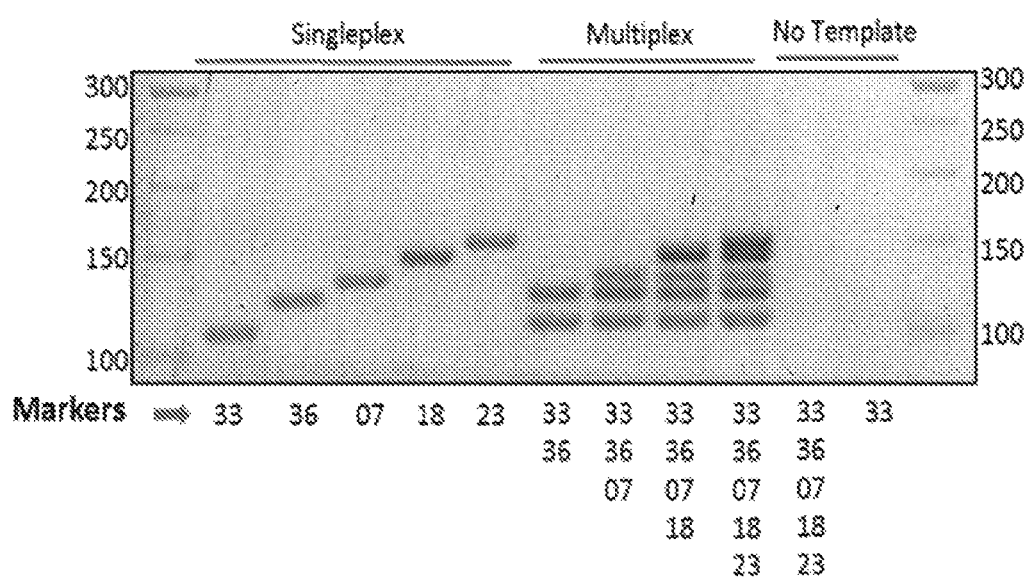
FIG. 2: Multiplex vs Singleplex qPCR reactions; 7.5 µl of PCR reaction (sub-complete amplification; 35 cycles) were loaded for each lane; undigested Blood gDNA was used as template. The numbers below each well correspond to the marker numbers in Table 1.

The inventors also verified the possibility to perform a multiplex reaction without decreasing the amplification efficiency. FIG. 2 shows that it is possible to multiplexing up to 5 markers in the same reaction without affecting the overall PCR efficiency (note the intensity of the single marker bands in singleplex—left side of the gel—compared to the band intensities when the reactions were performed in multiplex).

The PCR Reaction solutions were prepared according to the following formula: ZymoTaq PreMix (2×), 10 µl; primer FW, 0.4 µM (final concentration); primer RV, 0.4 M (final concentration); template, 10 ng (2 µl of digestion reaction); DMSO, 5% (final concentration); and ddWater to 20 µl. Reactions were amplified on a CFX BioRad qPCR machine with the thermal profile: 97° C. for 2 minutes; then forty-five cycles of 95° C. for 20 seconds, 60° C. for 30 seconds, and a final extension at 72° C. for 1 minute (new conditions are 60° C. for one minute avoiding the elongation step at 72° C.). All amplifications were then subjected to melt curve analysis with fluorescence measurements to ensure specific amplification and identity. The melt curve was 60° C. to 97° C. The amplicons were then stored at 15° C.

Figure 3:
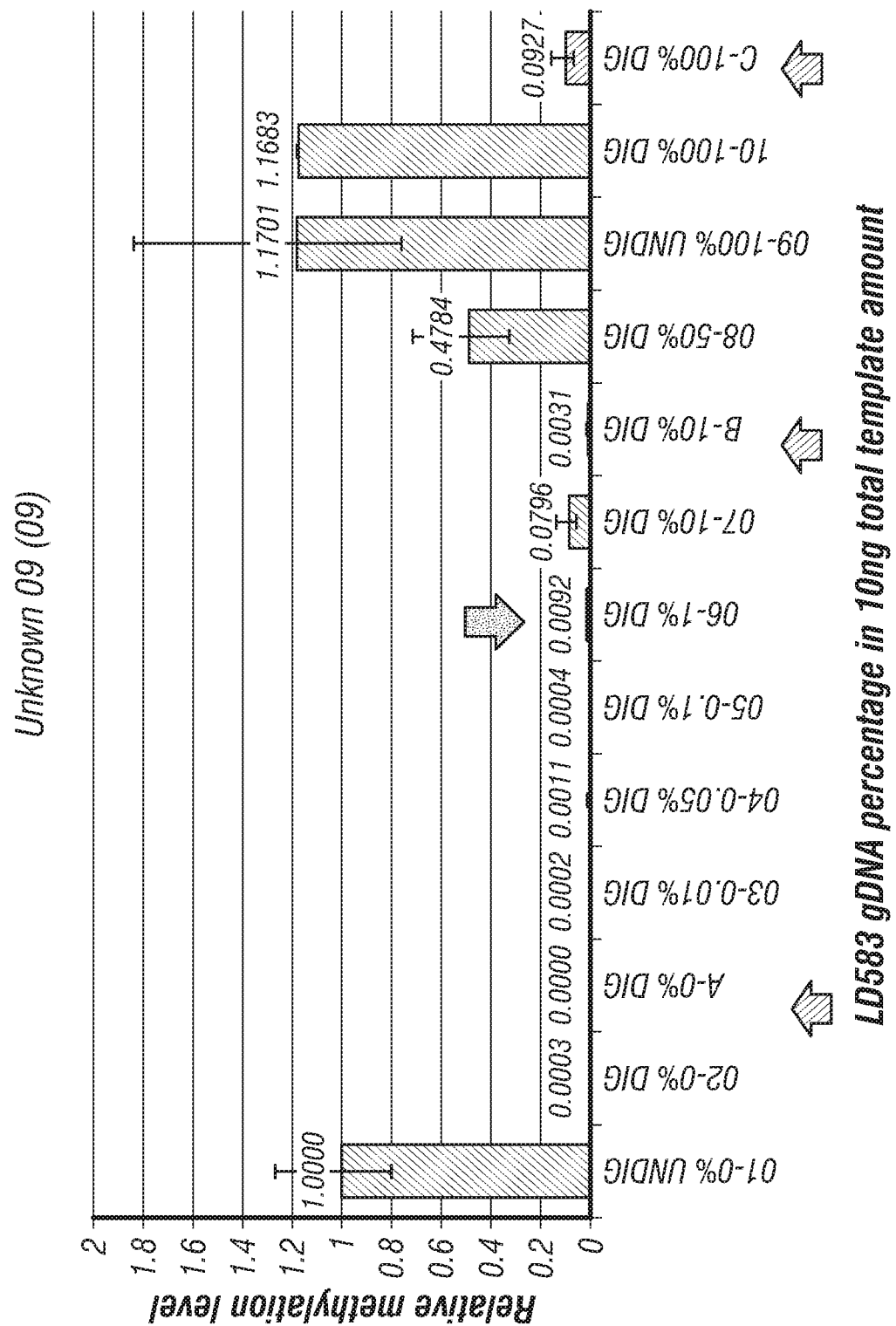
FIG. 3: Detection Limits and One-step vs. Two-step method. 0.25-1% of amplification is considered above the background level; 0.25% lends low confidence and 1% lends high confidence. LD583 bladder cancer cell line (Isabel D.C. Markl and Peter A. Jones, Cancer Research 58, 5348-5353, Dec. 1, 1998) gDNA was mixed with normal Urine gDNA. Reactions A, B and C were done using the single-step method (marked with arrows) illustrating that one step-reaction is not applicable for all the markers.
Figure 4:
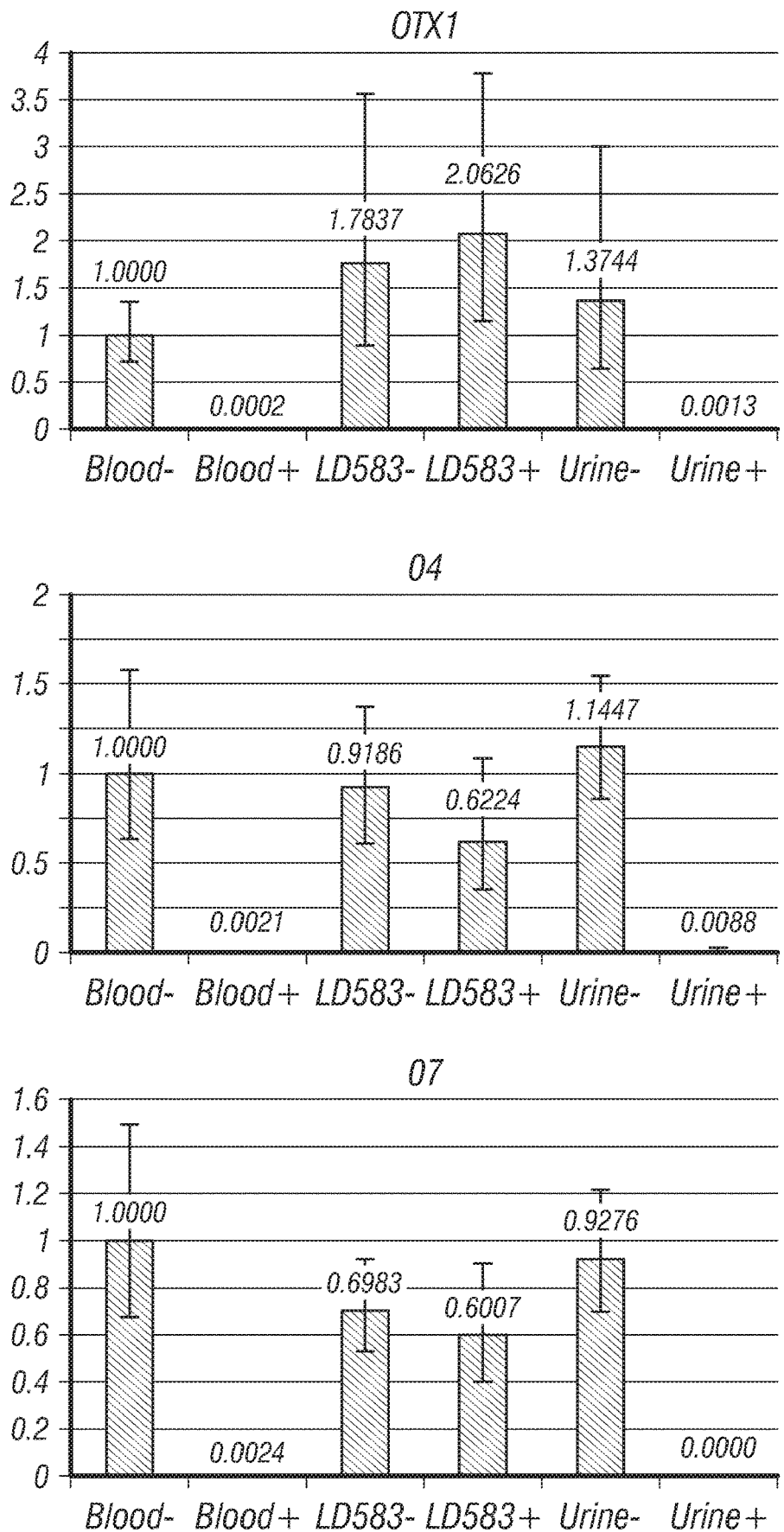
Figure 4:
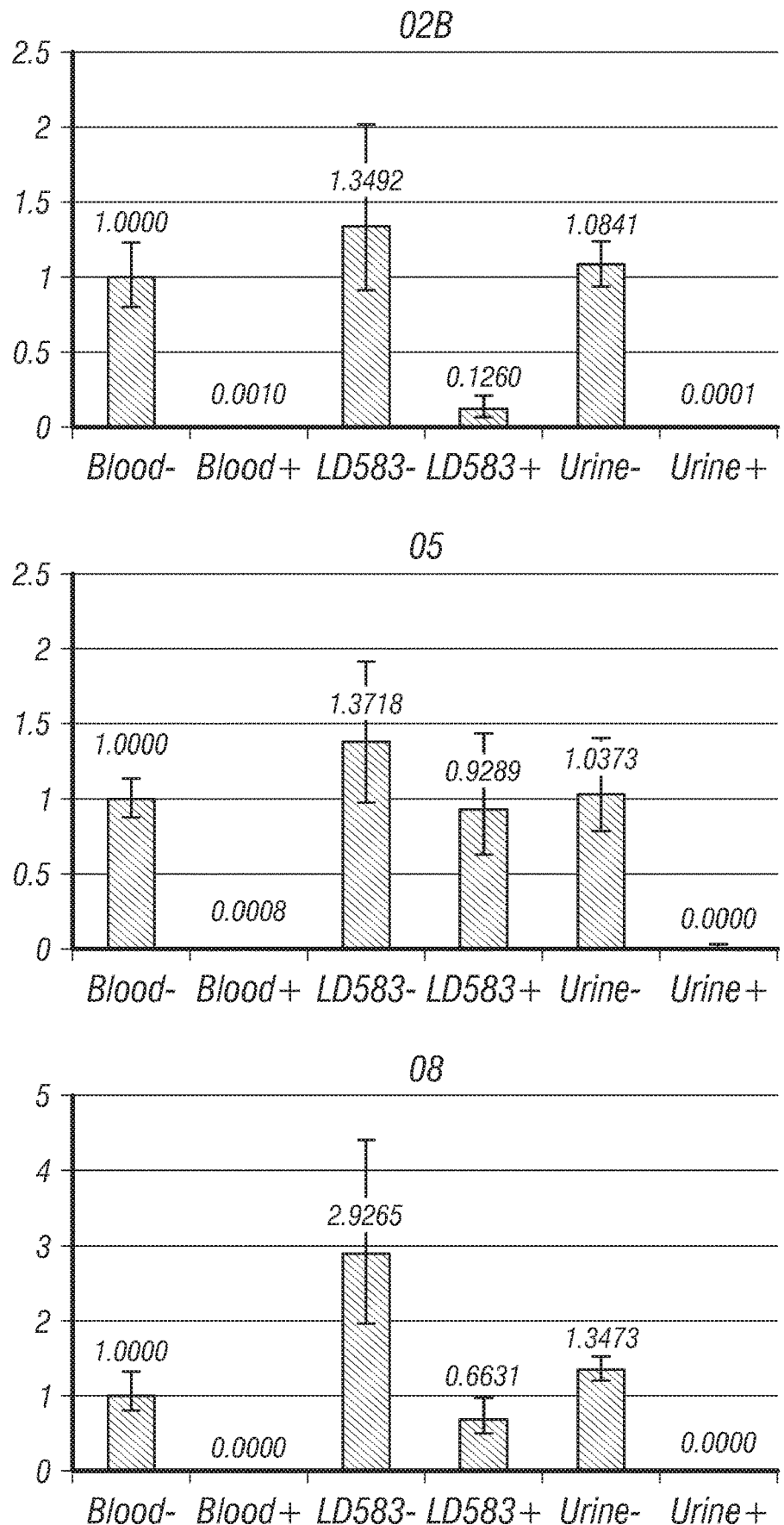
Figure 4:
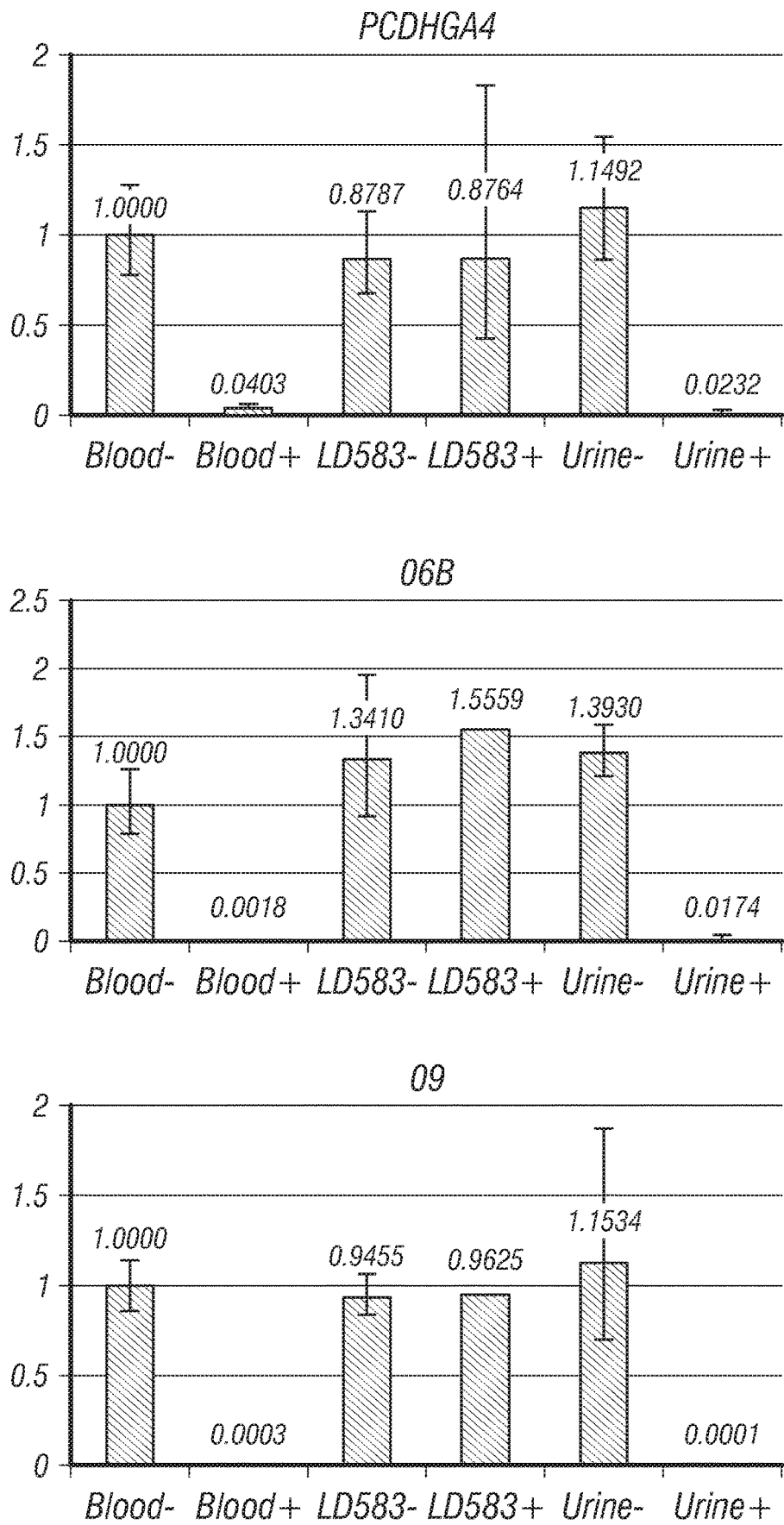
Figure 5:
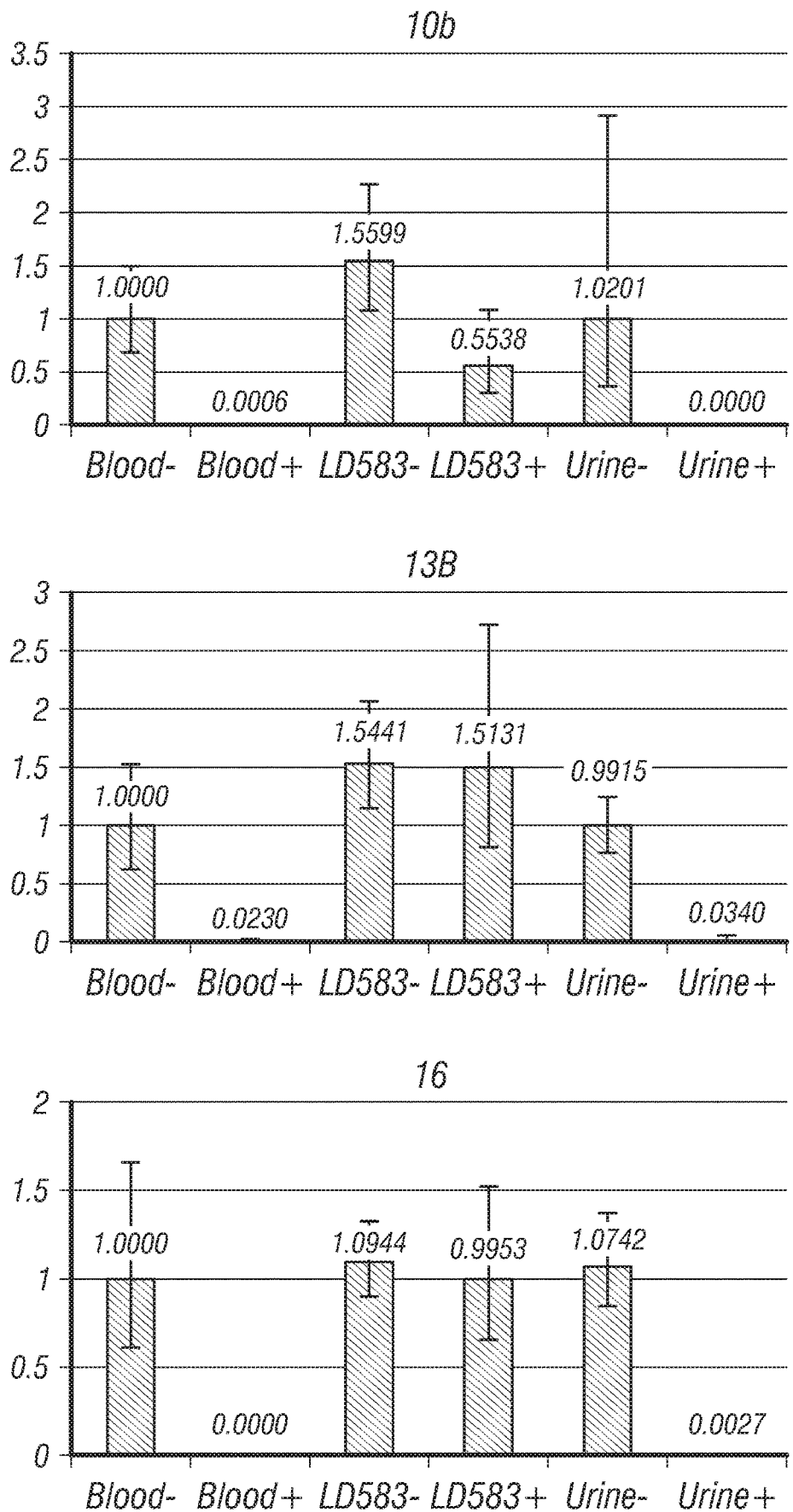
Figure 5:
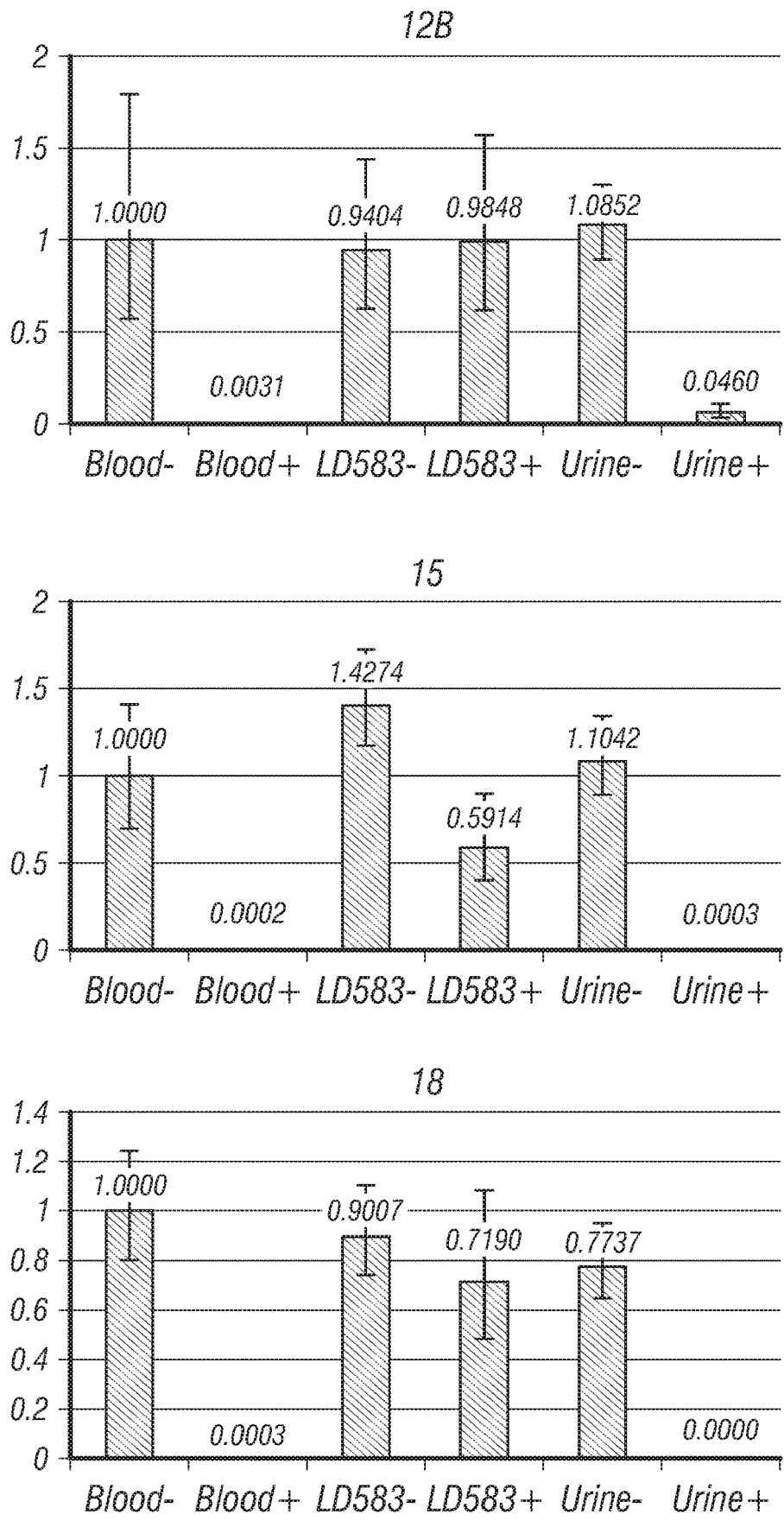
Figure 6:
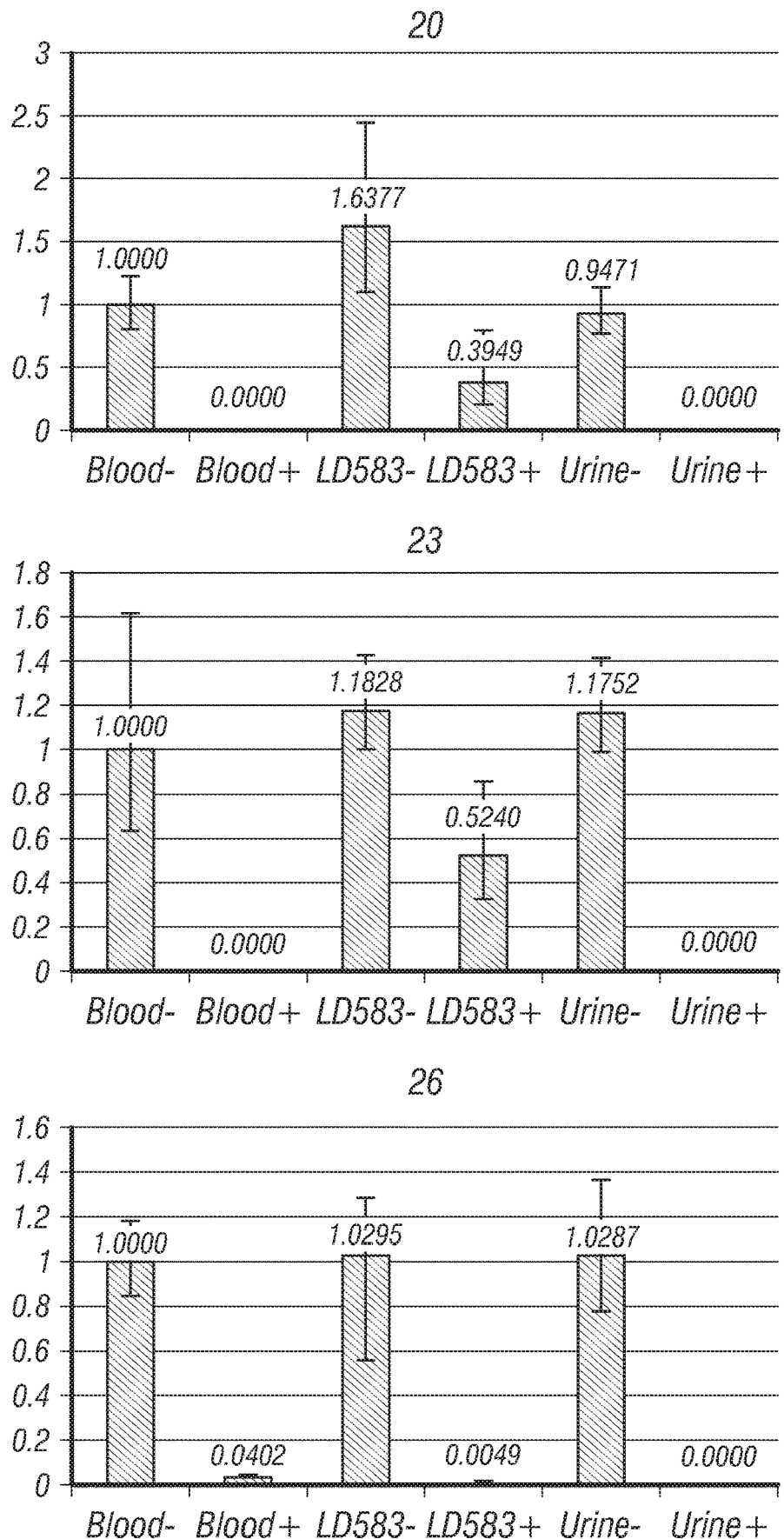
Figure 6:
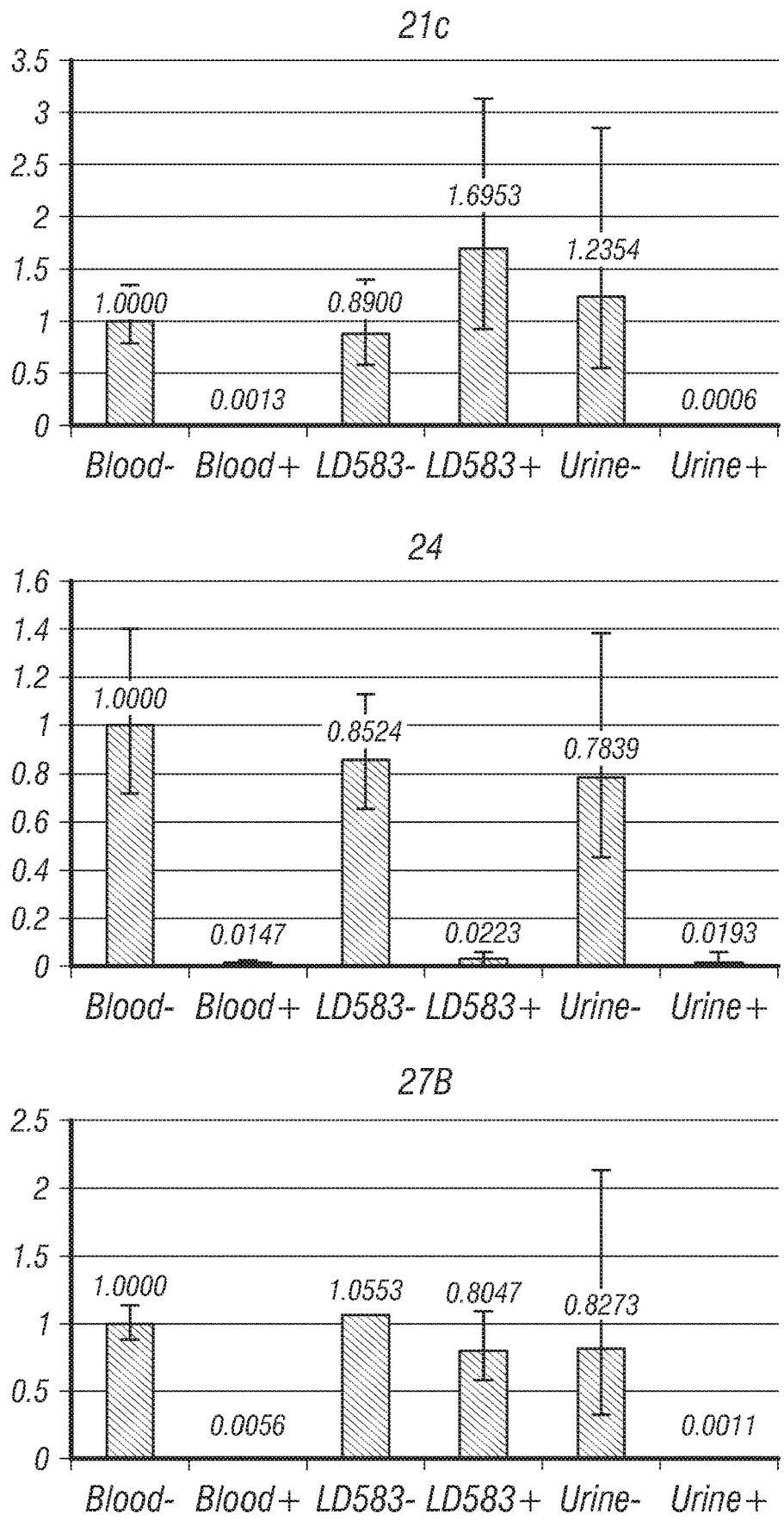

Digestion and qPCR reactions were done in separate tubes (two-step) since the single-step reaction strongly decreased the sensitivity of the method for some markers (FIG. 3). When the enzyme mix was added to the qPCR mixture containing the template, a strong reduction of the amplification efficiency was observed for some of the markers. This was not caused by altered digestion efficiency nor for an alteration of the polymerase activity since the amplification of the POLR2A control marker was comparable between the single vs the two-step reaction.

All the markers listed in Table 2 (including LINE-1 and DPM2 controls) were tested to verify their methylation status in cancer using the MSRE qPCR approach. qPCR reactions where thus performed using undigested and digested genomic DNA obtained from blood, LD583 bladder cancer cell line and normal Urine (from non-cancer individuals). All the samples were normalized against undigested blood gDNA (reference sample; considered to be 100%) and values were corrected for the amount of template loaded in the reaction (this was determined using the POLR2A control marker). Digestion efficiencies were determined using the GAPDH control marker. The results are shown in FIGS. 4-9.

Preferred markers were markers that did not show any methylation in blood and normal urine gDNA and were 100% methylated in the cancer cell line DNA. From this analysis, makers that resulted less than 2% methylated in blood or normal urine DNA were subdivided into three categories (see Table 3 below).

TABLE 3

Category A—Methylation level in normal blood and urine <1%, Methylation level in LD583 bladder cancer cell line >70%; Category B—Methylation level in normal blood and urine <1%, Methylation level in LD583 bladder cancer cell line > 50% < 70%; Category C—Methylation level in normal blood and urine > 1% < 2%, Methylation level in LD583 bladder cancer cell line >70%.

| Category A | | Category B | | Category C | |
|---|---|---|---|---|---|
| 09 | Unk (Unc) 09 | 08/15 | GALR1 | 06B | SCT |
| 05 | Unk05 | 23 | TBX15 | 14 | Unk14 |
| 18 | DCHS2 | 32 | EEF1A2 | 29 | Unk29 |
| 01 | OTX1 | 10B | DMRTA2 | 31 | CERKL |
| 07 | Unk07 | 04 | TFAP2B | 34B | SHH |
| 30 | EVX2 | | | | |
| 16 | SEPT9 | | | | |
| 27B | SOX1 | | | | |
| 19 | Unk19 | | | | |
| 21C | Unk21 | | | | |
| 36 | SOX17 | | | | |

Blood is known to be a major urine contaminant, however also sperm might contaminate urine sample. Because of this, the methylation level of all the 21 above validated markers in Table 3 were also tested using sperm DNA. The results confirm that all the 21 markers are not methylated in sperm DNA (<1%).

Additionally, for the 16 markers belonging to categories A and B in Table 3, the methylation detection limit the MSRE qPCR system was determined and thus the minimum amplification value that can be considered higher than the background signal (background was determined in digested normal Urine gDNA, which is not methylated; e.g. see FIG. 3). In general, for all the 16 markers the background signal is lower than 0.25%. This value is therefore considered the low-confidence background limit, so a digested sample with a methylation signal higher than 0.25% is putatively considered positive. To enhance the reliability of MSRE qPCR system, the inventors increased to 1% the confidence limit and considered this value to be the high-confidence background limit. A sample with a value higher than 1% is considered truly positive. Samples with a value between 0.5 and 1% are considered low-confidence positive, while digested sample with a methylation level higher than 1% are considered high-confidence positive for cancer.

Example 2—Human Sample Analysis with Exemplary Markers

Figure 13:
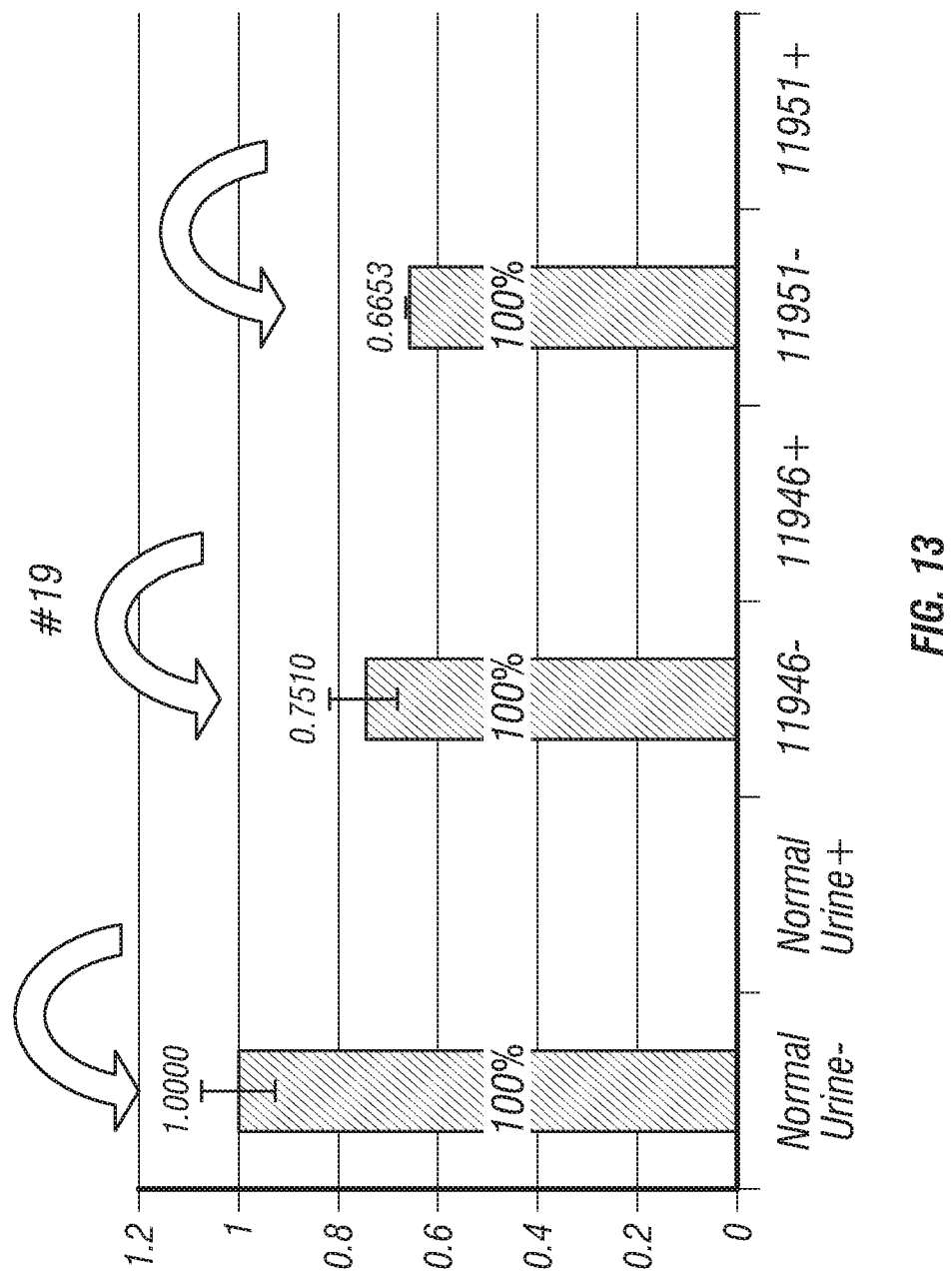
FIG. 13: Example of analysis conducted in Example 2 showing results with marker 19. Signal of digested samples (+) were calculated by comparison with the signal in the corresponding undigested samples (100%). Data were also corrected using POLR2A as a loading control (internal control) and complete DNA digestion was detected using GAPDH control marker.
Figure 14A:
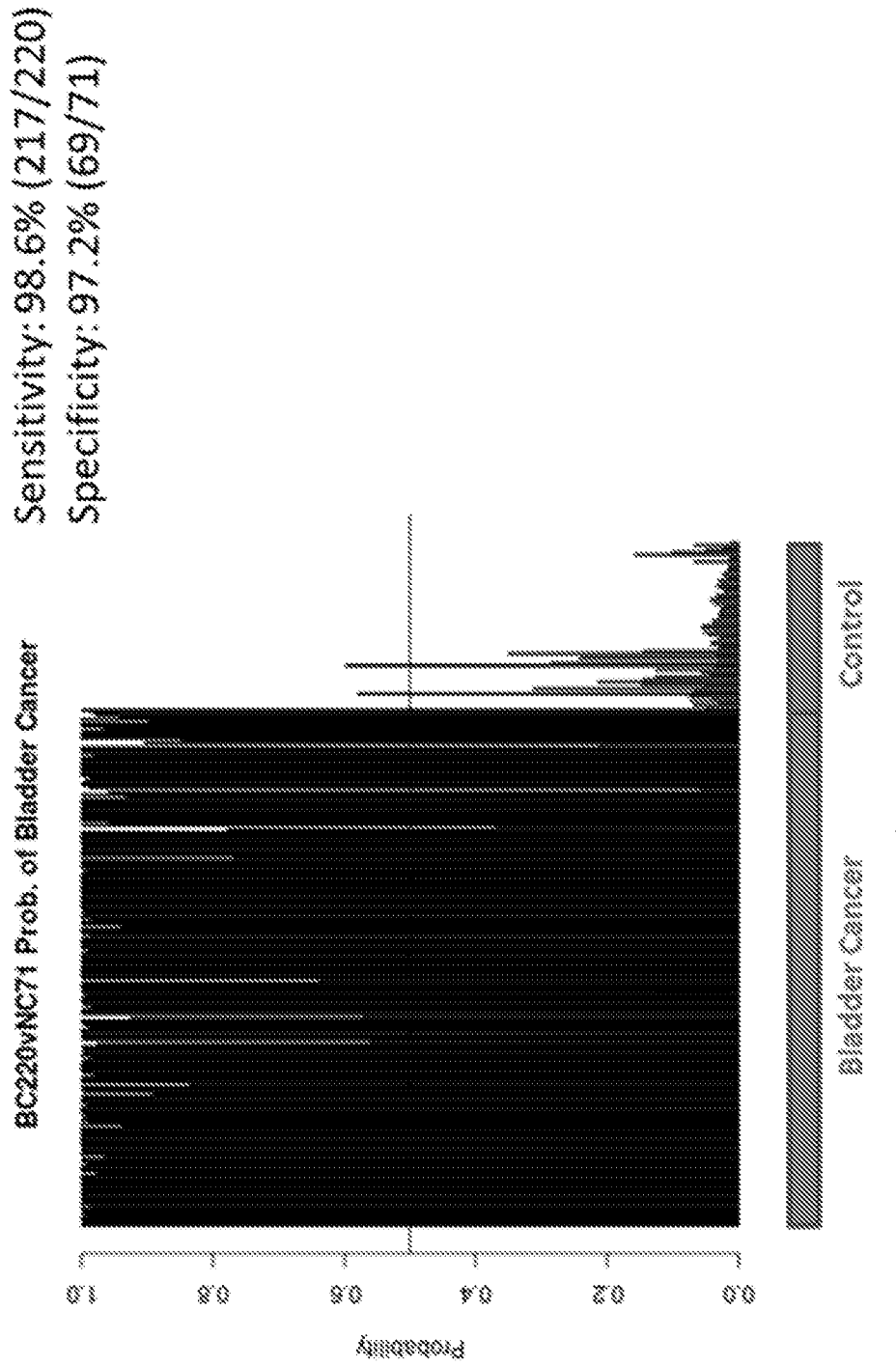
FIG. 14A-E: Probability of bladder cancer for training samples and hierarchical clustering using selected DNA methylation biomarkers. (A-B) Methylation markers derived from HM450 human methylation array data of tumor tissues and controls. (C) Methylation markers derived from HM450 array data of urine samples from bladder cancer patients and healthy controls. (D-E) Methylation markers derived from Reduced Representation Bisulfite Sequencing (RRBS) data of tumor tissues and controls.
Figure 14B:
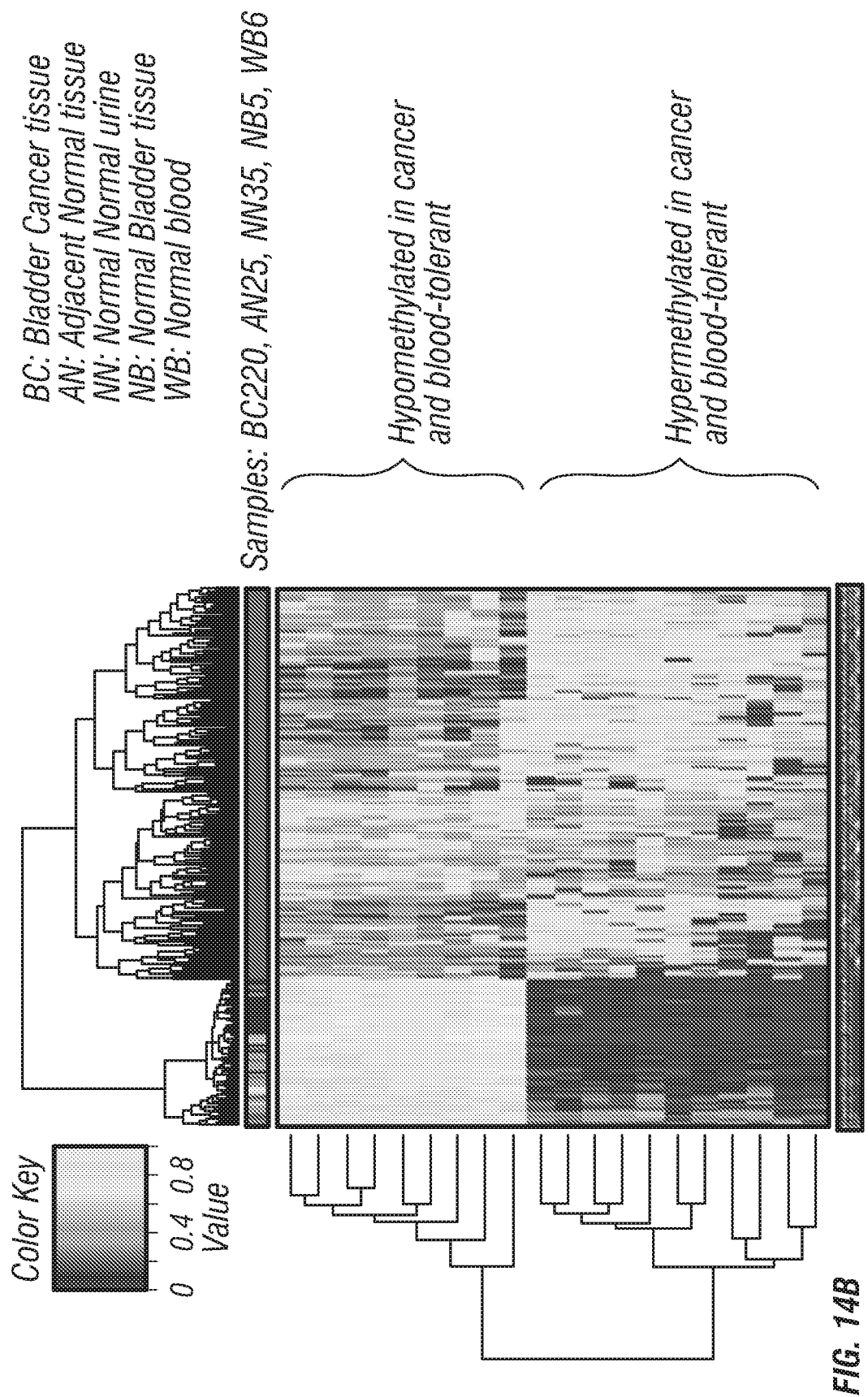
Figure 14C:
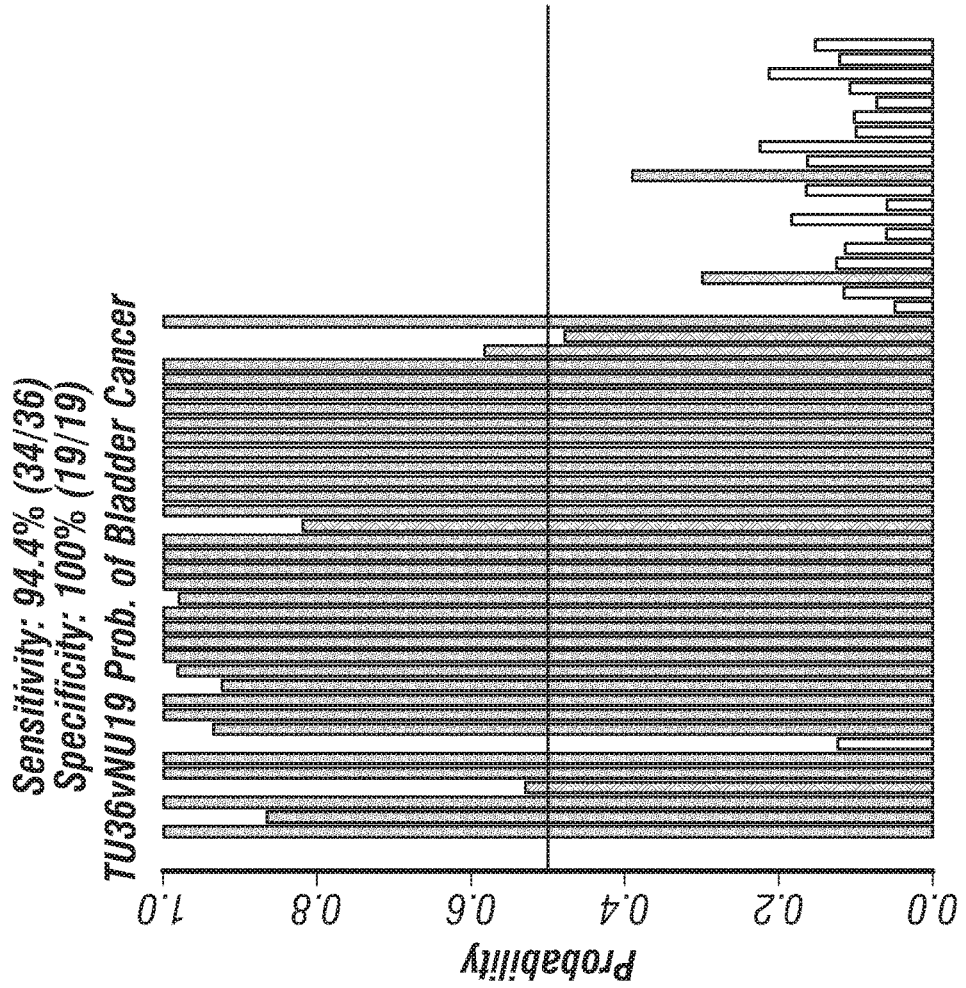
Figure 14C:
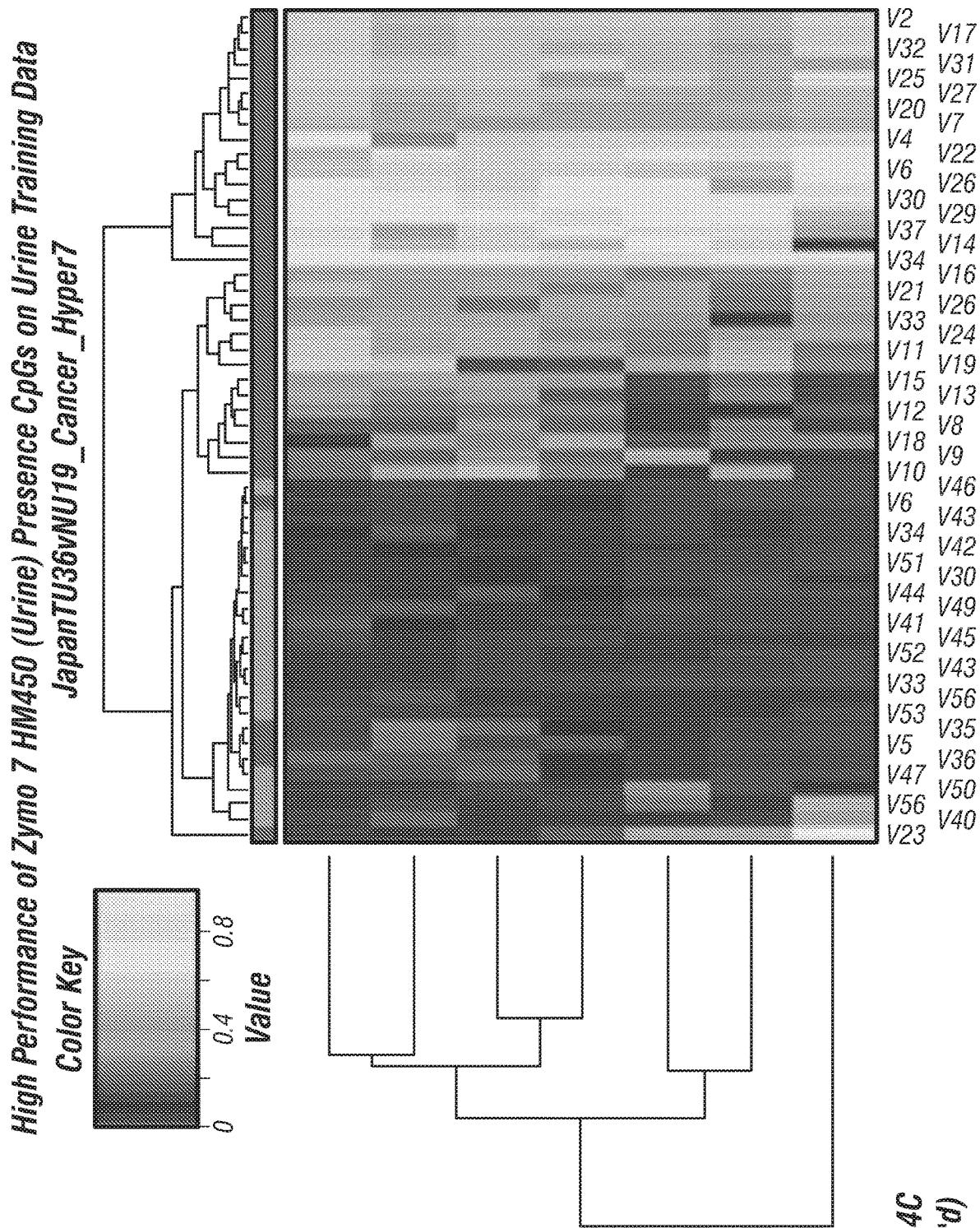
Figure 14D:
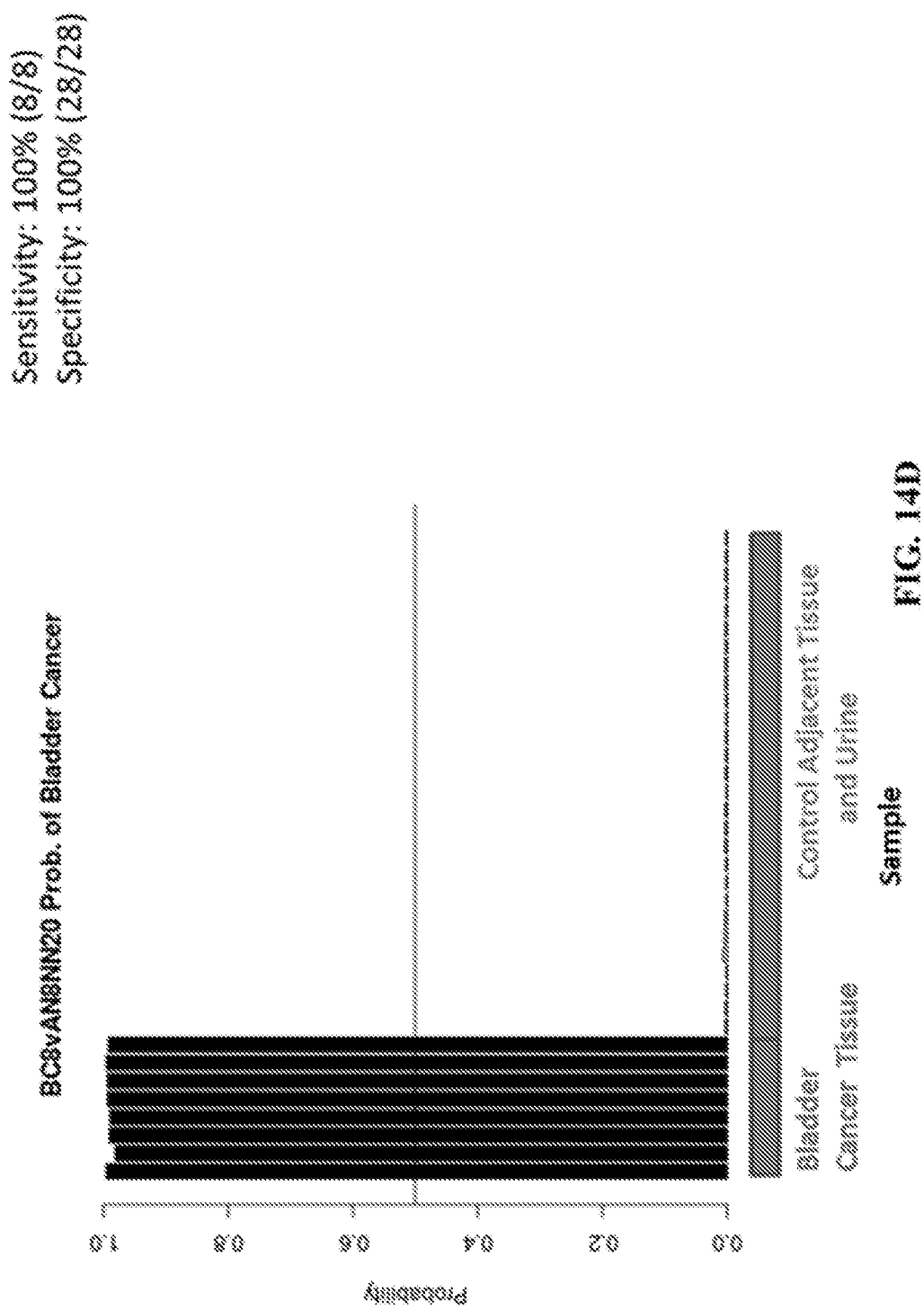
Figure 14E:
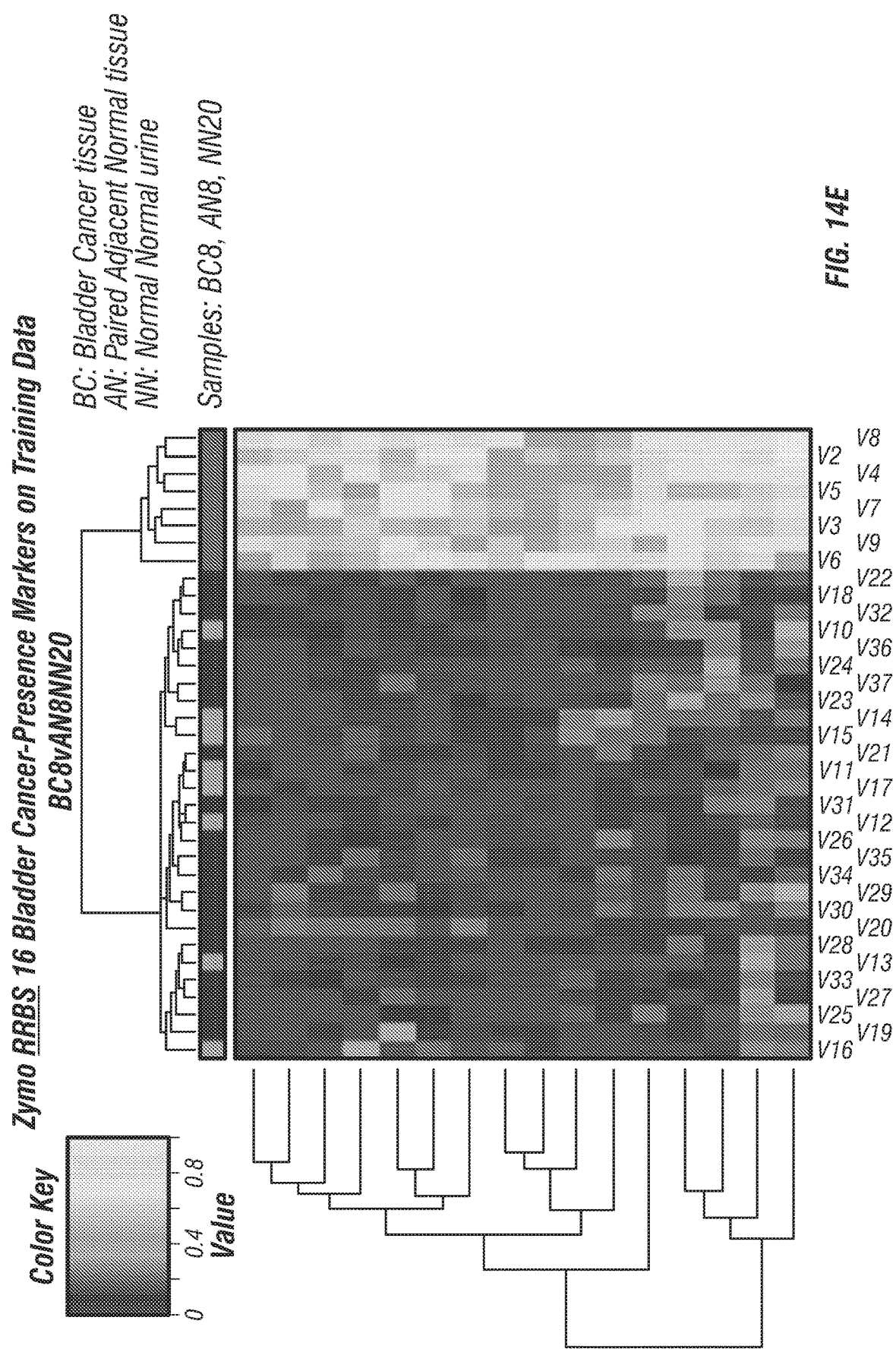
Figure 15:
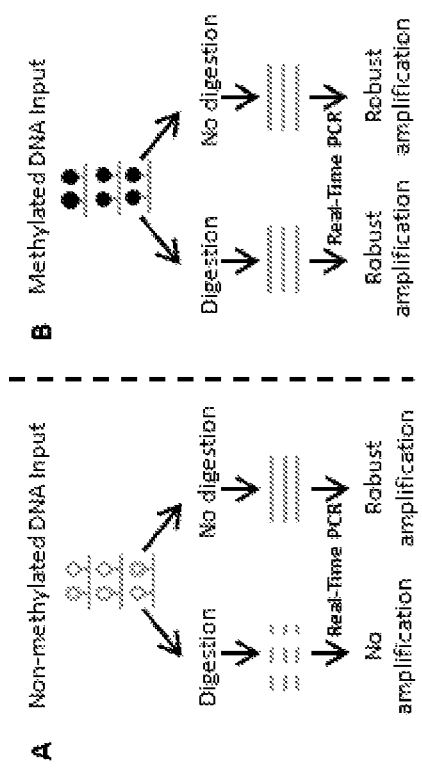
FIG. 15: Schematic representation of CARE assay. Unmethylated (A) and methylated (B) DNAs are analyzed using CARE assay. DNA methylation will impede DNA cleavage in the digestion reaction, thus robust amplification occurs during the following qPCR step in B), but not in A). A no-digestion control reaction is run in parallel for each experiment.
Figure 16:
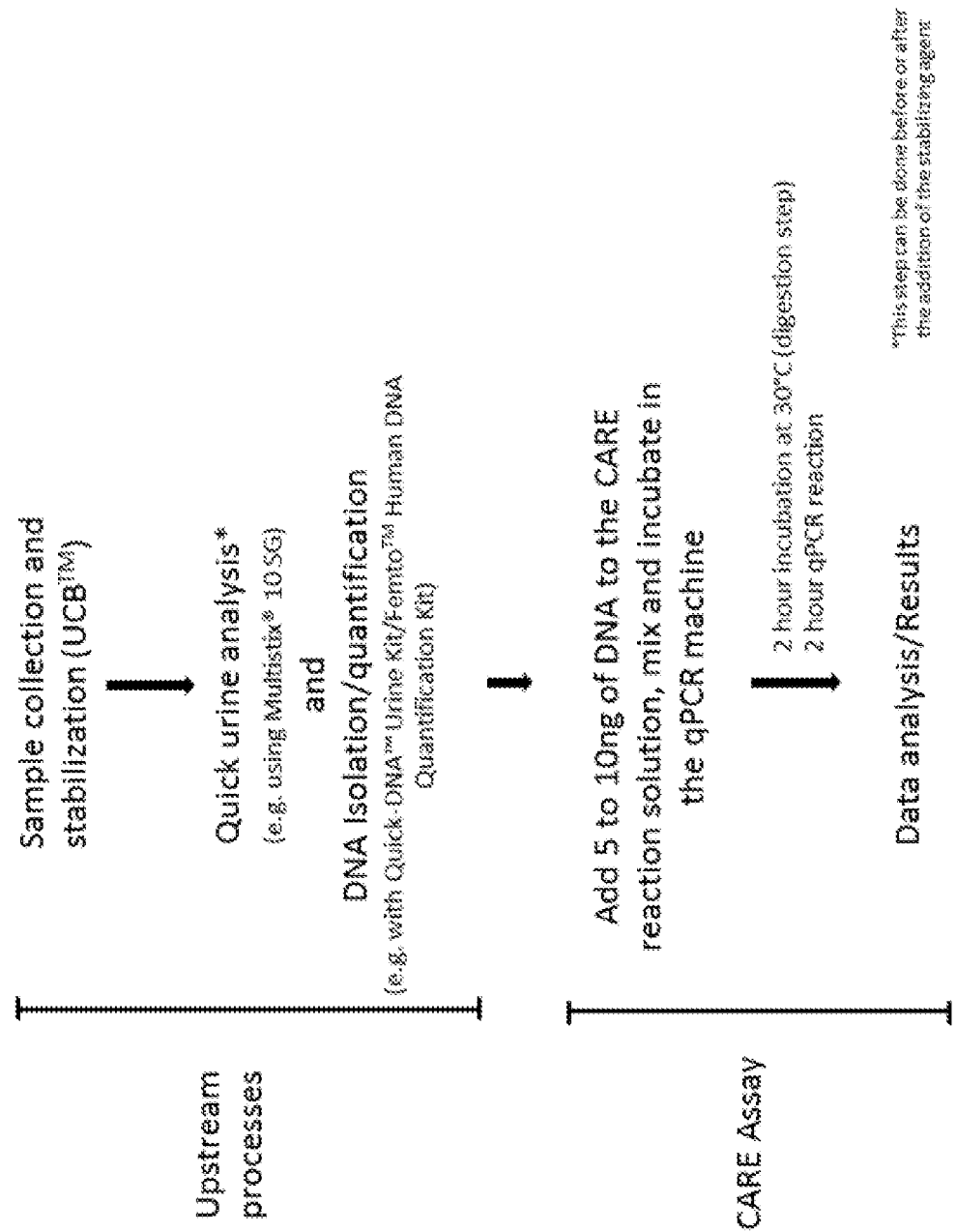
FIG. 16: Schematic depicting CARE assay general workflow.

Clinical trial urine samples from bladder cancer tumor patients and normal (non-cancer) urine samples were analyzed using the category A and B markers listed in Table 3. The % of the signal detected for a specific digested sample was calculated by comparison with the signal of the same sample but undigested (100%) (in Example 1, all the signals were calculated in comparison with the signal of undigested blood sample) (e.g. FIG. 13).

The methylation signals in digested clinical samples compared with the same undigested samples are shown in FIG. 10. Blinded patient status classification based on MSRE data is shown in FIG. 11. The results show that 4 out of 13 patients appear to be healthy (marked in green), while 5 are most likely developing cancer at various stages (marked in red). Other four patients are positive for cancer at low-confidence (borderline cases, marked in orange).

Markers 01, 16 and 04 (see red arrows in FIG. 10) showed a higher background in normal Urine (although <1%; red circle) compared with the other markers. Values from these three markers were not considered for the final clinical sample classification (FIG. 11).

Example 3—Analysis of Methylation Using Enhanced CARE Assay

The assay of Example 1 was further developed to increase its overall performance, including sensitivity, simplicity and detection limit. First, the 16 cancer markers panel (Table 4) that have methylation levels of at least 50% in the LD583 bladder cancer cell line and generally lower than 1% in normal urine, blood and sperm samples was further analyzed to arrive at a panel of 12 markers to validate clinical samples.

TABLE 4

List of the 16 biomarkers that can better discriminate bladder cancer (LD583 bladder cancer cell line) from normal sample (blood and urine collected from healthy individuals).

| CODE | ASSOCIATED GENE/EST | CODE | ASSOCIATED GENE/EST |
|---|---|---|---|
| #09 | Unknown 09 (Unc09) | #15 | GALR1 |
| #05 | Unk05 | #23 | TBX15 |
| #18 | DCHS2 | #32 | EEF1A2 |
| #01 | OTX1 | #10 | DMRTA2 |
| #21 | Unk21 | #27 | SOX1 |
| #07 | Unk07 | #04 | TFAP2B |
| #30 | EVX2 | #36 | SOX17 |
| #16 | SEPT9 | #19 | Unk19 |

A small cohort of normal urine DNA samples (n=9) collected from individuals with different age, gender and ethnicity was analyzed by the assay of Example 1. As shown in Table 5, all of the 9 samples were classified as negative for bladder cancer. Despite the fact that the cohort was very small, no significant differences in methylation background levels were linked to age, gender or ethnicity.

TABLE 5

DNA urine samples collected from 9 healthy individuals were analyzed with a first version of CARE assay. Sample codes are indicated in the first column, while markers are listed in the first row. Age (year), gender and ethnicity are indicated for each sample. GAPDH represents the digestion control. Methylation levels >0.25% are indicated in white; >0.25% but <1% with YY; >1% with BB. Experiment was performed using two technical replicates.

| Sample Code | Age | Gender | Ethnicity | GAPDH GAPDH | Unk09 #09 | Unk05 #05 | DHCS2 #18 | Unk07 #07 | EVX2 #30 | SOX1 #27 | Unk19 #19 | Unk21 #21 | SOX17 #36 | GALR1 #15 | TBX15 #23 | DMRTA2B #10 | TFAP2B #04 | OTX1 #01 | SEPT9 #16 | EEF1A2 #32 |
|---|---|---|---|---|---|---|---|---|---|---|---|---|---|---|---|---|---|---|---|---|
| Sample #09 | 29 | F | African | | | | | | | | | | | | | | BB | BB | YY | |
| #16 | 28 | F | Caucasian | | | | | | | | | | | | | | | YY | | |
| #22 | 29 | M | Caucasian | | | | | | | | | | | | | | BB | | BB | YY |
| #02 | 48 | M | Caucasian | | | | | | | | | | | | | | BB | | BB | YY |
| #19 | 44 | M | Caucasian | | | | | | | YY | | | | | | | BB | | BB | BB |
| #20 | 41 | M | Caucasian | | | | | | | | | | | | | | | | | |
| #03 | 55 | M | Asian | | | | | | | | | | YY | | | | BB | | YY | YY |
| #17 | 72 | F | Caucasian | | | | | | | | | | | | | | BB | YY | | |
| #24 | 52 | F | Caucasian | | | | | | | | | | | | | | YY | YY | BB | YY |

Moreover, the results also pointed out an increased background level for four markers (the four rightmost markers in Table 5). In particular marker #04 had a methylation level >1% (up to 4%) in most of the samples, while marker #01 had an elevated background in four out of nine samples. Marker #16 (SEPT9) and #32 (EEF1A2), that are associated with relevant malignancies including colorectal, prostate, pancreas, breast and ovarian cancers, also had a high background in a few, but not all, samples. It is interesting, however, that the background level of these two markers is very similar in terms of sample pattern and magnitude. To note, SEPT9 methylation levels in sample #03 and #05 were confirmed by a parallel experiment based on DNA bisulfite-conversion instead of CARE assay. This similarity might indicate that the increased methylation level in these samples is not due to technical issues (e.g. incomplete digestion) but is rather specifically elevated in some sample. This suggests that the slightly increase in methylation of these two markers might not be random and might perhaps be indicative, or predictive, of a specific clinical status (i.e. risk to develop a specific clinical condition). Thus, marker #32 was kept in the marker panel. Instead, markers #04, #01 and #16 were not considered for further validation experiments reducing the bladder cancer biomarker panel to 13 loci.

Next, the selected 13 bladder cancer biomarkers were tested using a small cohort (n=10+10) of bladder cancer samples and their correspondent adjusted normal tissues (non-cancer bladder tissue isolated along with the tumor at the moment of tumor removal) (Table 6). The overall methylation level of the 13 cancer biomarkers was significantly higher in tumor samples than in the adjusted normal one. 7 out of 10 tumor samples had all 13 markers significantly methylated (>1%). Some markers, specifically #27, #36 and #30 were also highly methylated in the adjusted normal samples.

TABLE 6

Analysis of DNA extracted from 10 bladder cancer tissues and their correspondent adjusted normal sample (the last indicated in Italic) using CARE assay. Sample codes are indicated in the first column, while markers are listed in the first row. As in Table 5, each biomarker and sample values are expressed as percentage of methylation present after digestion. GAPDH represents the digestion control. Methylation levels <0.25% are indicated in white; >0.25% but <1% with YY; >1% with BB. Experiment was performed using two technical replicates.

| | Sample Code | GAPDH GAPDH | Unk09 # 09 | Unk05 # 05 | DHCS2 # 18 | Unk07 # 07 | EVX2 # 30 | SOX1 # 27 | Unk19 # 19 | Unk21 # 21 | SOX17 # 36 | GALR1 # 15 | TBX15 # 23 | EEF 1A2 # 32 | DMRTA 2B # 10 |
|---|---|---|---|---|---|---|---|---|---|---|---|---|---|---|---|
| Sample | 01-01-0036-01-D2 | | BB | BB | BB | BB | BB | BB | BB | BB | BB | BB | BB | BB | BB |
| | 01-02-0036-01-D2 | | BB | BB | BB | BB | BB | BB | BB | BB | BB | BB | BB | BB | BB |
| | 01-01-0037-01-D2 | | | YY | | | YY | BB | | | BB | BB | BB | | BB |
| | 01-02-0037-01-D2 | | YY | YY | | YY | YY | BB | YY | YY | BB | | | BB | |
| | 01-01-0038-01-D2 | | BB | BB | BB | BB | BB | BB | BB | BB | BB | BB | BB | BB | BB |
| | 01-02-0038-01-D2 | | | YY | | YY | YY | BB | YY | | YY | | YY | YY | YY |
| | CD564833 | | BB | BB | BB | BB | BB | BB | BB | BB | BB | BB | BB | BB | BB |
| | CD5E4841 | | | YY | YY | YY | BB | YY | YY | YY | YY | YY | | | YY |
| | CD564111 | | BB | BB | BB | BB | BB | BB | BB | BB | BB | BB | BB | BB | BB |
| | CD564102 | | BB | BB | BB | BB | BB | BB | BB | BB | BB | | | BB | BB |
| | 01-01-0041-01-D1 | | BB | BB | BB | BB | BB | BB | | | BB | | YY | BB | BB |
| | 01-02-0041-01-D2 | | YY | | YY | YY | BB | BB | BB | | BB | BB | | YY | |
| | 01-01-0042-01-D1 | | BB | BB | BB | BB | BB | BB | BB | BB | BB | BB | BB | BB | BB |
| | 01-02-0042-01-D2 | | YY | YY | YY | YY | YY | YY | YY | YY | YY | YY | | BB | YY |

TABLE 6-continued

Analysis of DNA extracted from 10 bladder cancer tissues and their correspondent adjusted normal sample (the last indicated in Italic) using CARE assay. Sample codes are indicated in the first column, while markers are listed in the first row. As in Table 5, each biomarker and sample values are expressed as percentage of methylation present after digestion. GAPDH represents the digestion control. Methylation levels <0.25% are indicated in white; >0.25% but <1% with YY; >1% with BB. Experiment was performed using two technical replicates.

| | | | | | | | Markers | | | | | | | |
|---|---|---|---|---|---|---|---|---|---|---|---|---|---|---|
| Sample Code | GAPDH GAPDH | Unk09 # 09 | Unk05 # 05 | DHCS2 # 18 | Unk07 # 07 | EVX2 # 30 | SOX1 # 27 | Unk19 # 19 | Unk21 # 21 | SOX17 # 36 | GALR1 # 15 | TBX15 # 23 | EEF1A2 # 32 | DMRTA2B # 10 |
| 01-01-0043-01-D2 | | BB | BB | BB | BB | BB | BB | BB | BB | BB | BB | BB | BB | BB |
| 01-02-0043-01-D2 | | BB | BB | BB | BB | BB | BB | BB | YY | BB | YY | YY | BB | BB |
| 01-01-0044-01-D2 | | BB | BB | BB | BB | BB | BB | BB | BB | BB | BB | BB | BB | BB |
| 01-02-0044-01-D2 | | BB | BB | BB | BB | BB | BB | YY | BB | BB | BB | BB | BB | BB |
| 01-01-0045-01-D1 | | | BB | BB | BB | BB | BB | BB | BB | BB | BB | BB | BB | BB |
| 01-02-0045-01-D1 | | | | | | YY | YY | | | | | | YY | |

The data generated from this analysis were used to score every single marker; in particular each marker was evaluated for A) its ability to recognize a bladder malignancy; this parameter was determined as the number of tumor samples recognized positive (methylation level >1%) by a specific marker. Each cancer-specific marker should be significantly methylated in all the tumor samples; B) for the level of methylation of a specific marker in a specific tumor sample in comparison to the average methylation level between all the markers in the same sample (a high methylation level in cancer samples is desirable); C) For the number of adjusted normal sample not recognized as normal sample; this last parameter was considered important since, contrary to blood or normal urine, adjusted normal samples are expected to show an increase in bladder cancer markers methylation levels since they are tissue samples often containing cells predisposed to the development of cancer, a phenomena named "field effect" (e.g. Giovannucci and Ogino, 2005; Bernstein et al., 2007); it is therefore expected that the methylome of adjusted normal sample will be altered at some extent. It was reasoned that a good cancer marker is supposed to detect these differences. Based on these criteria the 13 markers were classified into three marker set categories (A, B and C; Table 7). Set A and B contain the controls and the markers that more likely will be included in the final marker set, while set C include all the other markers. To note, marker #23 showed poor performances as cancer marker (low methylation level in many tumor samples compared to the other markers), therefore it was not included in any set. Thus, the marker panel contains 12 biomarkers.

TABLE 7

The 12-selected biomarkers (right column for each set) were classified into three sets based on the results obtained in the experiment presented in Table 6. Set A and B contain the markers with the best performances and the two internal controls POLR2A and GAPDH, while set C contains all the other markers.

| SetA | | SetB | | SetC | |
|---|---|---|---|---|---|
| POLR2A | | | #05 | Unk05 | #09 | Unk09 |
| GAPDH | | | #07 | Unk07 | #32 | EEF1A2 |
| #27 | SOX1 | #30 | EVX2 | #19 | Unk19 |
| #15 | GALR1 | #36 | SOX17 | #21 | Unk21 |
| #10 | DMRTA2 | #18 | DCHS2 | | |

All the markers included in the three sets (Table 7) of the new panel were further validated using DNA isolated from normal urine sample collected from a larger cohort (n=31). This experiment confirmed the data already presented in Table 5 and methylation background was found to be low for all the markers except for marker #32 (that was found to be elevated in some sample).

In an additional experiment, it was tested if the selected biomarker panel could be used to identify different type of malignancies. To this end, DNA extracted from bladder, prostate, endometrium and kidney tumor and their correspondent adjusted normal sample was analyzed. Moreover, also included in the analysis was one bladder sample isolated from a healthy individual (as a negative control) and three multiple myeloma sample (HA, MM1.S and CRF30).

TABLE 8

CARE analysis of DNA extracted from different cancer sample (TU), their correspondent adjusted normal samples (AN) and three different multiple myeloma samples (HA, MM1.S and CRF30). A healthy bladder control was included in the analysis. Samples are listed in the first column, while markers are indicated in the first row. Values for each biomarker and sample are expressed as percentage of methylation present after digestion. GAPDH represents the internal digestion control. Methylation levels <0.25% are indicated in white; >0.25% but <1% with YY; >1% with BB. Experiment was performed using two technical replicates.

| | Sample | GAPDH GAPDH | SOX1 827 | GALR1 #15 | DMRTA2B #10 | Unk05 #05 | Unk07 #07 | EVX2 #30 | SOX17 #36 | DHCS2 #18 | Unk09 #09 | EEF1A2 #32 | Unk19 #19 | Unk21 #21 |
|---|---|---|---|---|---|---|---|---|---|---|---|---|---|---|
| Sample | Healthy Bladder | | | | | YY | | YY | | | YY | YY | YY | |
| | Bladder TU | | BB | BB | BB | BB | BB | BB | BB | BB | BB | BB | BB | BB |
| | Bladder AN | | BB | BB | BB | BB | YY | BB | BB | YY | BB | BB | BB | YY |
| | Prostate TU | | BB | BB | BB | BB | BB | BB | BB | BB | BB | BB | BB | |
| | Prostate AN | | YY | | | BB | | YY | YY | | BB | BB | | |
| | Endometrium TU | | BB | BB | BB | BB | BB | BB | BB | BB | BB | BB | BB | BB |
| | Endometrium AN | | BB | BB | BB | BB | BB | BB | | BB | BB | YY | BB | BB |
| | Kidney TU | | YY | | | YY | YY | BB | YY | | | YY | YY | |
| | Kidney AN | | | | | YY | | BB | | | | BB | YY | |
| | HA | | BB | BB | BB | BB | BB | BB | BB | BB | BB | BB | BB | BB |
| | MM1.S | | BB | BB | BB | BB | BB | BB | BB | BB | BB | BB | BB | BB |
| | CRF30 | | BB | BB | | BB | BB | BB | | | | YY | BB | BB |

Despite the small cohort used, the results clearly demonstrated that many of the biomarkers listed in sets A, B and C are heavily methylated in different types of cancer including bladder, prostate, endometrial and multiple myeloma tumors. Surprisingly, no increase of methylation was detected in kidney cancer. As expected, none of the markers was found to be significantly methylated (methylation level >1%) in DNA isolated from healthy bladder. Additional different types of cancer can potentially also be detected using only urine samples.

In addition to the trials described above, a pre-clinical study was performed in which a small cohort of 63 urine sample was analyzed using the enhanced CARE assay. As indicated in Table 9 this cohort includes 20 samples collected from healthy individuals ("Normal sample") with different age, gender and risk behaviors concerning bladder cancer development (the cohort in fact includes four young smoker individuals –<55 years old-). The rest of the cohort (n=43; "Cancer sample") is represented by samples collected from individuals with bladder cancer and other type of tumors; specifically, 33 samples were collected from persons affected by bladder cancer before cancer removal ("Bladder cancer before surgery"), 8 sample were collected from individuals who were recently subjected to blabber tumor removal ("Bladder cancer after surgery") and other 2 samples (collectively named "Non-bladder cancer") were collected from individuals, #48N and #34S, affected by stomach cancer and colon adenocarcinoma, respectively.

TABLE 9

CARE analysis of DNA extracted from urine samples collected from 20 healthy individuals (normal sample; indicated in the upper part of the table) and from 43 patients affected by cancer (cancer sample). The first column indicates the subgroups description (YO = years old), while sample codes are listed in the second column. Markers are indicated in the first row. A blood sample control was included in the analysis (second row) while GAPDH represents the internal digestion control. Methylation levels <0.25% are indicated in white; >0.25% but <1% with YY; >1% with BB. Experiment was performed using two technical replicates.

| | Sample | GAPDH | SOX1 #27 | GALR1 #15 | DMRTA2B #10 | Unk05 #05 | Unk07 #07 | EVX2 #30 | SOX17 #36 | OHCS2 #18 | Unk09 #09 | EEF1A2 #32 | Unk19 #19 | Unk21 #21 | |
|---|---|---|---|---|---|---|---|---|---|---|---|---|---|---|---|
| | Blood | | | | | | | | | | | | | | Normal Sample |
| Female <55 YO | 30N | | | | | | | | | | | | | | |
| | 24N | | | | | | | | | | | | | | |
| | 27N | | | | | YY | | | | | | | | | |
| | 26N | | YY | | | | | | | | | | | | |
| Male <55 YO | 02N | | | | | BB | | | | | | | | | |
| | 22N | | | | | YY | | | | YY | | | | | |
| | 47N | | | | | YY | | | | | YY | | | | |
| | 01N | | | YY | | | | | | | | | YY | | |
| Female >55 YO | 39N | | | | | YY | | | | | | | YY | | |
| | 17N | | YY | YY | | | | | | | | | | | |
| | 14N | | | YY | | | | | | | | | YY | | |
| | 28N | | YY | | | YY | | YY | | | | | | | |
| Male >55 YO | 12N | | | | | BB | | | | | | | | | |
| | 25N | | YY | YY | | YY | | YY | | | YY | YY | YY | | |
| | 03N | YY | YY | YY | | | | | YY | | YY | | YY | | |
| Smokers | 38N UR93808 | | | | | BB | | YY | YY | YY | | | | | |
| | 49N | | | | | | | | | | | YY | | | |
| | 75N | | | | | YY | | | | | | | | | |
| | 74N | | YY | YY | | | | | | | | | | | |
| | 73N | | | | | | | YY | | | YY | YY | YY | | |
| Bladder Cancer before surgery | 0SS UR5753B | | | YY | | YY | | | | | | | | | Cancer Sample |
| | 29S UR0076B | | YY | YY | | YY | | | | YY | YY | | YY | | |
| | 30S UR0077B | | | | | YY | YY | | | YY | YY | YY | YY | | |
| | 33S UR0089B | | | YY | | BB | | | | YY | YY | | YY | | |
| | 31S UR0078B | | YY | YY | | YY | | | | | | | | | |
| | 25S UR0067B | | YY | YY | | BB | | | YY | | | | YY | | |
| | 02S UR5146B | | YY | YY | | YY | | YY | YY | | | | YY | | |
| | 09S UR0028B | | YY | YY | | BB | | YY | | YY | YY | | YY | | |
| | 37S UR0084B | | YY | YY | | BB | | YY | | YY | YY | | YY | | |
| | 27S UR0072B | | YY | YY | | BB | | YY | | YY | YY | YY | YY | | |
| | 18S UR0029B | | YY | YY | YY | BB | YY | YY | | YY | YY | | YY | | |
| | 41S UR0044B | | YY | YY | | BB | | YY | YY | YY | BB | YY | YY | YY | |
| | 24S UR0057B | | YY | YY | | BB | | YY | YY | YY | BB | YY | BB | | |
| | 20S UR0031B | | YY | YY | BB | BB | YY | YY | YY | YY | YY | YY | YY | | |
| | 22S UR0040B | | YY | YY | BB | YY | | BB | YY | YY | YY | YY | YY | YY | |
| | 08S UR0032B | | YY | YY | YY | YY | YY | BB | YY | YY | YY | BB | BB | YY | |
| | 11S UR0030B | | YY | YY | | BB | | BB | YY | YY | YY | YY | YY | YY | |
| | 01S UR5822B | | BB | BB | BB | BB | YY | BB | YY | YY | BB | BB | BB | YY | |
| | 23S UR0053B | | BB | BB | YY | BB | YY | BB | YY | YY | YY | YY | YY | YY | |
| | 07S UR0026B | | BB | BB | YY | BB | YY | BB | YY | YY | BB | YY | BB | YY | |

TABLE 9-continued

CARE analysis of DNA extracted from urine samples collected from 20 healthy individuals (normal sample; indicated in the upper part of the table) and from 43 patients affected by cancer (cancer sample). The first column indicates the subgroups description (YO = years old), while sample codes are listed in the second column. Markers are indicated in the first row. A blood sample control was included in the analysis (second row) while GAPDH represents the internal digestion control. Methylation levels <0.25% are indicated in white; >0.25% but <1% with YY; >1% with BB. Experiment was performed using two technical replicates.

| | Sample | GAPDH GAPDH | SOX1 #27 | GALR1 #15 | DMRTA2B #10 | Unk05 #05 | Unk07 #07 | EVX2 #30 | SOX17 #36 | OHCS2 #18 | Unk09 #09 | EEF1A2 #32 | Unk19 #19 | Unk21 #21 |
|---|---|---|---|---|---|---|---|---|---|---|---|---|---|---|
| | | | | | | | Markers | | | | | | | |
| 43S | UR9088B | | BB BB | BB BB | BB BB | BB BB | BB BB | BB | YY BB | BB BB | BB BB | YY BB | BB BB | BB BB |
| 26S | UR0068B | | BB BB | BB BB | BB BB | BB BB | BB BB | BB BB | BB BB | BB BB | BB BB | BB BB | BB BB | BB BB |
| 36S | UR9280B | | BB BB | BB BB | | BB BB | BB BB | BB BB | BB BB | BB BB | BB BB | BB YY | BB BB | BB BB |
| 03S | UR6679B | | BB BB | BB BB | BB BB | BB BB | BB BB | BB BB | BB BB | BB BB | BB BB | YY YY | BB BB | BB BB |
| 16S | UR0014B | | BB BB | BB BB | BB BB | BB BB | BB BB | BB BB | BB BB | BB BB | BB BB | YY YY | BB BB | BB BB |
| 37S | UR9349B | | BB BB | BB BB | BB BB | BB BB | BB BB | BB BB | BB BB | BB BB | BB BB | YY YY | BB BB | BB BB |
| 39S | UR0043B | | BB BB | BB BB | BB BB | BB BB | BB BB | BB BB | BB BB | BB BB | BB BB | YY BB | BB BB | BB BB |
| 35S | UR9202B | | BB BB | BB BB | BB BB | BB BB | BB BB | BB BB | BB BB | BB BB | BB BB | BB BB | BB BB | BB BB |
| 04S | UR0008B | | BB BB | BB BB | BB BB | BB BB | BB BB | BB BB | BB BB | BB BB | BB BB | BB BB | BB BB | BB BB |
| 06S | UR0021B | | BB BB | BB BB | BB BB | BB BB | BB BB | BB BB | BB BB | BB BB | BB BB | BB BB | BB BB | BB BB |
| 13S | UR0009B | | BB BB | BB BB | BB BB | BB BB | BB BB | BB BB | BB BB | BB BB | BB BB | BB BB | BB BB | BB BB |
| 14S | UR0012B | | BB BB | BB BB | BB BB | BB BB | BB BB | BB BB | BB BB | BB BB | BB BB | BB BB | BB BB | BB BB |
| 28S | UR0074B | | BB BB | BB BB | BB BB | BB BB | BB BB | BB BB | BB BB | BB BB | BB BB | BB BB | BB BB | BB BB |
| 10S | UR0028A | | BB | BB | BB | YY BB | BB | | | | YY YY | YY YY | YY YY | |
| 19S | UR0029A | | | | | BB | | | | YY | BB | | YY | |
| 21S | UR0031A | | YY YY | YY YY | | BB | | YY YY | | | BB | | BB | |
| 15S | UR0012A | | | BB BB | YY YY | BB BB | YY YY | YY YY | | YY | BB | | BB | YY |
| 45S | UR0044A | | YY BB | YY BB | YY BB | BB BB | YY BB | YY BB | YY BB | YY BB | YY BB | YY | BB BB | BB BB |
| 40S | UR0043A | | BB BB | BB BB | BB BB | BB BB | BB BB | BB BB | BB BB | BB BB | BB BB | BB BB | BB BB | BB BB |
| 12S | UR0030A | | BB BB | BB BB | BB BB | BB BB | BB BB | BB BB | BB BB | BB BB | BB BB | BB BB | BB BB | BB BB |
| 17S | UR0014A | | BB | BB | | | | | YY BB | | | | | |
| 48N | Stomach | | BB | BB | BB | BB | BB | BB | BB | BB | BB | | BB | BB |
| 34S | Colon | | | | | | | | | | | | | BB |

Bladder Cancer after surgery rows: 10S–17S
Non-bladder rows: 48N, 34S

Based on the data obtained from this analysis, a panel marker of #05, #36 and #09 has the highest diagnostic value, therefore they were used for a statistical cancer diagnostic model built utilizing the generalized linear model. This model will classify the population in positive or negative for bladder cancer only based on the data obtained from CARE assay. ¾ and ¼ of the cohort (only the 20 normal and 33 bladder cancer samples were considered) were used as Training and Test Sets respectively and the results are represented in Table 10. Results indicate that the enhanced CARE assay was able to correctly classify most of the Test Set samples (85.71% of the controls and 100% of the bladder cancer samples). In addition, for the Test set the enhanced CARE assay has a sensitivity of 100% and a specificity of 85.71%.

It is also interesting to note that most of the "Bladder cancer sample after surgery" samples were diagnosed as positive by CARE assay (Table 9). This very interesting data support the "field effect" concept and is in agreement with previous data represented in Table 6 in which most of the adjusted normal tissue samples were found to be positive using CARE assay. However it is not clear at this point if the exposition to the cancer environment is also able to trigger epigenetic changes in normal cells present in the vicinity of the tumor. Thus, urine from patients who were subjected to bladder tumor removal will be collected periodically and analyzed using CARE assay to monitor the methylation level evolution of the bladder cancer biomarkers over time.

TABLE 10

Statistical analysis of a 53-individuals cohort affected or not by bladder cancer. The analysis is based on the methylation values detected for marker #05, #36 and #09 using CARE assay. The population is randomly subdivided in Training (3/4) and Test (1/4) Sets and sensitivity % {[TP/(TP + FN)] * 100}, specificity % {[TN/(TN + FP)] * 100}, positive predictive value % {[TP/(TP + FP)] * 100} and negative predictive value % {[TN/(TN + FN)] *100} were calculated for each set and for the whole cohort.

|  |  | Whole Cohort | Training Set | Test Set |
|---|---|---|---|---|
| Data | Total Sample | 53 | 39 | 14 |
|  | Bladder Cancer | 33 | 26 | 7 |
|  | Control | 20 | 13 | 7 |
|  | True Positive (TP) | 30 | 23 | 7 |
|  | True Negative (TN) | 17 | 11 | 6 |
|  | False Positive (FP) | 3 | 2 | 1 |
|  | False Negative (FN) | 3 | 3 | 0 |
| Statistics | Sensitivity % | 90.91 | 88.46 | 100.00 |
|  | Specificity % | 85.00 | 84.62 | 85.71 |
|  | Positive Predictive Value % | 90.91 | 92.00 | 87.50 |
|  | Negative Predictive Value % | 80.95 | 78.75 | 100.00 |

Another interesting result is that the colon adenocarcinoma urine sample (male individuals) was clearly positive for CARE assay. This might be due to the presence of metastasis in the bladder, or again to a "field effect" phenomenon, given the anatomical vicinity of colon and bladder. This second hypothesis is further supported by the fact that the stomach cancer urine sample (#48N; anatomically distant from bladder) was found to be negative with CARE assay.

Concerning the normal urine cohort, no major differences were observed between the different samples except in the subpopulation of healthy males older than 55 years (M>55 YO); in this group, three out of four individuals had a slightly elevated methylation background (generally <1%) in at least half of the biomarkers tested with CARE assay. To note, aging is one of the predominant risk factor for bladder cancer development and the male population (especially Caucasian) is way more affected by this pathology than females. The CARE assay was able to detect slightly increases of methylation in the older male subgroup of the normal cohort which suggests that the CARE assay could discriminate individuals that have more risk to develop bladder cancer from those that do not. In this perspective, it might be also relevant the fact that one out of four female older than 55 years (F>55 YO) also have an elevated methylation level of six biomarkers, while the other three individuals belonging to the same subgroup have a bladder cancer markers methylation profile similar to those seen for younger individuals. To note, all the four smoker young individuals were classified as negative using the enhanced CARE assay.

In conclusion, the enhanced CARE assay was able to correctly classify most of the normal and bladder cancer samples included in the Test set cohort and has a sensitivity and specificity of 100% and 85.71% respectively (Table 9 and Table 10). In addition, the assay detected as positive a urine sample collected from one colon adenocarcinoma affected individuals, indicating that the CARE assay has the potential to detect non-urinary tract cancers using urine samples. Moreover, the assay was able to detect a slight increase of biomarker methylation in the older male (>55 years old) group belonging to the healthy cohort (a risk population concerning bladder cancer development); suggesting that the enhanced CARE assay might represent a potentially interesting tool not only for bladder cancer recurrence diagnosis, but also to better determine the subpopulation with higher risk to develop bladder cancer for the first time.

Example 4—Methods of Enhanced CARE Assay

The enhanced CARE assay of Example 3 has several improvements as compared to the assay of Example 1. First, the reaction buffer of the enhanced CARE assay is compatible with both digestion and qPCR steps. Therefore, the only manual step that the operator needs to do is the addition of the proper amount of template (5-10 ng) to the reaction buffer. After mixing, the reaction will be incubated in the qPCR machine that will automatically perform the digestion and the qPCR steps. This new buffer allows complete digestion in only 2 hours of incubation at 30° C. The reaction mix contains all the components necessary for both steps, including Taq polymerase, the restriction enzymes mix, deoxyribonucleotides, DNA primers and probes, magnesium, additives (e.g., DMSO) and salts, and the optimal concentration of each component was determined in order to maximize CARE assay performances in terms of accuracy, sensitivity and specificity. The best results were obtained using ZymoTaq™ Taq Polymerase, however other Hot-Start enzymes (e.g. AmpliTaq Gold® DNA Polymerase, Phusion® High-Fidelity DNA Polymerase) can be used to prepare the CARE assay reaction buffer.

In addition, the enhanced CARE assay allows multiplexing and the simultaneous analysis up to 5 biomarkers in a single reaction. All the 12 bladder cancer biomarkers and two internal controls present in set A, B and C (described above) were therefore grouped in three multiplex reactions (one for each set; see Table 11). Each amplicon was reviewed and new primers and dual-labeled TaqMan probes were specifically designed in order to maximize the robustness of CARE assay and the overall performances of the system. For each marker the amplification efficiency ranges between 90 and 110% and no significant differences (in terms of amplification efficiencies and background level) can be observed neither when singleplex and multiplex reaction are run in parallel, nor when digestion and qPCR steps are performed in one machine rather than in two separate steps (digestion in a thermocycler or incubator and qPCR in the Real-Time PCR machine). Importantly primers and probes were designed on sequences lacking any annotated SNPs and repeated element. Despite different methodologies and Real-Time machines can be potentially used for the qPCR step, we obtained the best results by combining TaqMan methodology and the CFX96TM-Real Time System (Bio Rad). In the new CARE assay version dual-labeled TaqMan probes are marked with FAM, HEX, Texas Red-X, Cy5 and Quasar 705 and quenched by either BHQ1 or BHQ2 molecules. However, other dyes like Biosearch Blue, TET, CAL Fluor Gold 540, JOE, VIC, CAL Fluor Orange 560, Quasar 570, Cy3, NED, TAMRA, CAL Fluor Red 590, Cy3.5, ROX, CAL Fluor Red 610, Texas Red, CAL Fluor Red 636, Pulsar 650, Quasar 670, Cy5.5, TEX 615, TYE 563, TYE 665, MAX, Yakima Yellow, ABI and JUN and different quenchers like TAMRA, QSY, BHQ2, BHQ3, Iowa Black can be successfully used for the qPCR step. Other system variants, like Molecular Bacons and Scorpions Probes can also be successfully used for the qPCR step.

TABLE 11

The biomarkers present in sets A, B and C (right column for each set) were multiplexed. Each multiplex reaction is able to amplify up to 5 markers simultaneously. Set A and B contain the markers with the best performances and the two internal controls POLR2A and GAPDH, while set C contains all the other markers. Dies and quenchers used for each marker are indicated in the right column of each set. Q705 = Quasar 705, TR = Texas Red, BHQ = Black Hole Quencher.

| SetA | | SetB | | SetC | |
|---|---|---|---|---|---|
| POLR2A | Q705-BHQ2 | #05 | TR -BHQ2 | #09 | Cy5-BHQ2 |
| GAPDH | FAM-BHQ1 | #07 | Cy5-BHQ2 | #32 | Q705-BHQ2 |
| #27 | TR-BHQ2 | #30 | Q705-BHQ2 | #19 | HEX-BHQ1 |
| #15 | HEX-BHQ1 | #36 | HEX-BHQ1 | #21 | TR-BHQ2 |
| #10 | Cy5-BHQ2 | #18 | FAM-BHQ1 | | |

A third important improvement that was made in the enhanced CARE assay is the increase of the number of restriction sites that are investigated for each amplicon. The newly designed amplicons contain at least 6 different restriction sites that are targeted at least by two out of three restriction endonucleases selected for this assay (AciI, HinP1I and HpaII). This, combined with the innovative chemistry of the new reaction mixture, ensures a complete digestion in 2 hours (Table 13) and minimizes the risk to incurring in artifacts and unspecific background signal.

In addition, all oligonucleotide (primers and probes) sequences do not contain consensus motives for the aforementioned restriction endonucleases; this seems to prevent the degradation (although very slight) of the oligonucleotides during the digestion reaction potentially caused by the temporary and probably only partially specific interactions with other DNA molecules that might occur at the digestion temperature (30° C.).

Several other restriction enzymes, including AatII, Acc65I, AccI, AciI, AclI, AfeI, AgeI, AhdI, AleI, Apal, ApaL1, ApeK, AscI, AsiSI, AvaI, AvaII, BaeI, BanI, BbvCI, BceAI, BcgI, BcoDI, BfuAI, BfuCI, BglI, BmgBI, BsaAI, BsaBI, BsaHI, BsaI, BseYI, BsiEI, BsiWI, BslI, BsmAI, BsmBI, BsmFI, BspDI, BspEI, BsrBI, BsrFI, BssHII, BssKI, BstAPI, BstBI, BstUI, BstZ17I, BtgZI, Cac8I, ClaI, DpnI, DraIII, DrdI, EaeI, EagI, EarI, EciI, Eco53kI, EcoRI, EcoRV, FauI, Fnu4HI, FokI, FseI, FspI, HaeII, Hgal, HhaI, HincII, HinfI, HinPII, HpaI, HpaII, Hpy 166II, Hpy188III, Hpy99I, HpyAV, HpyCH4IV, KasI, MboI, MluI, MmeI, MspAlI, MwoI, NaeI, NarI, NciI, NgoMIV, NheI, NlaIV, NotI, NruI, Nt.BbvCI, Nt.BsmAI, Nt.CviPII, PaeR7I, PhoI, PleI, PluTI, PmeI, PmlI, PshAI, PspOMI, PspXI, PvuI, RsaI, RsrII, SacII, SalI, Sau3AI, Sau96I, ScrFI, SfaNI, Sfi1, SfoI, SgrAI, SmaI, SnaBI, StyD4I, TfiI, TliI, TseI, TspMI, XhoI, XmaI, ZraI can in principle be utilized for the CARE assay.

Controls:

Another core component of the enhanced CARE assay is represented by the controls. The actual CARE assay version contemplates 4 different controls: A) endogenous copy number control (POLR2A), B) endogenous digestion control (GAPDH), C) undigested sample control and D) exogenous digestion control (standardized blood sample). To note, the controls used for CARE assay are not manipulated in vitro (e.g. chemically or enzymatically modified) reducing in that way the chances to introducing artefacts and errors.

Endogenous Copy Number Control—POLR2A:

One point for the reliability of the assay is the normalization of the signal obtained from each marker against the amount of DNA sample loaded in each reaction. Tiny differences in the amount of template loaded in different reactions are common in qPCR and they can impact the results of the analysis if they are not monitored. Because of that the usage of an internal copy number control that allows to precisely quantitate the amount of template used in each reaction and to correct the values obtained from the analysis is needed. A portion of the coding sequence of the human POLR2A gene was chosen as the copy number control. That choice was made because A) POLR2A is an essential gene, so the control signal will always be detected, B) this control marker is a single-copy gene and its usage in multiplex qPCR will not interfere with the amplification of the other markers (like what can happen using a multi-copy marker like a transposable element), C) the sequence that was selected does not contains target sites for any of the restriction endonucleases used in the assay, so the signal of the copy number control will always reflects the amount of DNA used independently on the fact that the sample is digested or not. In principle, every locus satisfying the three points listed above can be successfully used as endogenous copy number control.

Endogenous Digestion Control—GAPDH:

One other point for the reliability of CARE assay is the achievement of a complete enzymatic digestion. In principle, a single cleavage event within a specific locus is sufficient to prevent the amplification of the associated target region. Nevertheless, as described previously, amplicons were designed in order to include at least 6 restriction sites recognized by at least two out of the three restriction endonucleases used for the assay. This, combined with the new reaction mix composition, allows the achievement of the maximum specific enzymatic activity and strongly abates the possibility of incomplete digestion. However, the digestion completeness of each reaction was monitored by including in the final CARE assay an endogenous digestion control. This is represented by a DNA locus that is A) essential for the cell survival, B) that contains multiple restriction sites for all of the three enzymes used in the CARE assay C) and that is always unmethylated in any type of cells and tissues. The internal digestion control was designed on the CpG island of the human GAPDH gene; this housekeeping gene have an essential role in glycolysis and is widely used as a copy number control for gene expression analysis in RT-qPCR reactions and immunoblots since it is always expressed at almost constant level in all the cell type. In all of the digested samples tested with CARE assay (a wide variety of specimen including biological fluids, tissues and cell types) GAPDH signal was always lower than the maximum acceptable background level (1%) and in most of the case it was not detectable at all (e.g. in Table 5). Also, in this case, loci that satisfy the three points aforementioned can be used as endogenous digestion controls; between all, possible alternative endogenous digestion control loci can be designed on CpG islands of genes ATP5C1, TBP, GARS, LDHA and PGK1.

Undigested Sample Control:

This control consists of a DNA sample processed exactly like the samples that will be subjected to digestion, but without adding the restriction endonucleases mix. Therefore, in this sample, the DNA will remain intact and all the marker copies added initially to the reaction will be suitable for amplification. The amplification signal for each marker in this sample can therefore be considered 100%, and the percentage of methylated (uncut) marker detected in the parallel digested sample will be calculated accordingly. Initially, a DNA sample isolated from a healthy blood donor was used as the undigested sample control. However, to minimize the possible differences that might exist between this standard sample and urine DNA samples, an undigested reaction (run in parallel with the digested ones) was performed for each urine sample that will be analyzed with CARE assay. Thus, the final assay will therefore include two distinct premixed reaction solutions, named D and U, for each marker set; only the reaction solution D (but not the U) will contain the restriction nucleases mix needed for the digestion step. In general, it was concluded that running an undigested control for each single sample represents the most reliable way to precisely quantify the amount of methylation level for each marker in each sample.

To further increase the precision of the assay, a second digestion control represented by a standardized sample of blood DNA was included. The fact that all the cancer markers included in the current assay are not (or only weakly) methylated in blood DNA (Table 12) allows the detection of potential problems that might occur during the digestion step and that are listed below:

A) Different markers are cleaved by a different combination of restriction endonucleases (some markers are cleaved by all three enzymes, some other just by two); moreover, a different number of CpG dinucleotides are interrogated in different markers (ranging from 6 to 12). Therefore, although sufficient, the evaluation of the digestion efficiency using only the GAPDH control marker will be imprecise (GAPDH locus is targeted at 6 different sites by all 3 restriction endonucleases). In an extreme unlikely situation in which only one out of three enzymes is fully active, GAPDH control will be completely digested, while cancer markers that are targeted only by the two other enzymes will be only partially digested. This will leads to an unreal increase of some cancer marker methylation status, generating a possible false positive situation. The abnormal increase of methylation for some cancer markers in the E.D.C. control will immediately inform the operator about this situation B) Moreover, if a general increase in methylation background level (including for the GAPDH endogenous digestion control) is observed for a specific sample, it will be impossible to know (in absence of the E.D.C.) if that is caused by a decreased activity of the restriction enzymes (in that case the reaction mix need to be substituted with a new batch) or by a poor quality of the DNA sample (in this second case the sample needs to be purified). Since the quality of the exogenous digestion control is standard and all the markers in this sample are unmethylated, an increase of the background level for all the markers in the exogenous digestion control will clearly indicate that the enzymatic activity of the restriction enzymes present in the reaction mixture is impaired and the mix has to be replaced with a new batch.

TABLE 12

CARE assay analysis of the exogenous digestion control (standardized blood DNA). Markers are listed in the first column. Values for each marker are expressed as percentage of methylation present after digestion. GAPDH represents the internal digestion control. Values that exceed 0.25% (low-confidence background limit) are underlined. Experiment was performed using three technical replicates.

|  | GAPDH | E.D.C. 0.05 |
|---|---|---|
| Markers | #27 | 0.12 |
|  | #15 | 0.06 |
|  | #10 | 0.03 |
|  | #05 | <u>0.71</u> |
|  | #07 | 0.06 |
|  | #30 | 0.10 |
|  | #36 | 0.03 |
|  | #18 | 0.04 |
|  | #09 | 0.02 |
|  | #32 | 0.04 |
|  | #19 | <u>0.28</u> |
|  | #21 | 0.03 |

In addition to the four controls aforementioned, information was collected to monitor different biochemical parameters of the urine sample before proceeding with the DNA extraction. The primary reason was to determine the possible influences of specific conditions (e.g. the increased presence of proteins and ketones in the urine, the urine pH value, etc.) on the CARE assay performances. Secondly, other parameters can perhaps support CARE assay diagnosis.

An analysis was performed using Multistix® 10 SG Reagent Strips (Siemens). None of the parameters monitored with this tool have an impact on the CARE assay performances. Moreover, hematuria, high leukocyte and protein content was detected in the majority of the urine collected from bladder cancer patients but not in urine collected from healthy individuals.

Figure 17A:
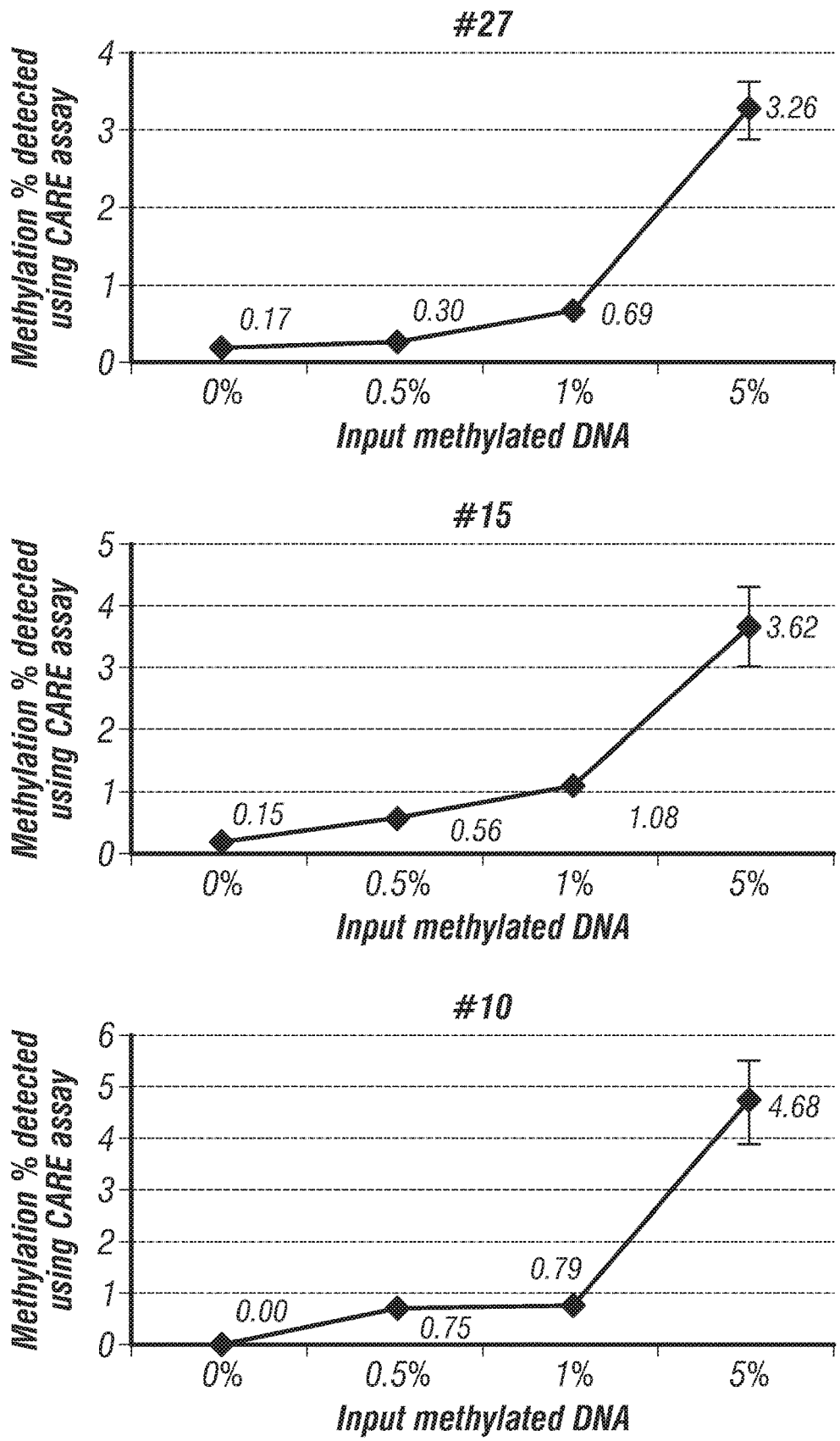
FIGS. 17A-17B: CARE assay analysis of a normal urine DNA sample added with different amount of artificially methylated urine DNA (100% methylated; X axis). A) CARE assay is able to detect the presence of 0.5% of fully methylated urine DNA in an unmethylated urine DNA background. B) CARE assay performances when 50% and 100% of artificially methylated urine DNA is added to a normal urine DNA sample. 10 ng of input DNA were used in each reaction (the DNA amount approximately corresponding approximately to 1500 cells). For simplicity only cancer marker belonging to set A are represented. Experiment was performed using three technical replicates.
Figure 17B:
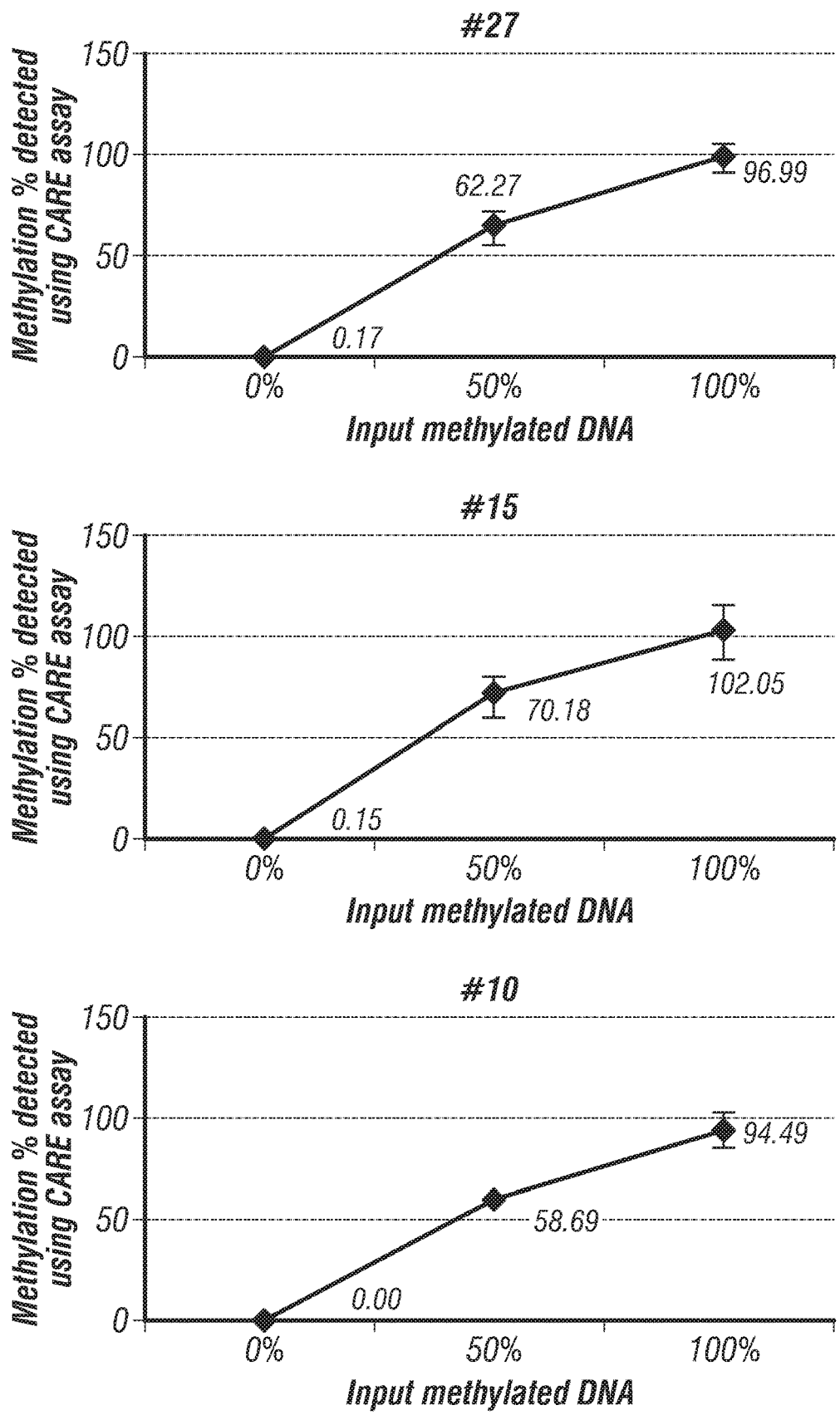

One of the most remarkable characteristics of CARE assay consists in the combination between high performances (in terms of robustness, detection limit, sensitivity and accuracy) and extreme simplicity and versatility. Indeed, based on the data obtained so far, the CARE assay has a sensitivity of at 100% and a specificity of 85.71% (Table 11). In addition, CARE assay has a remarkably low detection limit; indeed, it is able to detect with confidence less than 7 cancer cells in a sample containing more than 1500 cells (as shown in FIG. 17).

On the other hand, the CARE assay is very simple, rapid, and user friendly. The whole assay (including digestion, qPCR step and data analysis) can be performed in less than 5 hours. For each marker set, two premixed reaction solutions (D and U) and the exogenous digestion control sample (E.D.C.) will be provided (FIG. 18). Both reaction mixes will contain all the components necessary to perform the qPCR step, but only the reaction solution D (but not the U)

will contain the restriction nucleases mix needed for the digestion step. Therefore, the user only has to add 5 to 10 ng of sample DNA (or E.D.C. sample) to 15 µl of each reaction solution and adjust the volume to 20 µl using the DNA Diluent Buffer provided with the kit. After mixing, the reactions will be directly incubated in a CFX96TM-Real Time System Machine (Bio Rad) that will perform the digestion and qPCR steps as well as the data analysis in less than 4 hours (complete digestion can be achieved after only 2 hours of incubation at 30° C.; see Table 13).

TABLE 13

CARE assay results from reactions in which a normal urine sample was incubated for 0, 2, 4, 8 and 16 hours at 30° C. in the CFX96TM-Real Time System Machine before starting the qPCR step. Complete digestion (background < 1%) is achieved after only 2 hours of incubation. For practicality only marker belonging to set A were analyzed. Values of each marker are expressed in methylation percentage after digestion, with the exception of POLR2A for which mean CT vales are indicated. Experiment was performed using three technical replicates.

|         |            | Digestion Time |       |       |       |       |
|---------|------------|----------------|-------|-------|-------|-------|
|         |            | 0 h            | 2 h   | 4 h   | 8 h   | 16 h  |
| Markers | POLR2A (CT)| 24.89          | 24.51 | 24.49 | 24.43 | 24.62 |
|         | GAPDH      | 100            | n.a.  | 0.01  | 0.00  | n.a.  |
|         | #27        | 100            | 0.27  | 0.16  | 0.21  | 0.17  |
|         | #15        | 100            | 0.22  | 0.15  | 0.12  | 0.09  |
|         | #10        | 100            | n.a.  | 0.04  | n.a.  | 0.04  |

The stability of both reaction mixes D and U were tested and found to be stable for several months at −20° C. Moreover, 10 thaw/freeze cycles did not alter the reaction performances (Table 14).

TABLE 14

CARE analysis using reaction mixes D and U thawed and frozen multiple times. No significant increase of background (impaired digestion activity) or decrease in amplification efficiency (impaired Taq polymerase activity; observable by comparison CT values of the internal copy number control POLR2A) was detected. No Tw-Fz = reaction mixes not subjected to thaw-freeze cycles; 5 × Tw-Fz = reaction mixes thaw and frozen for 5 times; 10 × Tw-Fz = reaction mixes thaw and frozen for 10 times. Values of each marker are expressed in methylation percentage after digestion, with the exception of POLR2A for which mean CT vales are indicated. Experiment was performed using three technical replicates.

|         |             | Treatment |           |            |
|---------|-------------|-----------|-----------|------------|
|         |             | No Tw-Fz  | 5 × Tw-Fz | 10 × Tw-Fz |
| Markers | POLR2A (CT) | 27.13     | 0.13      | 27.17      |
|         | GAPDH       | 0.03      | 27.13     | 0.03       |
|         | #27         | 0.27      | 0.27      | n.a.       |
|         | #15         | 0.27      | 0.14      | n.a.       |
|         | #10         | 0.33      | 0.14      | n.a.       |

To obtain the CARE assay performances described above, the urine DNA quality (in terms of purity and integrity) should be high enough to guarantee an efficient digestion and amplification during the digestion and qPCR step respectively. Therefore, a preservative agent (UCB™, Zymo Research) was added immediately after the urine collection in order to prevent nucleic acids degradation before the DNA isolation step. It was observed that the addition of UCB™, while well preserving the DNA integrity in the sample over time (Table 15), did not interfere with the CARE assay performance when Quick-DNA™ Urine Kit (Zymo Research) was used to isolate the DNA (Table 15).

TABLE 15

CARE analysis (marker set A) using DNA extracted from fresh urine (No UCB) and from urine stored with UCB for one week (UCB 7 days) or one month (UCB 30 days). The urine necessary for this experiment derives from a single donation of a single individual. No substantial changes in methylation background, or amplification potential (POLR2A CT values) can be observed between the different samples. Values of each marker are expressed in methylation percentage after digestion, with the exception of POLR2A for which mean CT vales are indicated. Experiment was performed using three technical replicates.

|         |             | Treatment |            |             |
|---------|-------------|-----------|------------|-------------|
|         |             | No UCB    | UCB 7 days | UCB 30 days |
| Markers | POLR2A (CT) | 27.34     | 27.21      | 27.01       |
|         | GAPDH       | n.a.      | n.a.       | n.a.        |
|         | #27         | 0.10      | 0.40       | 0.11        |
|         | #15         | 0.16      | 0.04       | n.a.        |
|         | #10         | n.a.      | n.a.       | n.a.        |

As mentioned before, the DNA quality might represent a key prerequisite for a successful CARE assay analysis. Therefore, it was decided to test if different urine DNA isolation kits are equally able to provide DNA with a sufficient quality to perform CARE assay. Three kits (Quick-DNA™ Urine Kit-Zymo Research-, Supplier QI and Supplier NG) were tested in parallel using a single urine sample with or without UCB™ 2 hours before the extraction (Table 16). When DNA was isolated with different kits no substantial differences were observed neither in the total amount of DNA recovered (DNA was quantified using Femto™ Human DNA Quantification Kit, Zymo Research; data not shown), nor in the DNA amplification potential (CT mean values for POLR2A internal control in different CARE reactions are very similar; Table 16). Surprisingly, however, the quality of the DNA isolated using the kit of Supplier NG is not sufficient to obtain good CARE assay performance. In particular for the internal digestion control GAPDH and marker #27 the methylation background level is above the high confidence limit (1%). Moreover, this problem is further pronounced in the sample added with UCB™ (Table 16). This indicates that while the quality of the DNA isolated with different kits is sufficient for the qPCR step, the same is not true for the digestion step. Therefore, it was concluded that a very high DNA quality is a prerequisite for a successful CARE assay.

TABLE 16

CARE assay compatibility with upstream sample manipulations. While all three kits are able to isolate urine DNA with a quality suitable for qPCR (the CT values of the internal copy number control are very similar), only Quick-DNA™ Urine Kit (Zymo Research) and supplier QI-isolated DNA is suitable for CARE assay (digestion and qPCR steps). DNA isolated with Supplier NG kit has an increased methylation background, especially when UCBTM is added to the urine sample (+UCB; underlined cell entries). Values of each marker are expressed in methylation percentage after digestion, with the exception of POLR2A for which mean CT vales are indicated. Experiment was performed using two technical replicates. −UCB = No UCBTM added; +UCB = UCBTM added.

|         |            | −UCB  | +UCB  | −UCB  | +UCB  | −UCB  | +UCB  |
|---------|------------|-------|-------|-------|-------|-------|-------|
| Markers | POLR2A (CT)| 27.66 | 27.14 | 27.21 | 27.09 | 27.35 | 26.91 |
|         | GAPDH      | 0.06  | 0.05  | 0.05  | n.a.  | _1.07_ | _3.87_ |
|         | #27        | 0.26  | 0.14  | 0.39  | 0.40  | _1.77_ | _2.62_ |
|         | #15        | 0.61  | 0.48  | 0.47  | 0.31  | 0.73  | 0.57  |
|         | #10        | n.a.  | 0.12  | 0.01  | n.a.  | n.a.  | n.a.  |

Figure 20:
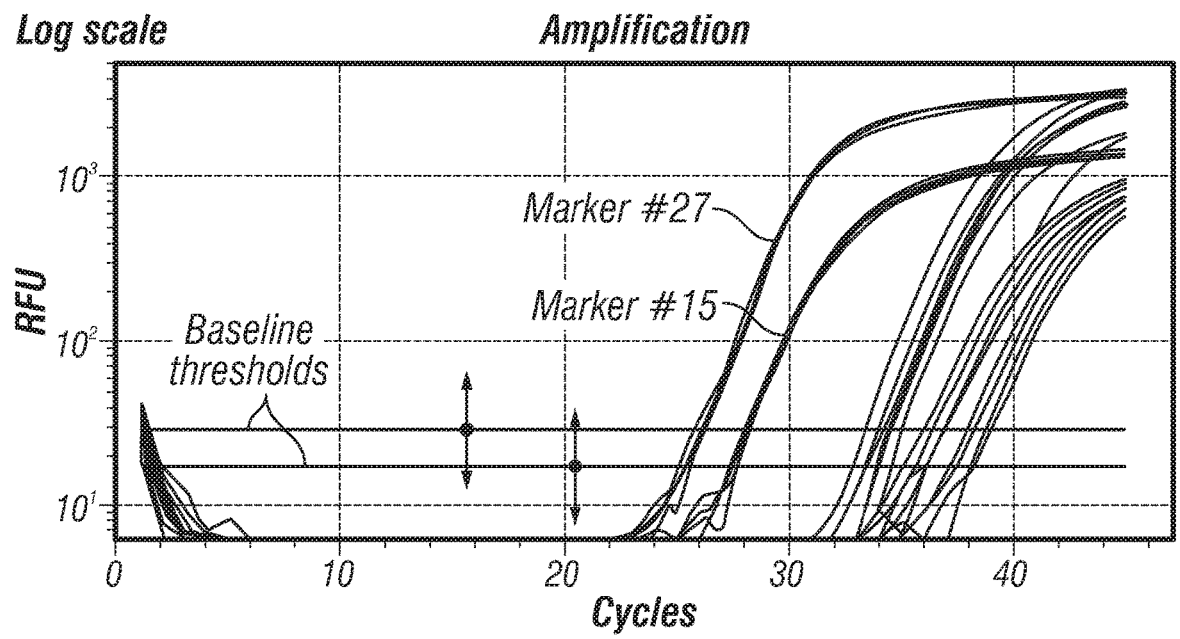
FIG. 20: Example of adjustment of the baseline threshold values for marker #27 and #15.

Algorithm Used for Data Analysis:

As mentioned above, the CFX96™-Real Time System Machine will perform also the data analysis based on the ΔΔCT algorithm. Briefly (an example is represented in FIG. 19), for each sample the mean CT values (mean Cycle Threshold; FIG. 04A) obtained for each marker will be first normalized against the mean CT value of the copy number control POLR2A (obtaining in that way the ΔCT value; FIG. 19B). Afterward, for each marker, the ΔCT value of the undigested sample (reference sample) will be subtracted to the ΔCT value of the digested sample, obtaining in that way the ΔΔCT value (FIG. 19C). At this point relative quantification values (RQs; in our case represents the relative methylation level) will be easily calculated by applying the formula "RQ=2^−ΔΔCT" (FIG. 19D). The operator will only have to adjust (when needed) the baseline threshold for each marker (FIG. 20), exclude from the analysis the eventual outlier technical replicates and make sure that the values obtained from the digestion controls are between the acceptable ranges. Methylation level in the digested sample will be represented as percentage of the value obtained in the undigested sample (100%; FIGS. 19E and F).

Alternatively, the degree of methylation for each marker can be expressed in methylated DNA copies (resistant to digestion). From this perspective, it should be considered that when 10 ng of DNA are used (the DNA amount derived from approximately 1500 cells, that correspond to 3000 DNA copies), the signal obtained from the undigested sample is derived from the amplification of 3000 DNA copies, while the signal detected in the digested sample (DNA copies derived from cancer cells) can be calculated accordingly.

Moreover, the signal obtained from the analysis of each sample and marker can be corrected for the average background signal level obtained from each single marker in a normal urine cohort. This will further increase the precision of the analysis, however a larger and properly selected normal urine cohort has to be analyzed using CARE assay in order to establish the most reliable correction value to apply for each single marker.

Thus, provided herein is a unique combination of cancer-specific biomarkers and an optimized system design that renders this assay a robust, accurate, sensitive, non-invasive and very simple epigenetic-based method for the early detection of bladder cancer from urine samples. Thanks to the newly designed reaction mix and to the high degree of automation a complete analysis using CARE assay can be performed in less than 5 hours with minimal sample manipulation. Moreover, the unique combination of endogenous and exogenous controls, the meticulous amplicon design and the optimized reaction chemistry makes this system incredibly robust, reproducible and accurate. CARE assay have a sensitivity of 100%, a specificity of 85.71% and a very low detection limit (less than 7 cancer cells can be detected in a sample containing more than 1500 cells). In addition, the CARE assay has the potential to detect chromosomal aneuploidies, tumor type other than bladder cancer and perhaps to individuate persons who have the highest risk to develop bladder cancer for the first time.

Example 5—Analysis of Methylation Using MMSP Assay

In order to precisely detect a predisposition to, or the incidence of bladder cancer with limited biopsy or liquid biopsy samples from patients, a highly sensitive and specific multiplex assay was developed to analyze the number of methylated DNA molecular in a vast un-methylated background.

Figure 21A:
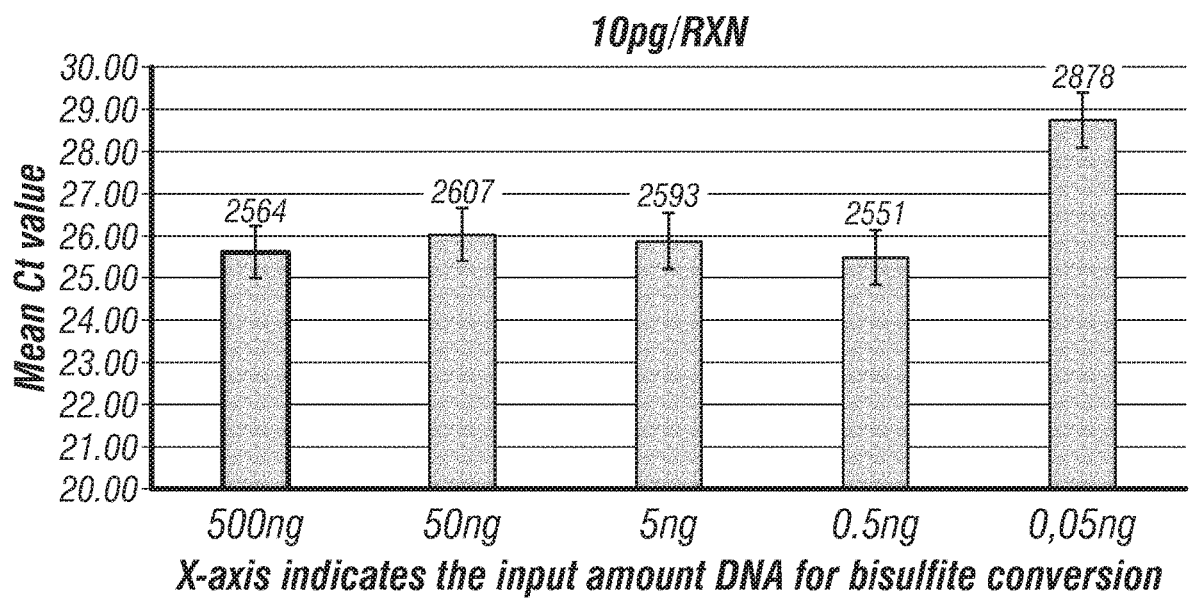
FIG. 21A: Analysis of input amount of DNA for bisulfite conversion in Multiplex methylation-specific qPCR assay (MMSP).

Bisulfite Conversion:

Genomic DNA extracted from patients' biopsy samples, including urine, blood or tissues samples, was bisulfite converted. As a standard methodology for DNA methylation study, bisulfite conversion uses chemistry to specifically convert unmethylated cytosine residues to uracil, allowing the use of polymerase chain reaction to selectively amplify methylated genome DNA from unmethylated DNA. The conversion efficiency of this assay is more than 99.5% and the lowest input amount of gDNA for bisulfite conversion is 50 pg DNA, thus the assay is feasible for processing as low as 10 diploid cells (FIG. 21).

PCR Design:

The primers and probes to target the biomarker genome regions were designed under guidelines which consider melting temperatures (Tm) (identical Tm=58-60° C. for primers and Tm=68-70° C. for probes), length of probes (less than 30 bp) and CG ratio (30-80%) of primers and probes. In addition, the number of CpG dinucleotides covered by primers and probes was carefully controlled. For example, at least 7 CpG loci should be covered by one group of primers and probes to achieve the desired specificity of this assay. The position of CpG dinucleotides on primer and probes was also considered (e.g., at least one C in the last 5 nucleotides the 3' end of primers)

Figure 21B:
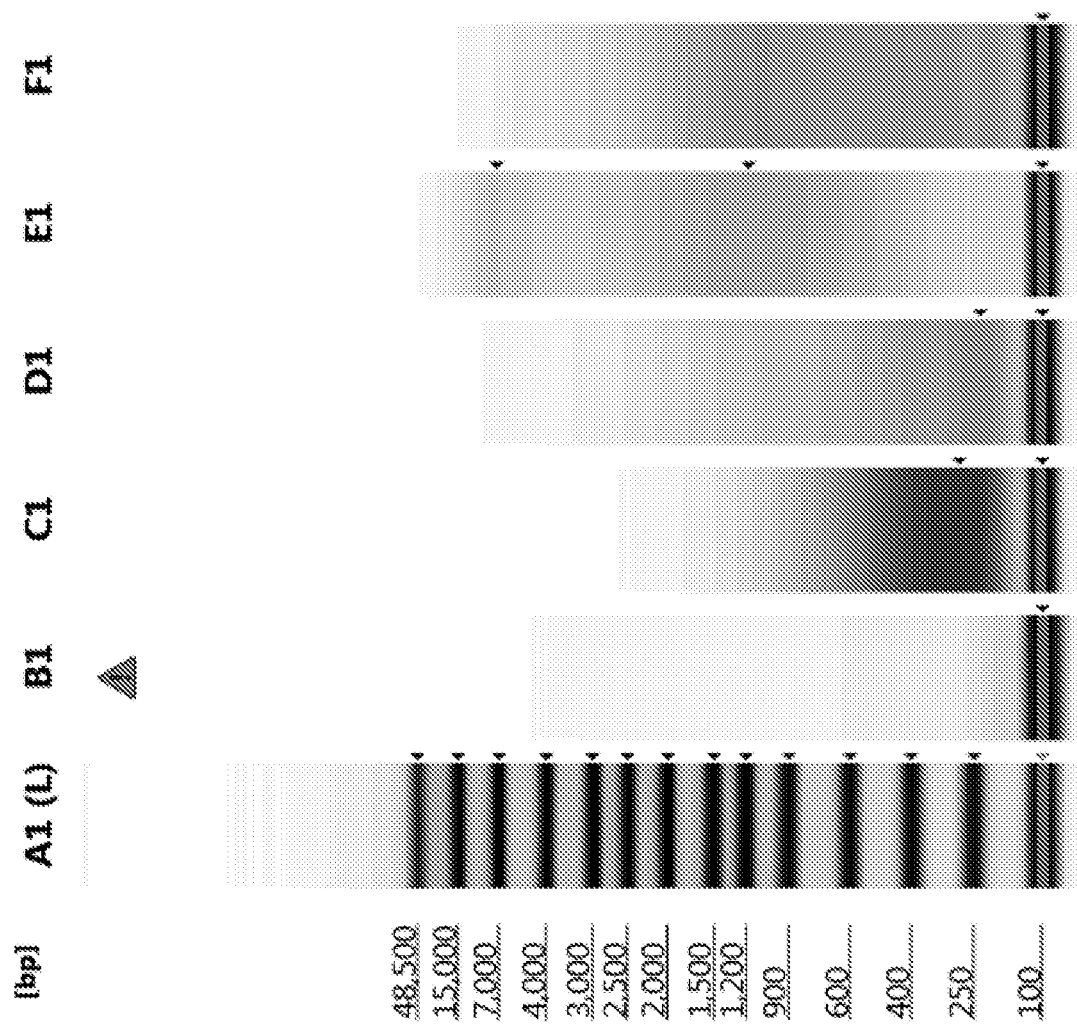
FIG. 21B: Urine DNA size distribution of four random selected bladder patient samples.
Figure 22:
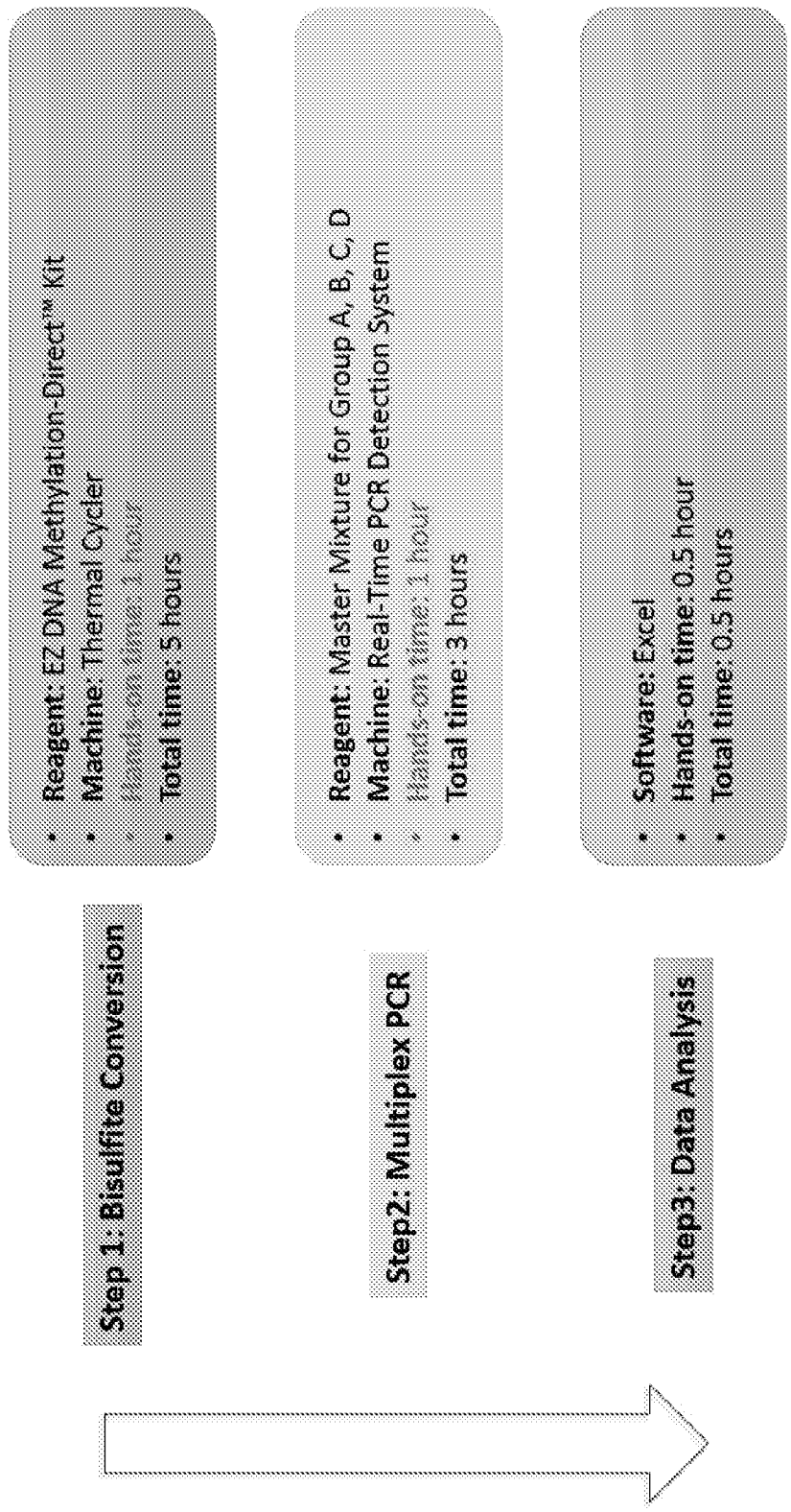
FIG. 22: Schematic depicting MMSP assay working flow including bisulfite conversion, multiplex real-time PCR and data analysis all performed in one day.

To overcome the size variance of DNA fragments in biopsy samples, the length of PCR amplicon was limited to 130 bp to 150 bp to avoid missing small fragment DNA in urine samples. (FIG. 21B; see Yang et al., 2010). The sixteen best performing target regions from the upstream statistical analysis were divided into 4 groups as following.

Group A: DMRTA2, EVX2, Unk21, OTX1, CNC
Group B: SOX1, SEPT9, Unk05, Unk09, CNC
Group C: GALR1, Unk07, Unk19, TBX15, CNC
Group D: EEF1A2, TFAP2B, DCHS2, SOX17, CNC Controls:

The internal copy number control (CNC) of the assay is collagen type II, alpha 1 gene (COL2A1), which is a single copy gene. The entire amplicon of COL2A1 is devoid of any CpG dinucleotide in the original genome sequence. Therefore, the amount of input DNA can be measured for each reaction regardless of the methylation status of template DNA (Widschwendter et al., Cancer Research, 64: 3807-3813, 2004). Thus, for each group, the CNC reaction was included to check for sample quantity and integrity in the same reaction well.

Figure 24:
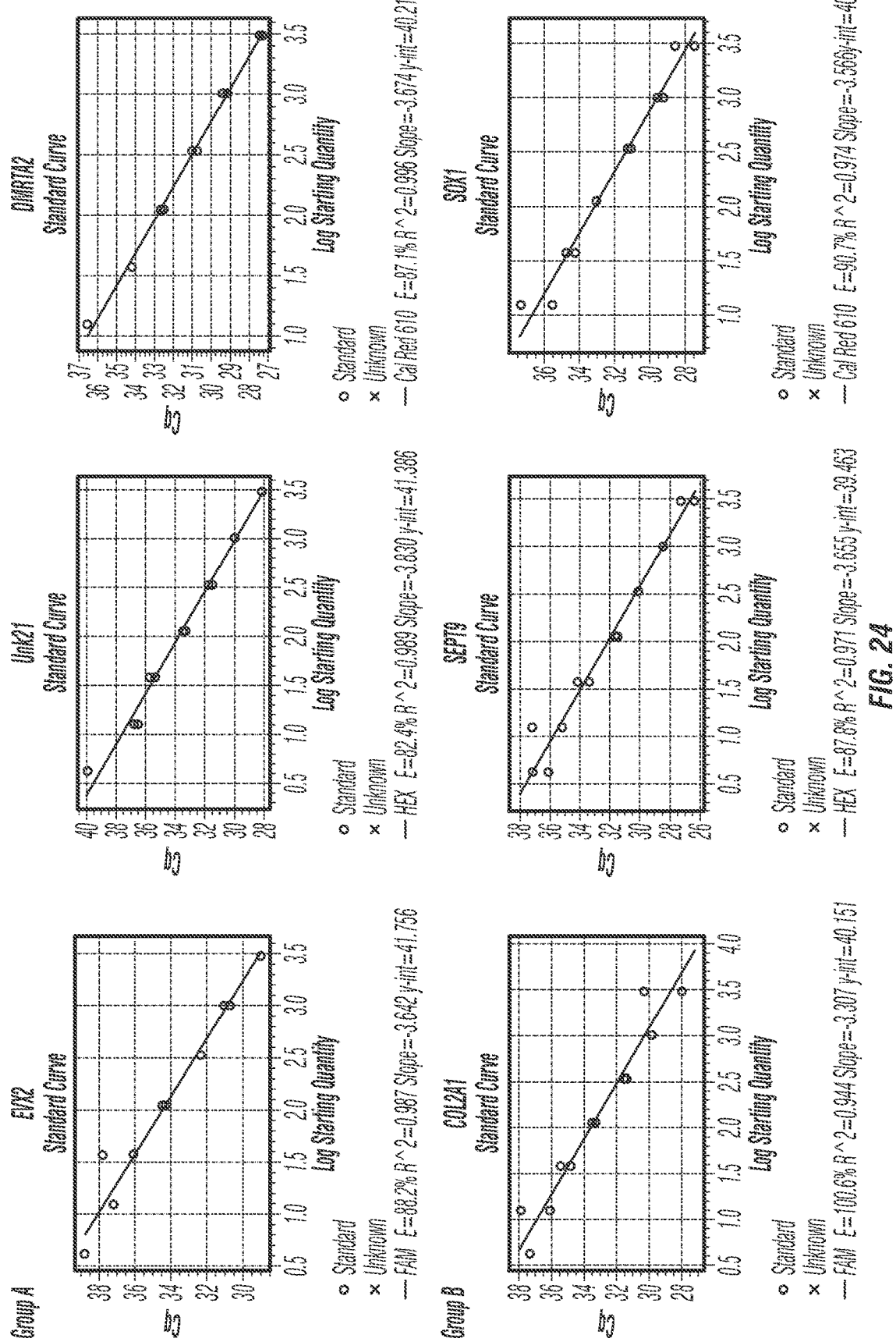
FIG. 24: Standard curves and PCR efficiency for each group A-D of each target regions for MMSP assay.
Figure 24:
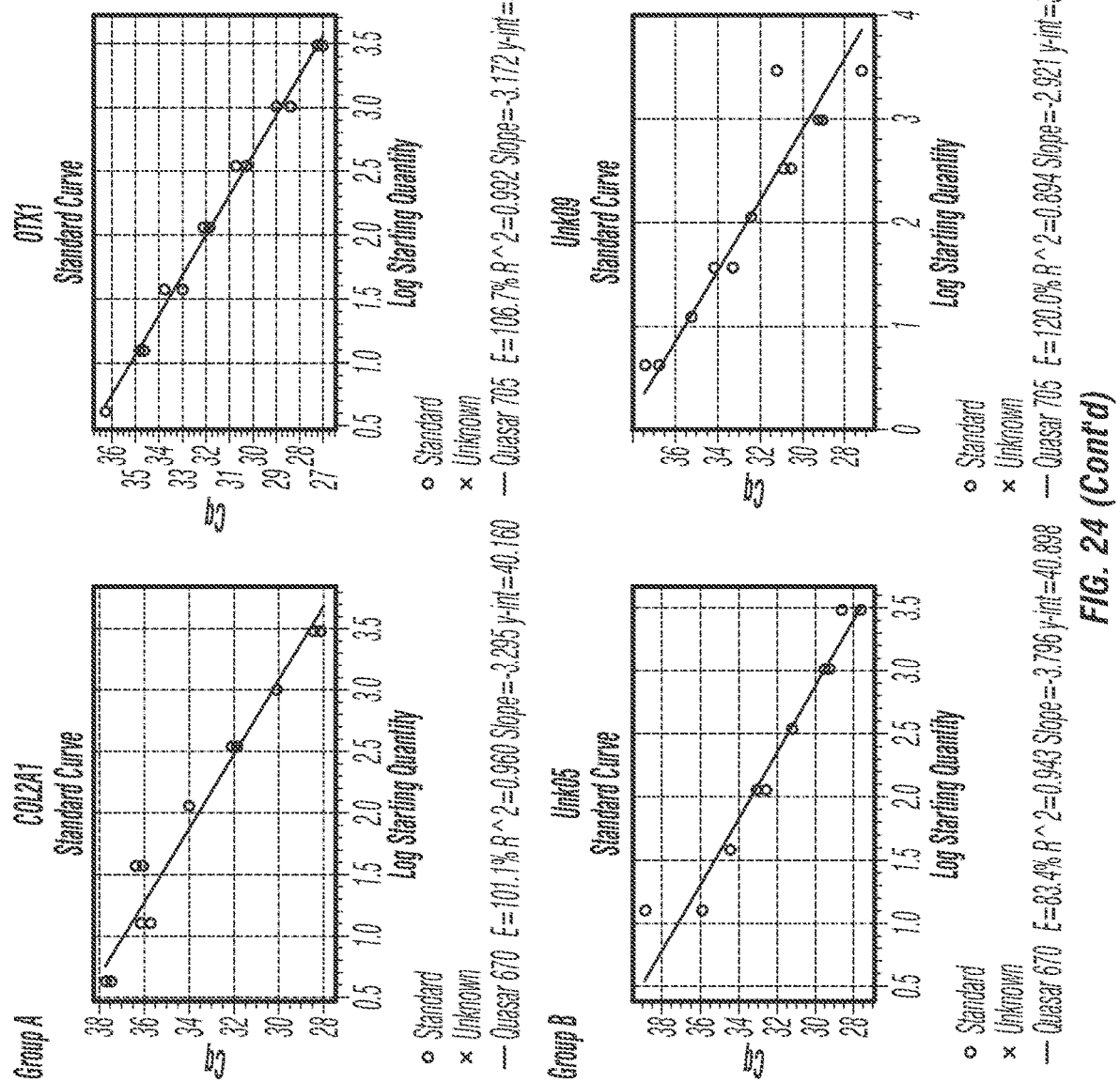
Figure 24:
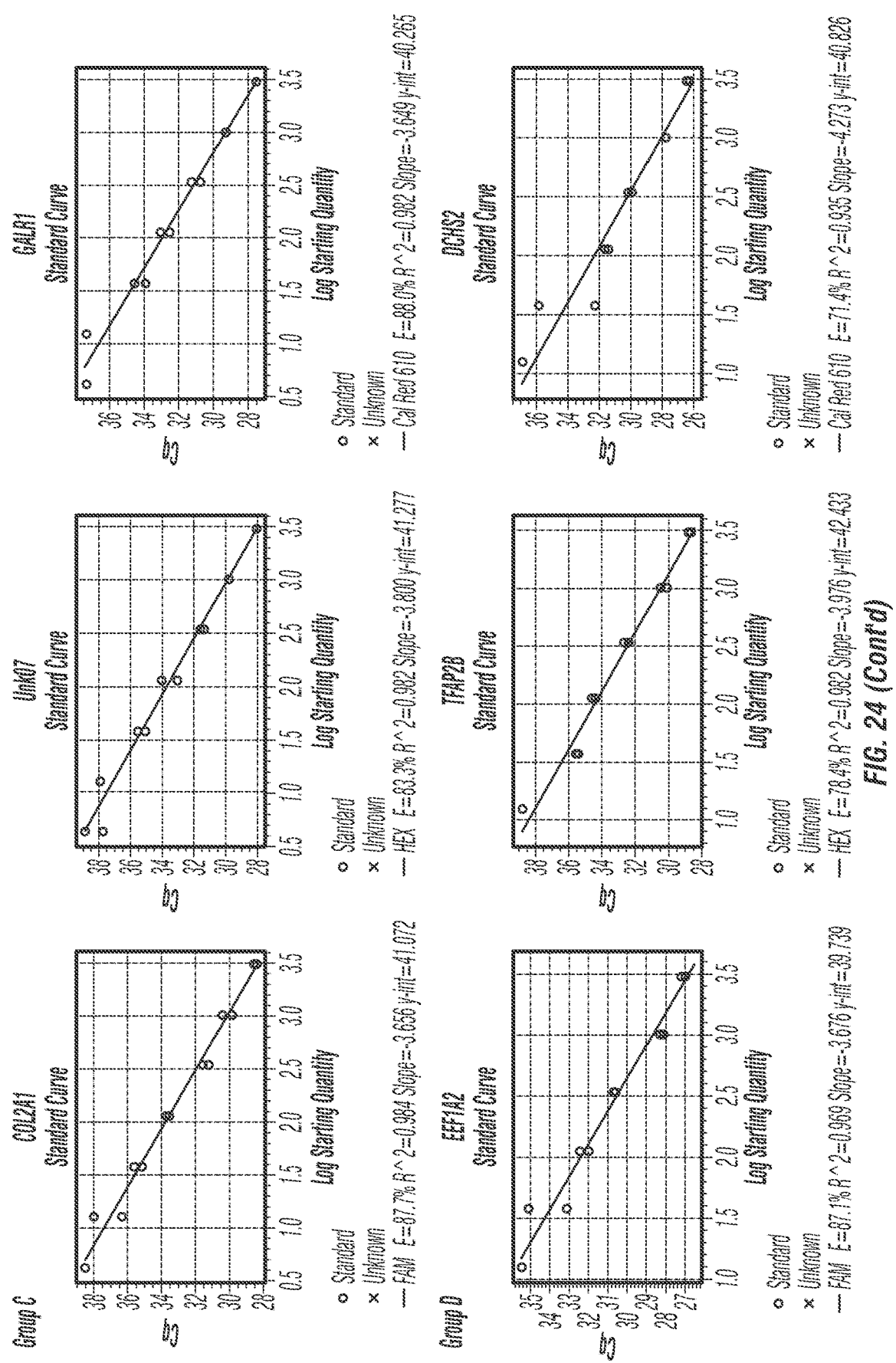
Figure 24:
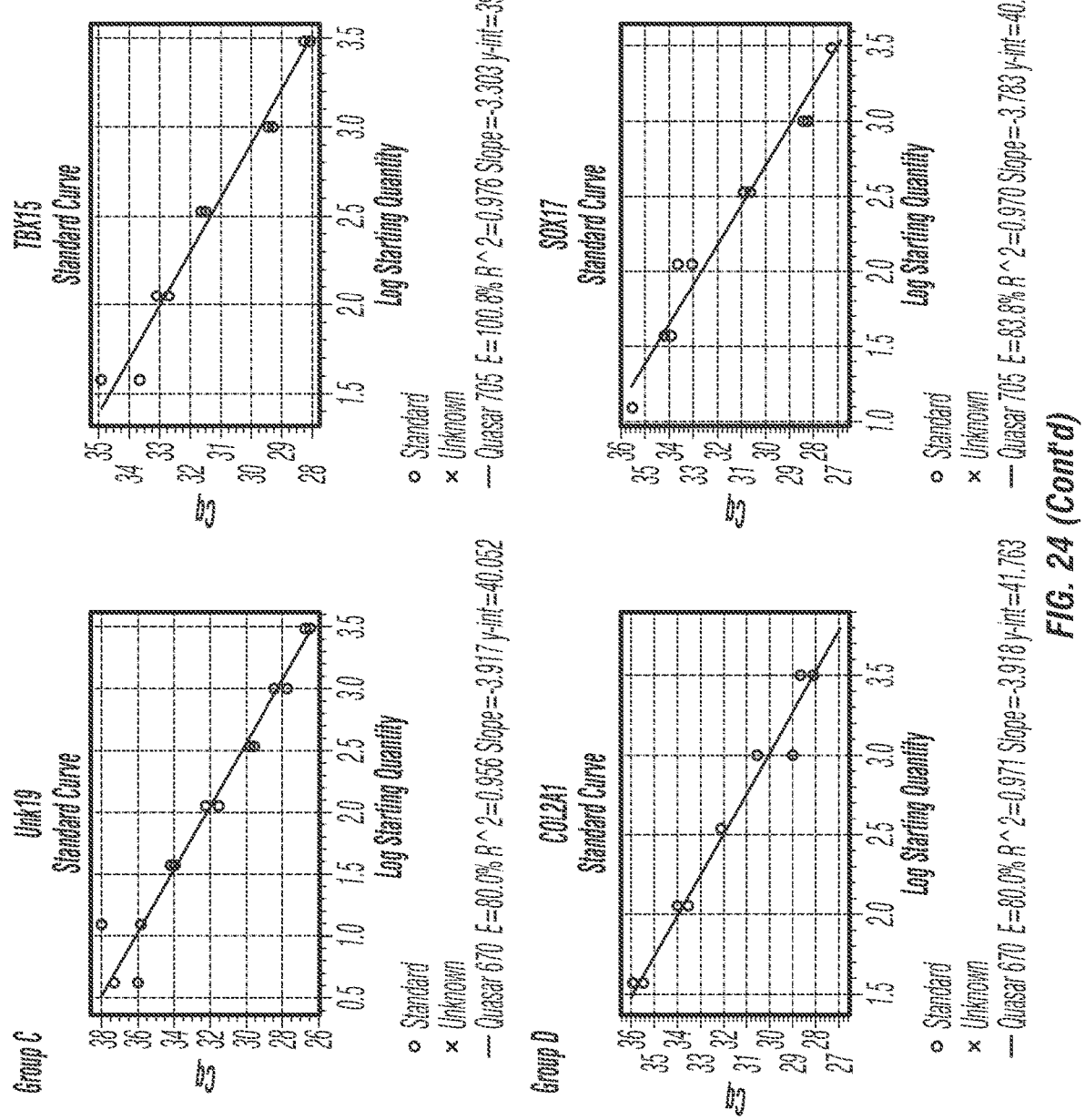

M.SssI-modified gDNA (D5014-2) was used as a positive control of 100% Methylation (MC). For each testing plate (e.g., 96 well plate), 10 ng of MC sample is tested two or three times. The MC control allows for normalization of the intra-assay variations, including reagent batches and PCR instruments. (FIG. 23). The standard curve for this assay is based on 7-point serial dilutions of known quantities of MssI-modified genomic DNA (12-3000 copy of haploid genome). The amplification efficiency of each quantified target in the tested group was reported for quality control. Most importantly, for each analyte the raw copy number of each quantified region was calculated against the primer set's own standard curve. Therefore, the effect of amplification efficient difference among the primer sets could be minimized using this assay (FIGS. 23 and 24). A no template control (NTC) was also included in each 96-well testing plate as well as a 0% methylated control (FIG. 23). Thus, the employment of each of these controls, significantly enhances the precision and reproducibility of the assay.

Figure 25:
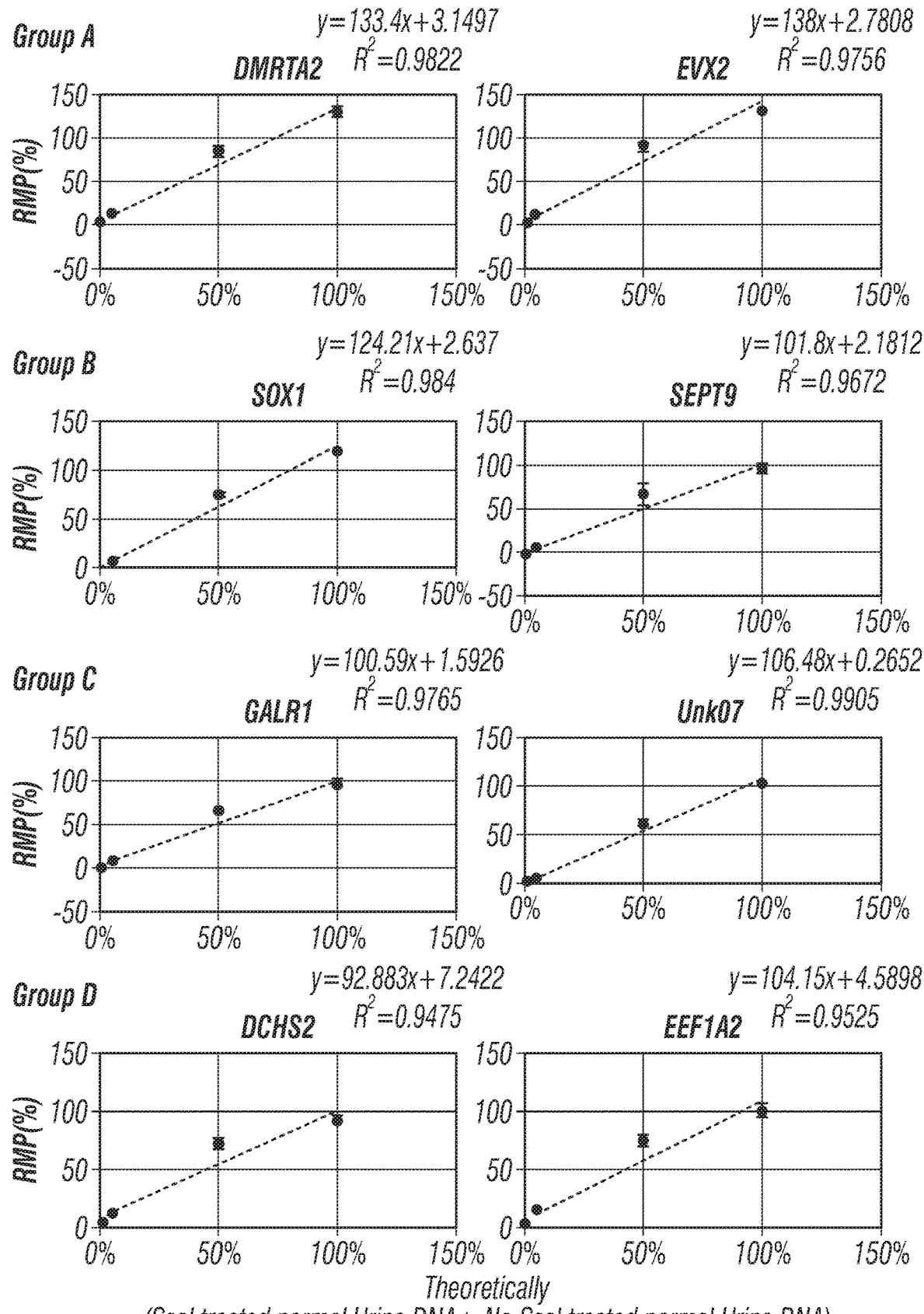
FIG. 25: Results showing linearity of MMSP assay for 16 targeted genes based on repeated measurements of relative methylation percentage values of DNA mixtures containing 100%, 50%, 5%, 1%, 0.5% and 0% of methylated (M.SssI-treated) normal urine DNA.
Figure 25:
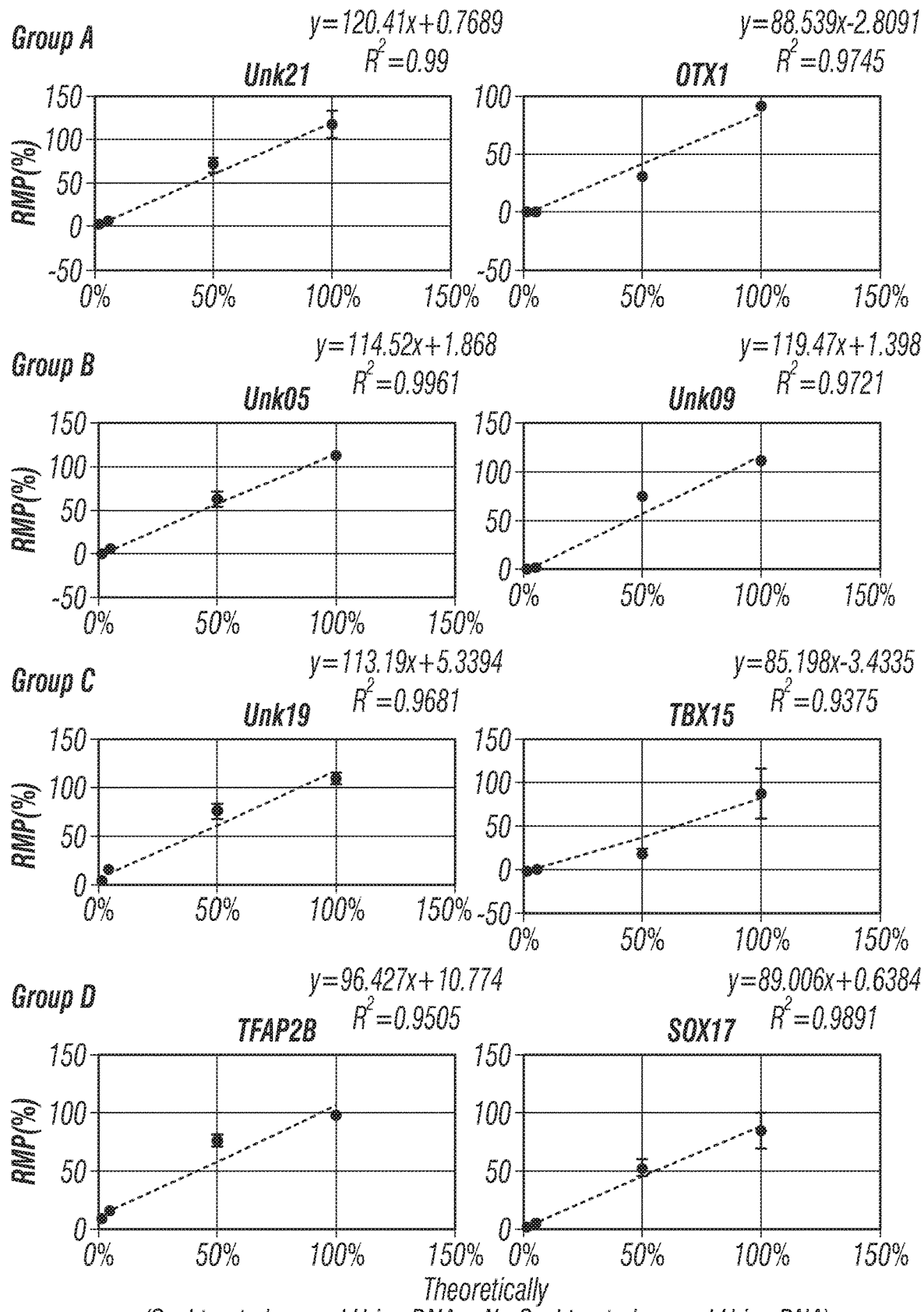

The assay also showed good linearity for all of the 16 targeted genes based on repeated measurements of relative methylation percentage values on DNA mixtures containing 100%, 50%, 5%, 1%, 0.5% and 0% of methylated (M.SssI-treated) normal urine DNA (FIG. 25)

Methylation analysis: For each analyte, the raw copy number of each targeted region and internal control was automatically calculated according to the standard curve. If more than one PCR reaction was performed for a sample, the mean value of duplicates or triplicates was calculated for following analysis. The relative methylation percentage calculation based on following equation.

$$RMP = \frac{(\text{Target mean value})\text{sample}/(COL2A1 \text{ mean value})\text{sample}}{(\text{Target mean value})P.C./(COL2A1 \text{ mean value})P.C.} \times 100$$

If the standard curve was not performed, then an alternative calculation for methylation percentage was based on delta CT as follows:

$$RPM = \frac{2^{\wedge} - (\text{Target mean } CT \text{ value})\text{sample} - (\text{Target mean } CT \text{ value})P.C.}{2^{\wedge} - (COL2A1 \text{ mean } CT \text{ value})\text{sample} - (COL2A1 \text{ mean } CT \text{ value})P.C.} \times 100$$

Validation:

35 urine samples from normal healthy people were collected and the genomic DNA was extracted using the Quick-DNA™ Urine Kit (Zymo, USA). In addition, genomic DNA are extracted using the ZR Urine DNA Isolation Kit and ZR Genomic DNA—Tissue Kits (Zymo, USA) from 9 bladder cancer tumor tissues. The DNA concentration was measured by Nanodrop and 250 ng of each sample was subjected to bisulfite conversion using the EZ Direct kit (Zymo, USA). The converted DNA was eluted into nuclease free water and diluted into about 2 ng/ul for polymerase chain reaction.

25 ul of reaction master mix (1U AmpliGold Taq enzyme, 1× ampliGold Buffer, 400 uM dNTP, 5.5 mM MgCl2, 300 nM Primers, 100 nM probes, PCR enhancer (optional)) of Group A, B, C, D was premade separately and loaded to a 96 well plate (FIG. 23). 5 ul of sample DNA ware used per reaction. Each sample was tested in duplicated. 5 ul of DNA standards were loaded into each designated well. A technical duplication of standard curves was performed for each 96-well plate. 5 ul of 100% methylated Positive Control (MC) samples was also tested twice.

Figure 26:
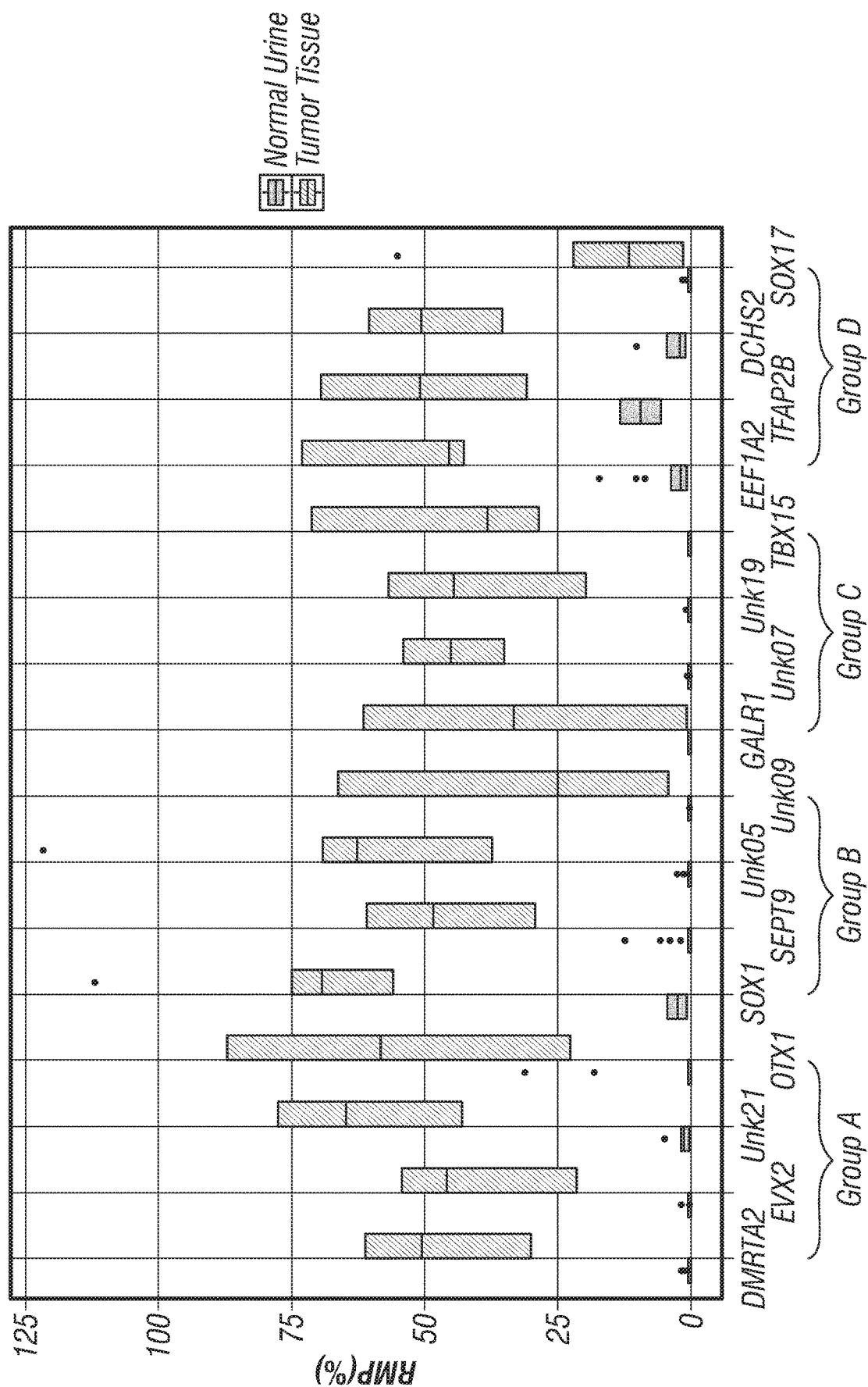
FIG. 26: Results from MMSP assay analysis of 35 normal urine samples and 9 bladder cancer tumor tissues for 16 biomarkers divided into four groups A, B, C and D.

Real-time PCR was performed on the CFX96 Touch™ Real-Time PCR Detection System. The raw copy number of each of the targeting regions in each sample was automatically reported by the instrument's program. The relative methylation percentages were calculated as described. As shown in FIG. 26, all of 16 tested biomarkers in the assay were highly methylated in bladder cancer tissue samples and also showed extremely low background of DNA methylation in healthy urine samples. Thus, these results confirmed that these markers can be used in bladder cancer relevant diagnostic and prognostic implications.

Validation #2:

DNA was extracted from 15 bladder cancer urine samples and bisulfite converted and stored in −20° C. for more than one year. These samples were diluted with 80 ul of H2O for this assay. 25 ul of reaction master mix (1U AmpliGold Taq enzyme, 1× ampliGold Buffer, 400 uM dNTP, 5.5 mM MgCl2, 300 nM Primers, 100 nM probes, 1.5 ul DMSO) of Group B was premade separately and loaded to a 96 well plate. 5 ul of sample DNA was used per reaction. Each sample was tested in duplicate. A technical duplication of standard curves was performed for each 96-well plate. 5 ul of 100% methylated Positive Control (MC) sample was also tested twice.

Real-time PCR was performed on the CFX96 Touch™ Real-Time PCR Detection System. The raw copy number of each targeting regions in each sample was automatically reported by the instrument's program. To ensure the statistical significance, only the samples which showed at least 200 copy of COL2A1 were kept for the next step of analysis. The relative methylation percentages were calculated as described previously. As shown in FIG. 27A, the group B markers clearly identified the bladder cancer samples.

In addition, 3 months after therapy, the group B markers detected a dramatic drop in DNA methylation indicating the success of the therapy. In the following check-up, the group B markers confirmed that bladder cancer did not recur (FIG. 27A). For a patient with bladder cancer recurrence, the group B markers showed a modest increase of DNA methylation as early as 18 months after the first clinical visit and a significant increase at 31.5 months. This patient was diagnosed with bladder cancer recurrence at 39.5 months. Thus, these data strongly suggest that these markers can be used to detect and predict bladder cancer recurrence (FIG. 27B).

Validation #3:

A pre-clinical study was conducted to further validate the assay in urine samples from healthy individuals and bladder cancer patients. 33 urine samples from bladder cancer patients were purchased from Geneticist-IIBGR (Glendale, Calif.). The urine samples were collected before transurethral resection of the bladder tumor (TURBT) and without any chemotherapy. 20 normal urine samples were collected internally (consented) with diverse age, gender and smoking history. All the urine samples were preserved in Urine Conditioning Buffer (Zymo research, D3061-1) upon collection. Both cellular and cell free DNA from urine samples were extracted using Quick-DNA™ Urine Kit (Zymo, USA). DNA concentration was measured by Nanodrop and 150 ng of each sample was subjected to bisulfite conversion using EZ Direct kit (Zymo, USA). The converted DNA was eluted into nuclease free water and diluted into about 2 ng/ul for polymerase chain reaction.

Biomarkers in Group A, B, C, D were tested as in Assay Validation #1, except that each sample was tested three times. The RMP results for each sample were subjected to further statistical analysis. The best biomarker, Unk05 in Group B, was selected based on a special algorithm. Using Unk05 (cut-off value of 1.5%) allowed for stratification of samples in a bladder cancer and bladder cancer free group (Sensitivity 90.9%; Specificity 85%). Thus, the assay has enhanced sensitivity and specificity as compared to current urine-based tumor markers in bladder cancer (FIG. 28).

Example 6—Statistical Analysis for Preclinical Urine Cohort

Weeding Trivial Biomarkers Using the Random Forest Algorithm:

A statistical model was built to predict the probability of the presence of bladder cancer by measuring DNA methylation of a set of CpG sites in a urine sample. DNA methylation levels of twelve bladder cancer specific CpG sites (Table 7) of urine samples were obtained using the CARE assay and the multiplex methylation-specific qPCR (MMSP) assay. Urine samples were randomly split into a training set and a test set in the ratio of 75% and 25% respectively. A subgroup from the twelve biomarkers with the lowest root mean squared error (RMSE) was identified by using the recursive feature selection algorithm called random forest (Svetnik 2003; implemented in the R package caret).

Assignment of Different Weights to the Selected Biomarkers by the Generalized Linear Model:

A coefficient was assigned to each of the selected CpG sites and an intercept was obtained using the generalized linear regression model (Friedman, 2008; implemented in the R package glmnet), regressing DNA methylation on cancer status of the urine samples (absence or presence of bladder cancer). The alpha parameter of 0.5 was used to balance having smaller variance and less variables, and the lambda parameter which helps achieve the smallest error was chosen using cross validation of the training data.

Calculation of Probability of Presence of Bladder Cancer Using Logistic Regression:

Logistic regression relates a binary outcome variable (like presence or absence of cancer) to a group of predictor variables (like a set of CpG sites) (Freedman 2009). The probability of presence of bladder cancer is calculated by the following formula: $\log(p/(1-p)) = X0 + CpG1*X1 + \ldots + CpGn*Xn = X$, where p represents the probability of bladder cancer, n is the number of selected CpG sites, X0 is the intercept, X1 is the coefficient of the CpG site 1, CpG1 is the DNA methylation value of the CpG site 1, and so on. X is the sum of the intercept and every biomarker's weighted DNA methylation value which is CpG*coefficient. Therefore, $p = \exp(X)/(1+\exp(X))$.

Figure 29:
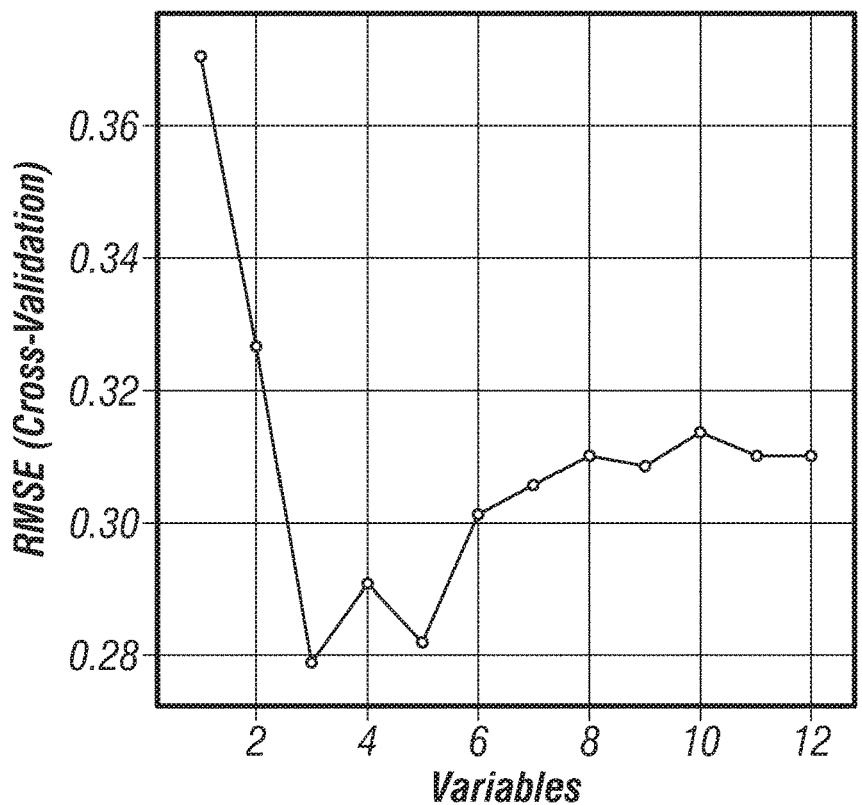
FIG. 29: Selection of a panel of three CpG sites with the lowest RMSE error by Random Forest for the CARE assay.

Results of the CARE Assay:

DNA methylation values of the twelve CpG sites were obtained for the 53 urine samples from 20 healthy individuals and 33 bladder cancer patients. The samples were randomly split into a Training set (39 samples; 13 healthy and 26 cancer) and a Test set (14 samples; 7 healthy and 7 cancer). A subgroup of three CpG sites of #05 (Unk 05), #36 (SOX17) and #09 (Unk09) was identified having the lowest RMSE error by the Random Forest algorithm (FIG. 29). The glmnet function assigned them coefficients of 39.0831, 104.1071, and 21.5371 respectively, along with an intercept of −0.5092. Then the probability of bladder cancer was calculated for all the samples. A sample was classified as bladder cancer positive if its probability was equal or greater than 50% and negative if less than 50%. The CARE assay achieved sensitivity and specificity of 88.46% and 84.62% in the Training set, and 100% and 85.71% in the Test set (Table 10).

TABLE 17

Statistical analysis of preclinical urine cohort by Multilpex methylation-sensitive qPCR assay.

| | Whole Cohort | Training Set | Test Set |
| --- | --- | --- | --- |
| Total Sample | 53 | 39 | 14 |
| Bladder Cancer | 33 | 26 | 7 |
| Control | 20 | 13 | 7 |
| True Positive (TP) | 30 | 24 | 6 |
| False Negative (FN) | 3 | 2 | 1 |
| True Negative (TN) | 17 | 11 | 6 |
| False Positive (FP) | 3 | 2 | 1 |
| Sensitivity % | 90.90 | 92.30 | 85.71 |
| Specificity % | 85.00 | 84.62 | 85.71 |
| Positive Predictive Value % | 90.90 | 92.30 | 85.71 |
| Negative Predictive Value % | 85.00 | 84.62 | 85.71 |

Sensitivity % = [TP/(TP + FN)] * 100
Specificity % = [TN/(TN + FP)] * 100
Positive Predictive Value % = [TP/(TP + FP)] * 100
Negative Predictive Value % = [TN/(TN + FN)] * 100

Figure 30:
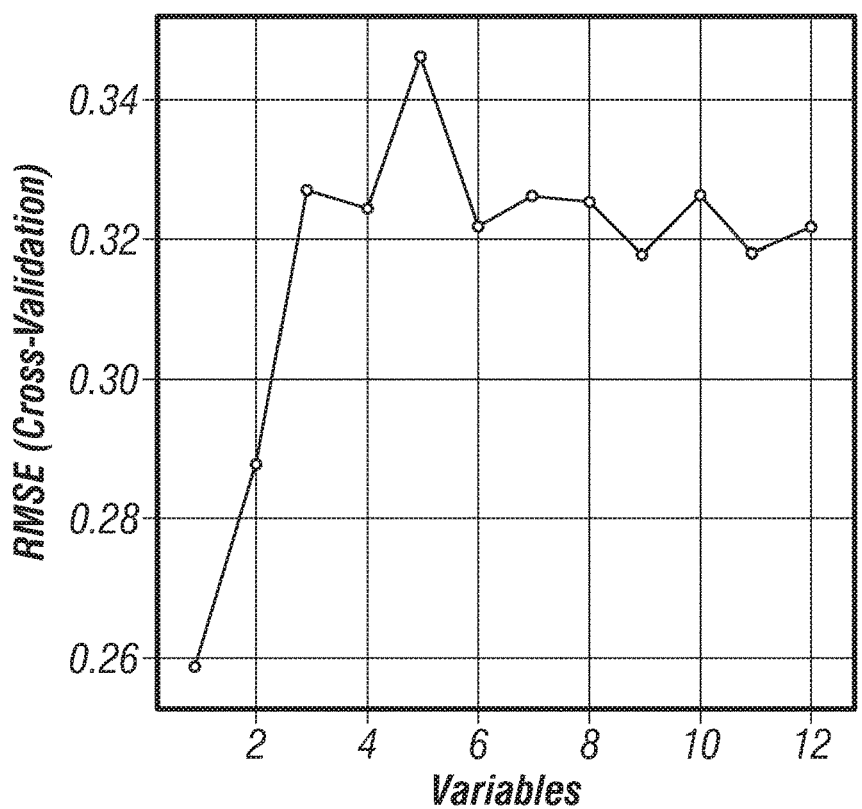
FIG. 30: Selection of one and two CpG sites with the lowest and second lowest RMSE errors by Random Forest for the MMSP.

Results of the MMSP assay: DNA methylation was measured using the MMSP assay for the same sample set as that of the CARE assay. The Random Forest algorithm identified one single CpG site R3N5 [See Table 12] with the lowest RMSE error (FIG. 30). The glmnet could not assign a coefficient to a single variable. However, a sample was classified as bladder cancer positive if its methylation value was equal to or greater than 1.5% and negative if less than 1.5%. The MMSP assay had its sensitivity and specificity of 90.9% and 85.00% respectively (Table 17).

Example 7—Aneuploidy Detection

Another hallmark of cancer cells is the chromosomal instability that frequently results in an increased chromosomal ploidy or deletion. In particular tetraploidy of chromosomes 3, 7 and 17, and loss of the chromosomal region 9p21 are frequently associated with urothelial carcinomas and accumulate during the development of bladder cancer starting three years before diagnosis (Bonberg et al., 2014). To note, markers #05, #07 and POLR2A (Set A and B) are positioned on chromosomes 7, 17 and 17 respectively, make them suitable for the detection of frequent chromosomal aberrations associated with bladder cancer.

Although so far we did not deeply investigated this aspect, an interesting aspect of CARE assay is that it can provide information about the presence of chromosomal aneuploidy in the sample analyzed. Indeed, the qPCR signal obtained from each marker in the undigested sample is equal to the number of copy of DNA added initially to the reaction (each marker, including the endogenous controls, is a single-copy locus). Therefore, the comparison between the signal obtained from a specific marker in an undigested euploid sample (e.g. the undigested reaction performed for E.D.C. control) and the signal detected for the same marker in an undigested clinical sample (undigested sample control) might point out the eventual presence of an extra or a missing copy of the marker under analysis. For example, if we analyze a urine sample collected from an individual affected by a bladder cancer in which marker SOX1 (#27) is duplicated, we might in principle expect that the signal detected from SOX1 (but not for the other markers) in the undigested clinical sample is doubled compared to the signal obtained from the undigested EDC control.

Despite this aspect might be interesting since it can provide additional information for bladder cancer diagnostic purposes, we have to consider that the possibility to identify chromosomal aberration taking advantage of CARE assay is strongly dependent from the amount of normal and cancer cells (and more specifically aneuploid cells) present in the original sample. Indeed, if the aberrant cancer cells represent only a small fraction of the cell population present in the urine sample, the detection of aneuploidy using CARE assay will not be possible. More data regarding this aspect will be collected from future experiments.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Babjuk et al., EAU guidelines on non-muscle-invasive urothelial carcinoma of the bladder, the 2011 update. *Eur Urol* 2011; 59: 997-1008.

Bernstein et al., 2007

Giovannucci and Ogino, 2005

Lintula and Hotakainen, Developing biomarkers for improved diagnosis and treatment outcome monitoring of bladder cancer. *Expert Opin Biol Ther* 2010; 10:1169-80.

Millan-Rodriguez et al., Primary superficial bladder cancer risk groups according to progression, mortality and recurrence. J Urol 2000; 164:680-4.

Morgan and Clark, Bladder cancer. *Curr Opin Oncol* 2010; 22: 242-9.

Parker and Spiess, Current and emerging bladder cancer urinary biomarkers. *Scientific World Journal* 2011; 11:1103-12.

Reinert T, Methylation markers for urine-based detection of bladder cancer: The next generation of urinary markers for diagnosis and surveillance of bladder cancer. *Adv Urol* 2012; 2012:503271.

Shelley et al., Intravesical therapy for superficial bladder cancer: A systematic review of randomised trials and meta-analyses. *Cancer Treat Rev* 2010; 36:195-205.

Siegel et al., Cancer statistics, 2011: The impact of eliminating socioeconomic and racial disparities on premature cancer deaths. CA *Cancer J Clin* 2011; 61: 212-36.

Sobin et al., TNM classification of malignant tumours. 7th ed. Wiley-Blackwell; 2009.

Widschwendter et al., Cancer Research, 64: 3807-3813, 2004

What is claimed is:

1. A reaction mixture comprising:
   (i) at least two methylation sensitive restriction endonucleases;
   (ii) a hot-start DNA polymerase;
   (iii) a pH buffered salt solution;
   (iv) dNTPs;
   (v) a substantially purified genomic DNA sample;
   (vi) DNA primer pairs for polymerase chain reaction (PCR) amplification of at least a first genomic region, a second genomic region and a third genomic region in the DNA sample, wherein the first genomic region, the second genomic region and the third genomic region are different regions;
   (vii) fluorescent probes complementary to sequences in said first genomic region, said second genomic region, and said third genomic region for quantitative detection of amplified sequences from the first genomic region, the second genomic region, and the third genomic region, wherein each of the probes comprises a distinct fluorescent label wherein:
   (I) the first genomic region is a cleavage control that is known to be unmethylated;
   (II) the second genomic region is a copy number control that does not include any cut site of the methylation sensitive restriction endonucleases of the reaction mixture; and
   (III) the third genomic region is a test region having an unknown amount of methylation and including at least three cut sites of the methylation sensitive restriction endonucleases of the reaction mixture.

2. The reaction mixture of claim 1, wherein the third genomic region comprises OTX1 gene, ZIC4 gene, PCDHGA4 gene, TFAP2B gene, Unk 05 region, SCT gene, Unk 07 region, GALR1 gene, Unk 09 region, DMRTA2 gene, SIX3 gene, C1ORF70 gene, Unk 13 region, Unk 14 region, GALR1 gene, SEPT9 gene, FZD7 gene, DCHS2 gene, Unk 19 region, KCNA3 gene, Unk 21 region, DPM2 gene, TBX15 gene, Unk 24 region, CCDC81 gene, KCNA6 gene, SOX1 gene, Unk 28 region, Unk 29 region, EVX2 gene, CERKL gene, EEF1A2 gene, POU4F2 gene, SHH gene, Unk 35 region, SOX17 gene, Unk 37 region, HOXA9 gene, NPY gene, IRAK3 gene, or TJP2 gene.

3. The reaction mixture of claim 1, further comprising DNA primer pairs for a fourth genomic region, a fifth genomic region or a further genomic region, wherein the fourth genomic region, the fifth genomic region or the further genomic region is a test region having an unknown amount of methylation and including at least three cut sites of the methylation sensitive restriction endonucleases of the reaction mixture.

4. The reaction mixture of claim 3, wherein the third genomic region, the fourth genomic region, the fifth genomic region or the further genomic region comprises OTX1 gene, ZIC4 gene, PCDHGA4 gene, TFAP2B gene, Unk 05 region, SCT gene, Unk 07 region, GALR1 gene, Unk 09 region, DMRTA2 gene, SIX3 gene, C1ORF70 gene, Unk 13 region, Unk 14 region, GALR1 gene, SEPT9 gene, FZD7 gene, DCHS2 gene, Unk 19 region, KCNA3 gene, Unk 21 region, DPM2 gene, TBX15 gene, Unk 24 region, CCDC81 gene, KCNA6 gene, SOX1 gene, Unk 28 region, Unk 29 region, EVX2 gene, CERKL gene, EEF1A2 gene, POU4F2 gene, SHH gene, Unk 35 region, SOX17 gene, Unk 37 region, HOXA9 gene, NPY gene, IRAK3 gene, or TJP2 gene.

5. The reaction mixture of claim 4, wherein the third genomic region, the fourth genomic region, the fifth genomic region or the further genomic region comprises Unk 05 region, Unk 09 region or Unk 21 region.

6. The reaction mixture of claim 1, wherein the first genomic region comprises GAPDH gene.

7. The reaction mixture of claim 1, wherein the second genomic region comprises POLR2A gene.

8. The reaction mixture of claim 7, wherein the fluorescent probes and/or primer pairs are specific for the locus of POLR2A gene.

9. The reaction mixture of claim 8, wherein the fluorescent probes or primer pairs comprise at least one of SEQ ID NOs:49-90 or are selected from the group consisting of SEQ ID NOs:49-90.

10. The reaction mixture of claim 1, wherein the fluorescent probes and/or primer pairs are specific for a locus of POLR2A gene, GAPDH gene, SOX1 gene, GALR1 gene, DMRTA2b gene, Unk05 region, Unk07 region, EVX2 gene, SOX17 gene, DCHS2 gene, Unk09 region, EEF1A2 gene, Unk19 region, or Unk21 region.

11. The reaction mixture of claim 1, wherein at least one of the fluorescent probes or primer pairs comprise at least one of SEQ ID NOs:49-90.

12. The reaction mixture of claim 1, wherein at least one of the fluorescent probes and primer pairs are selected from the group consisting of SEQ ID NOs:49-90.

13. The reaction mixture of claim 1, wherein the distinct fluorescent label includes a fluorescent squaraine dye or infrared dye.

14. The reaction mixture of claim 13, wherein the fluorescent squaraine dye or the infrared dye is 2,4-Bis[1,3,3-trimethyl-2-indolinylidenemethyl]cyclobutenediylium-1,3-dio-xolate, 2,4 Bis[3,3-dimethyl-2-(1H-benz[e] indolinylidenemethyl)]cyclobutenediylium-1,-3-dioxolate, or 2,4-Bis[3,5-dimethyl-2-pyrrolyl]cyclobutenediylium-1,3-diololate.

15. The reaction mixture of claim 1, wherein the least two methylation sensitive restriction endonucleases include SmaI, HpaII, BssHII, BstUI, SacII, EagI and/or NotI.

16. The reaction mixture of claim 1, wherein the least two methylation sensitive restriction endonucleases include AciI, HpyCH4IV, HinPII and/or HpaII.

17. The reaction mixture of claim 1, wherein the least two methylation sensitive restriction endonucleases include AciI, HpyCH4IV, HinPII or HpaII.

18. The reaction mixture of claim 1, wherein the least two methylation sensitive restriction endonucleases include MspI and/or HpaII.

19. The reaction mixture of claim 1, wherein the reaction mixture is in a kit.

\* \* \* \* \*

SEQUENCE LISTING

<160> NUMBER OF SEQ ID NOS: 90

<210> SEQ ID NO 1
<211> LENGTH: 16
<212> TYPE: DNA
<213> ORGANISM: Artificial sequence
<220> FEATURE:
<223> OTHER INFORMATION: Synthetic oligonucleotides

<400> SEQUENCE: 1
tcgcggaagt agcggc                                                    16

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 2
cacctcctcc cgcataaaaa                                                20

<210> SEQ ID NO 3
<211> LENGTH: 29
<212> TYPE: DNA
<213> ORGANISM: Artificial sequence
<220> FEATURE:
<223> OTHER INFORMATION: Synthetic oligonucleotides

<400> SEQUENCE: 3
aacgcctcga acacgtccaa ctataaacg                               29

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 4
ggagggatta ttattcggtt cgt                                     23

<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotides

<400> SEQUENCE: 5
ccatacccgc gtccaaac                                           18

<210> SEQ ID NO 6
<211> LENGTH: 27
<212> TYPE: DNA
<213> ORGANISM: Artificial sequence
<220> FEATURE:
<223> OTHER INFORMATION: Synthetic oligonucleotides

<400> SEQUENCE: 6
atacgccgaa tacaacaaca cgtccga                                 27

<210> SEQ ID NO 7
<211> LENGTH: 27
<212> TYPE: DNA
<213> ORGANISM: Artificial sequence
<220> FEATURE:
<223> OTHER INFORMATION: Synthetic oligonucleotides

<400> SEQUENCE: 7
tcgtacgtaa gtcgcgtata gtattgt                                 27

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotides

<400> SEQUENCE: 8
aatccgaact aaccgccg                                           18

<210> SEQ ID NO 9
<211> LENGTH: 17
<212> TYPE: DNA
<213> ORGANISM: Artificial sequence
<220> FEATURE:
<223> OTHER INFORMATION: Synthetic oligonucleotides

```
<400> SEQUENCE: 9
cgccgcccaa aacgcga                                                  17

<210> SEQ ID NO 10
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 10
aggtaagagt ttcggcggc                                                19

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 11
cctcaaccct cgaacccaac                                               20

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotides

<400> SEQUENCE: 12
tcgcgacaaa cacgcttccg ccta                                          24

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotides

<400> SEQUENCE: 13
tcggcgaaga tttggagc                                                 18

<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 14
cgcgaccacg aaacctaaa                                                19

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 15
ttttatttgc gcggttgtag tcggc                                         25

<210> SEQ ID NO 16
```

```
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 16
cgcgtaaaag gtaggatcgc                                              20

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 17
aactcgaaac tctacccccg a                                            21

<210> SEQ ID NO 18
<211> LENGTH: 30
<212> TYPE: DNA
<213> ORGANISM: Artificial sequence
<220> FEATURE:
<223> OTHER INFORMATION: Synthetic oligonucleotides

<400> SEQUENCE: 18
aacgccgact caacaaaaaa ttatttcgaa                                   30

<210> SEQ ID NO 19
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 19
agcgatagta gcgtttgtgg ttt                                          23

<210> SEQ ID NO 20
<211> LENGTH: 17
<212> TYPE: DNA
<213> ORGANISM: Artificial sequence
<220> FEATURE:
<223> OTHER INFORMATION: Synthetic oligonucleotides

<400> SEQUENCE: 20
gcgaaccccc aaatacg                                                 17

<210> SEQ ID NO 21
<211> LENGTH: 29
<212> TYPE: DNA
<213> ORGANISM: Artificial sequence
<220> FEATURE:
<223> OTHER INFORMATION: Synthetic oligonucleotides

<400> SEQUENCE: 21
tcgcaaccat aacgtaatat cgaccctca                                    29

<210> SEQ ID NO 22
<211> LENGTH: 26
<212> TYPE: DNA
<213> ORGANISM: Artificial sequence
<220> FEATURE:
<223> OTHER INFORMATION: Synthetic oligonucleotides

<400> SEQUENCE: 22
```

-continued

```
gtttttgagt ttataggtcg ggattt                                          26

<210> SEQ ID NO 23
<211> LENGTH: 15
<212> TYPE: DNA
<213> ORGANISM: Artificial sequence
<220> FEATURE:
<223> OTHER INFORMATION: Synthetic oligonucleotides

<400> SEQUENCE: 23
ctatcaccgc cgccg                                                      15

<210> SEQ ID NO 24
<211> LENGTH: 30
<212> TYPE: DNA
<213> ORGANISM: Artificial sequence
<220> FEATURE:
<223> OTHER INFORMATION: Synthetic oligonucleotides

<400> SEQUENCE: 24
aaattaaacg acaacgcacg cgactaacaa                                      30

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 25
agcggtgacg gtagtggttt                                                 20

<210> SEQ ID NO 26
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 26
ctacacccta atacaaccgt ccg                                             23

<210> SEQ ID NO 27
<211> LENGTH: 28
<212> TYPE: DNA
<213> ORGANISM: Artificial sequence
<220> FEATURE:
<223> OTHER INFORMATION: Synthetic oligonucleotides

<400> SEQUENCE: 27
aacccgttct tccaattacg ctaccgaa                                        28

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 28
gcggacgtta gttagtcggc                                                 20

<210> SEQ ID NO 29
<211> LENGTH: 19
<212> TYPE: DNA
```

<213> ORGANISM: Artificial sequence
<220> FEATURE:
<223> OTHER INFORMATION: Synthetic oligonucleotides

<400> SEQUENCE: 29
cccgaatccc tatccgaaa                                                    19

<210> SEQ ID NO 30
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 30
cgcccactcc gacaccaacg t                                                 21

<210> SEQ ID NO 31
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 31
cgcgtttaat tggttgcga                                                    19

<210> SEQ ID NO 32
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 32
tatctattcg tcccgcccg                                                    19

<210> SEQ ID NO 33
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 33
aaatccgcct cctcgacccg aaa                                               23

<210> SEQ ID NO 34
<211> LENGTH: 26
<212> TYPE: DNA
<213> ORGANISM: Artificial sequence
<220> FEATURE:
<223> OTHER INFORMATION: Synthetic oligonucleotides

<400> SEQUENCE: 34
ggttggtata tcgaggtttc gtagtt                                            26

<210> SEQ ID NO 35
<211> LENGTH: 15
<212> TYPE: DNA
<213> ORGANISM: Artificial sequence
<220> FEATURE:
<223> OTHER INFORMATION: Synthetic oligonucleotides

<400> SEQUENCE: 35
cgcgtctacc cgccc                                                        15

<210> SEQ ID NO 36
<211> LENGTH: 26
<212> TYPE: DNA
<213> ORGANISM: Artificial sequence
<220> FEATURE:
<223> OTHER INFORMATION: Synthetic oligonucleotides

<400> SEQUENCE: 36
aaacgacgaa cgaatcaaac gcgact                                    26

<210> SEQ ID NO 37
<211> LENGTH: 29
<212> TYPE: DNA
<213> ORGANISM: Artificial sequence
<220> FEATURE:
<223> OTHER INFORMATION: Synthetic oligonucleotides

<400> SEQUENCE: 37
ggtatttggg attagtatat gtttagcgt                                 29

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 38
cctcaacgac ctccaactcg                                           20

<210> SEQ ID NO 39
<211> LENGTH: 29
<212> TYPE: DNA
<213> ORGANISM: Artificial sequence
<220> FEATURE:
<223> OTHER INFORMATION: Synthetic oligonucleotides

<400> SEQUENCE: 39
actacaactt ctaacaaaac gacgcgccg                                 29

<210> SEQ ID NO 40
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 40
gattcgcgtt agagtcggag tta                                       23

<210> SEQ ID NO 41
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 41
cgtcgaactc aaacctcgaa a                                         21

<210> SEQ ID NO 42
<211> LENGTH: 17
<212> TYPE: DNA
<213> ORGANISM: Artificial sequence
<220> FEATURE:

<223> OTHER INFORMATION: Synthetic oligonucleotides

<400> SEQUENCE: 42
cgtcgcgttt tcgtcgt                                                  17

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 43
gcgtatacgg ttttggggtc                                               20

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotides

<400> SEQUENCE: 44
caaacttccg cgcccaac                                                 18

<210> SEQ ID NO 45
<211> LENGTH: 27
<212> TYPE: DNA
<213> ORGANISM: Artificial sequence
<220> FEATURE:
<223> OTHER INFORMATION: Synthetic oligonucleotides

<400> SEQUENCE: 45
ctcgccacgc tcaatacccg ttttacc                                       27

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 46
ggacgtggga ttcggattac                                               20

<210> SEQ ID NO 47
<211> LENGTH: 31
<212> TYPE: DNA
<213> ORGANISM: Artificial sequence
<220> FEATURE:
<223> OTHER INFORMATION: Synthetic oligonucleotides

<400> SEQUENCE: 47
ttttctacac aaatataacc aataaaacga c                                  31

<210> SEQ ID NO 48
<211> LENGTH: 22
<212> TYPE: DNA
<213> ORGANISM: Artificial sequence
<220> FEATURE:
<223> OTHER INFORMATION: Synthetic oligonucleotides

<400> SEQUENCE: 48
cgaaccgatc ccgcgtcgtt aa                                            22

```
<210> SEQ ID NO 49
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 49
acctacctct ccaagctatt c                                               21

<210> SEQ ID NO 50
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 50
ggtgtaattg ggactggttg g                                               21

<210> SEQ ID NO 51
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 51
tactcaccca ccagcccgaa cta                                             23

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 52
cgtagctcag gcctcaagac                                                 20

<210> SEQ ID NO 53
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 53
gaggagcaga gagcgaagc                                                  19

<210> SEQ ID NO 54
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 54
ctcagccagt cccagcccaa g                                               21

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotides
```

<400> SEQUENCE: 55
ccacgactgc acctgtttgc					20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 56
ggcagaaaca cacgcactcg					20

<210> SEQ ID NO 57
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 57
tcggcctctt tggcaagtgg ttt				23

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 58
acccaccctc tctcagaagg					20

<210> SEQ ID NO 59
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 59
agtttaggag tctgagcttc c					21

<210> SEQ ID NO 60
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 60
cgcaaagacg gtgccaccag g					21

<210> SEQ ID NO 61
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 61
gcagtgccgt agagcagct					19

<210> SEQ ID NO 62
<211> LENGTH: 22

<212> TYPE: DNA
<213> ORGANISM: Artificial sequence
<220> FEATURE:
<223> OTHER INFORMATION: Synthetic oligonucleotides

<400> SEQUENCE: 62
ccctcaaggg ccacaaacgc ta                                                22

<210> SEQ ID NO 63
<211> LENGTH: 24
<212> TYPE: DNA
<213> ORGANISM: Artificial sequence
<220> FEATURE:
<223> OTHER INFORMATION: Synthetic oligonucleotides

<400> SEQUENCE: 63
cacaggcagt ccttccagcg acag                                              24

<210> SEQ ID NO 64
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 64
cactcacgtc ttcgtagtca g                                                 21

<210> SEQ ID NO 65
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 65
ttggagtgtg acggtaaaag c                                                 21

<210> SEQ ID NO 66
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 66
cgtacagcac tgcagggtcc g                                                 21

<210> SEQ ID NO 67
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 67
gggaggaccc ctcgttagc                                                    19

<210> SEQ ID NO 68
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 68
ctcagcgtcc gacccact                                                19

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 69
tgggctcgag ggctgagggc                                               20

<210> SEQ ID NO 70
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 70
aggcttccga ggcctgagc                                                19

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 71
agcgactctc cttcctgacg                                               20

<210> SEQ ID NO 72
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 72
cgtaccctgg caaacaaacg acc                                           23

<210> SEQ ID NO 73
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 73
tgggcgtggg cctaacgac                                                19

<210> SEQ ID NO 74
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 74
cccgtgttct ggcctgtcg                                                19

<210> SEQ ID NO 75
<211> LENGTH: 22
<212> TYPE: DNA
<213> ORGANISM: Artificial sequence
<220> FEATURE:
<223> OTHER INFORMATION: Synthetic oligonucleotides

<400> SEQUENCE: 75
tgggtacgct gtagaccaga cc                                        22

<210> SEQ ID NO 76
<211> LENGTH: 18
<212> TYPE: DNA
<213> ORGANISM: Artificial sequence
<220> FEATURE:
<223> OTHER INFORMATION: Synthetic oligonucleotides

<400> SEQUENCE: 76
cgcacgcgac agacctcg                                             18

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 77
tggatgagaa cgacaacccg                                           20

<210> SEQ ID NO 78
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 78
cggtactcgt cctgctcaaa gac                                       23

<210> SEQ ID NO 79
<211> LENGTH: 18
<212> TYPE: DNA
<213> ORGANISM: Artificial sequence
<220> FEATURE:
<223> OTHER INFORMATION: Synthetic oligonucleotides

<400> SEQUENCE: 79
accgaggccc ctacctgg                                             18

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotides

<400> SEQUENCE: 80
gttagaaacg caggccaggc                                           20

<210> SEQ ID NO 81
<211> LENGTH: 22
<212> TYPE: DNA
<213> ORGANISM: Artificial sequence
<220> FEATURE:
<223> OTHER INFORMATION: Synthetic oligonucleotides

<400> SEQUENCE: 81
cactgaacga ccccttctcc ag                                        22

<210> SEQ ID NO 82
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 82
gccgacttgg tgaccttgc                                              19

<210> SEQ ID NO 83
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 83
ggccagagcc ctggggttg                                              19

<210> SEQ ID NO 84
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 84
ccacgttctt gatgacgcct acg                                         23

<210> SEQ ID NO 85
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 85
gacgtggtgt tcgcttttgg c                                           21

<210> SEQ ID NO 86
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 86
cgcacgtgca gctcgtagg                                              19

<210> SEQ ID NO 87
<211> LENGTH: 23
<212> TYPE: DNA
<213> ORGANISM: Artificial sequence
<220> FEATURE:
<223> OTHER INFORMATION: Synthetic oligonucleotides

<400> SEQUENCE: 87
cccgtggatt accagagtca gga                                         23

<210> SEQ ID NO 88
<211> LENGTH: 19
<212> TYPE: DNA
<213> ORGANISM: Artificial sequence
<220> FEATURE:
<223> OTHER INFORMATION: Synthetic oligonucleotides

```
<400> SEQUENCE: 88
acacgccgaa cacacgtgc                                                19

<210> SEQ ID NO 89
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 89
ccgtccgtgt gtcctgtgc                                                19

<210> SEQ ID NO 90
<211> LENGTH: 22
<212> TYPE: DNA
<213> ORGANISM: Artificial sequence
<220> FEATURE:
<223> OTHER INFORMATION: Synthetic oligonucleotides

<400> SEQUENCE: 90
cctaattggc tgcgaacggt cc                                            22
```